(12) United States Patent
Leone-Bay et al.

(10) Patent No.: US 12,303,487 B2
(45) Date of Patent: May 20, 2025

(54) N-ACYLATED FATTY AMINO ACIDS TO REDUCE ABSORPTION VARIABILITY IN CANNABINOID BASED COMPOSITIONS

(71) Applicant: Spoke Sciences, Inc., Bainbridge Island, WA (US)

(72) Inventors: Andrea Leone-Bay, Ridgefield, CT (US); Gregory Wesner, Bainbridge Island, WA (US)

(73) Assignee: Spoke Sciences, Inc., Seattle, WA (US)

( * ) Notice: Subject to any disclaimer, the term of this patent is extended or adjusted under 35 U.S.C. 154(b) by 809 days.

(21) Appl. No.: 17/295,405

(22) PCT Filed: Nov. 19, 2019

(86) PCT No.: PCT/US2019/062281
§ 371 (c)(1),
(2) Date: May 19, 2021

(87) PCT Pub. No.: WO2020/106767
PCT Pub. Date: May 28, 2020

(65) Prior Publication Data
US 2021/0393575 A1    Dec. 23, 2021

Related U.S. Application Data

(60) Provisional application No. 62/769,395, filed on Nov. 19, 2018.

(51) Int. Cl.
| | | |
|---|---|---|
| *A61K 31/352* | (2006.01) | |
| *A23L 33/105* | (2016.01) | |
| *A61K 9/00* | (2006.01) | |
| *A61K 9/48* | (2006.01) | |
| *A61K 31/20* | (2006.01) | |
| *A61K 36/185* | (2006.01) | |
| *A61P 43/00* | (2006.01) | |

(52) U.S. Cl.
CPC .......... *A61K 31/352* (2013.01); *A23L 33/105* (2016.08); *A61K 9/0053* (2013.01); *A61K 9/4858* (2013.01); *A61K 31/20* (2013.01); *A61K 36/185* (2013.01); *A61P 43/00* (2018.01)

(58) Field of Classification Search
CPC .. A61K 31/352; A61K 9/0053; A61K 9/4858; A61K 31/20; A61K 36/185; A61K 9/1617; A61K 31/05; A61K 31/192; A61K 31/658; A23L 33/105; A61P 43/00
USPC .......................................................... 514/454
See application file for complete search history.

(56) References Cited

U.S. PATENT DOCUMENTS

| | | |
|---|---|---|
| 2,385,365 A | 9/1945 | Link |
| 3,939,259 A | 2/1976 | Pescetti |
| 4,124,549 A | 11/1978 | Hashiudo et al. |
| 4,374,082 A | 2/1983 | Hochschild |
| 4,758,597 A | 7/1988 | Martin et al. |
| 4,902,513 A | 2/1990 | Carvais |
| 5,215,754 A | 6/1993 | Valorose et al. |
| 5,650,386 A | 7/1997 | Leone-Bay et al. |
| 5,866,536 A | 2/1999 | Leone-Bay et al. |
| 5,965,162 A | 10/1999 | Fuisz et al. |
| 6,495,177 B1 | 12/2002 | deVries et al. |
| 7,745,488 B2 | 6/2010 | Gagnon et al. |
| 8,022,048 B2 | 9/2011 | Castelli et al. |
| 8,513,300 B2 | 8/2013 | Abbas et al. |
| 9,125,833 B2 | 9/2015 | Babul |
| 9,186,412 B2 | 11/2015 | Kidron et al. |
| 10,588,974 B2 * | 3/2020 | Leone-Bay ............. A61P 25/24 |
| 11,246,852 B2 * | 2/2022 | Leone-Bay .......... A61K 9/0095 |
| 2002/0065255 A1 | 5/2002 | Bay et al. |
| 2003/0191069 A1 | 10/2003 | Inaba |
| 2004/0161819 A1 | 8/2004 | Aharoni et al. |
| 2004/0224020 A1 | 11/2004 | Schoenhard |
| 2005/0244490 A1 | 11/2005 | Otto et al. |
| 2006/0293354 A1 | 12/2006 | Eatherton |
| 2007/0072939 A1 | 3/2007 | Kupper |
| 2008/0063711 A1 | 3/2008 | Grenier et al. |
| 2008/0103139 A1 | 5/2008 | Ishizuka |
| 2008/0194676 A1 | 8/2008 | Abbas et al. |
| 2009/0155392 A1 | 6/2009 | Nelson et al. |
| 2010/0068297 A1 | 3/2010 | Naughton |
| 2010/0168066 A1 | 7/2010 | Muehlebach |
| 2011/0092583 A1 | 4/2011 | Murty et al. |
| 2011/0137040 A1 | 6/2011 | Lange |
| 2012/0237570 A1 | 9/2012 | Crain et al. |
| 2013/0040910 A1 | 2/2013 | Castelli et al. |
| 2013/0224300 A1 | 8/2013 | Maggio |

(Continued)

FOREIGN PATENT DOCUMENTS

| | | |
|---|---|---|
| CN | 101439074 A | 5/2009 |
| EP | 2286793 A2 | 2/2011 |

(Continued)

OTHER PUBLICATIONS

Wheless et al. 2019, CNS Drugs, 33: 593-604, "Pharmacokinetics and Tolerability of Multiple Doses of Pharmaceutical-Grade Synthetic Cannabidiol in Pediatric Patients with Treatment-Resistant Epilepsy" (Year: 2019).*

(Continued)

*Primary Examiner* — Jared Barsky
*Assistant Examiner* — Liyuan Mou
(74) *Attorney, Agent, or Firm* — C. Rachal Winger; Lee & Hayes PC

(57) ABSTRACT

The current disclosure provides use of N-acylated fatty amino acids to reduce absorption variability in cannabinoid-based compositions.

8 Claims, 18 Drawing Sheets

(56) References Cited

U.S. PATENT DOCUMENTS

| | | |
|---|---|---|
| 2013/0295026 A1 | 11/2013 | Viernstein et al. |
| 2014/0154317 A1 | 6/2014 | Al-Mehdar |
| 2014/0193345 A1 | 7/2014 | Levine et al. |
| 2014/0209109 A1 | 7/2014 | Larson |
| 2014/0248211 A1 | 9/2014 | Bender |
| 2014/0271842 A1 | 9/2014 | Herbig et al. |
| 2015/0050373 A1 | 2/2015 | Saklani et al. |
| 2015/0057341 A1 | 2/2015 | Perry |
| 2015/0126595 A1 | 5/2015 | Smith |
| 2015/0126754 A1 | 5/2015 | Fernandez Cid et al. |
| 2015/0132396 A1 | 5/2015 | Coulter et al. |
| 2015/0181925 A1 | 7/2015 | Turner |
| 2015/0273069 A1 | 10/2015 | Bjerregaard et al. |
| 2016/0030436 A1 | 2/2016 | Kim et al. |
| 2016/0355853 A1 | 12/2016 | Winnicki et al. |
| 2018/0263913 A1 | 9/2018 | Lefler et al. |
| 2019/0117778 A1 | 4/2019 | Leone-Bay et al. |
| 2019/0336472 A1 | 11/2019 | Leone-Bay et al. |
| 2020/0078332 A1 | 3/2020 | Leone-Bay et al. |
| 2020/0101034 A1 | 4/2020 | Leone-Bay et al. |
| 2020/0197521 A1 | 6/2020 | Leone-Bay et al. |
| 2020/0254041 A1 | 8/2020 | Leone-Bay et al. |
| 2020/0268821 A1 | 8/2020 | Leone-Bay et al. |

FOREIGN PATENT DOCUMENTS

| | | | |
|---|---|---|---|
| GB | 2377633 A | 1/2003 | |
| JP | 2016509842 A | 4/2016 | |
| WO | WO199630036 A1 | 10/1996 | |
| WO | WO9808490 A1 | 3/1998 | |
| WO | WO0032200 A1 | 6/2000 | |
| WO | WO2001019901 A2 | 3/2001 | |
| WO | WO200172286 A1 | 10/2001 | |
| WO | WO2003084518 A2 | 10/2003 | |
| WO | WO2004026857 A2 | 4/2004 | |
| WO | WO2004050011 A2 | 6/2004 | |
| WO | WO2005123051 A2 | 6/2005 | |
| WO | WO2005065661 A2 | 7/2005 | |
| WO | WO2006043260 A2 | 4/2006 | |
| WO | WO2006108692 A2 | 10/2006 | |
| WO | WO2006134523 A2 | 12/2006 | |
| WO | WO2007056242 A1 | 5/2007 | |
| WO | WO2007112399 A2 | 10/2007 | |
| WO | WO2008024408 A2 | 2/2008 | |
| WO | WO2008033024 A2 | 3/2008 | |
| WO | WO2008118414 A1 | 3/2008 | |
| WO | WO2008122967 A2 | 10/2008 | |
| WO | WO2009100245 A1 | 8/2009 | |
| WO | WO2010127033 A1 | 11/2010 | |
| WO | WO2012069591 A1 | 5/2012 | |
| WO | WO2013045115 A1 | 4/2013 | |
| WO | WO2013174854 A1 | 11/2013 | |
| WO | WO2014046983 A9 | 3/2014 | |
| WO | WO2014159688 A1 | 10/2014 | |
| WO | WO2015118549 A1 | 8/2015 | |
| WO | WO2015131269 A1 | 9/2015 | |
| WO | WO2015198078 A1 | 12/2015 | |
| WO | WO2016022936 A1 | 2/2016 | |
| WO | WO2016138505 A1 | 9/2016 | |
| WO | WO2016205923 A1 | 12/2016 | |
| WO | WO-2017185038 A1 * | 10/2017 | ........... A23L 33/105 |
| WO | WO-2018033927 A1 * | 2/2018 | ............. A61K 38/29 |
| WO | WO2018102029 A1 | 6/2018 | |
| WO | WO2018129097 A1 | 7/2018 | |
| WO | WO2018175992 | 9/2018 | |
| WO | WO2019071211 A1 | 4/2019 | |
| WO | WO2019071213 A1 | 4/2019 | |

OTHER PUBLICATIONS

Badowski et al. Cancer Chemother Pharmacol. 2017, vol. 80, pp. 441-449, "A review of oral cannabinoids and medical marijuana for the treatment of chemotherapy-induced nausea and vomiting: a focus on pharmacokinetic variability and pharmacodynamics", DOI 10. 1007/s00280-017-3387-5. (Year: 2017).*

MacCallum et al. European Journal of Internal Medicine, 2018, vol. 49, p. 12-19, "Practical considerations in medical cannabis administration and dosing". (Year: 2018).*

Bittner et al. Pharmazie, 2012, vol. 67, pp. 233-241, "Phase I clinical study to select a novel oral formulation for ibandronate containing the excipient sodium N-[8-(2-hydroxybenzoyl) amino] caprylate (SNAC)" (Year: 2012).*

Office Action Dated Mar. 16, 2021 in Japanese Application No. 2019-506612, 5 pages.

Katsuyama, et al., "Involvement of peripheral cannabinoid and opioid receptors in Beta-caryophyllene-induced antinociception," Eur. J. Pain, vol. 17, No. 5, 2013, pp. 664-675.

Kobayashi, et al., "Synthesis of Cannabidiols via Alkenylation of Cyclohexenyl Monoacetate," J. Am. Chem. Soc., vol. 8, No. 13, 2006, pp. 2699-2702.

Kremer, et al., "Pharmacokinetics, pharmacodynamics and tolerability of oral cromolyn sodium/SNAC capsules in healthy and allergic male subjects," Br. J. Clin. Pharmacol., vol. 56, 2003, pp. 467-468.

Lam, et al., "A Review on Medicinal Properties of Orientin," Adv. Pharmacol. Sci., vol. 2016, 2016, 9 pages.

Lastres-Becker, et al., "Compounds acting at the endocannabinoid and/or endovanilloid systems reduce hyperkinesia in a rat model of Huntington's disease," J. Neurochem., vol. 84, No. 5, 2003, pp. 1097-1109.

Leone-Bay, et al., "Synthesis and evaluation of compounds that facilitate the gastrointestinal absorption of heparin," J. Med. Chem., vol. 41, No. 7, 1998, pp. 1163-1171.

Linck, et al., "Effects of inhaled Linalool in anxiety, social interaction and aggressive behavior in mice," Phytomedicine, vol. 17, No. 8-9, 2002, pp. 679-683.

Lorenzetti, et al., "Myrcene mimics the peripheral analgesic activity of lemongrass tea," J. of Ethnopharmacology, vol. 34, No. 1, 1991, pp. 43-48.

Lyman, et al., "Delta 9-tetrahydrocannabinol: a novel treatment for experimental autoimmune encephalomyelitis," J. Neuroimmunol., vol. 23, No. 1, 1989, pp. 73-81.

Martyn, et al., "Nabilone in the treatment of multiple sclerosis," Lancet, vol. 345, No. 8949, 1995, p. 579.

McCartney, et al., "Safety concerns over the use of intestinal permeation enhancers: A mini-review," Tissue Barriers, vol. 4, No. 2, 2016, 14 pages.

Mechoulam, et al., "A Total Synthesis of dl-delta-Tetrahydrocannabinol, the Active Constituent of Hashish," J. Am. Chem. Soc., vol. 87, No. 14, 1965, pp. 3273-3275.

Muller, et al., "Preparation and characterization of mucus-penetrating papain/poly(acrylic acid) nanoparticles for oral drug delivery applications," Journal of Nanoparticle Research, vol. 15, 2012, pp. 1-13.

Office Action Dated Oct. 1, 2020 in Mexican Application No. MX/a/2019/006439, 4 pages.

Office Action Dated Aug. 11, 2020 in Mexican Application No. MX/a/2018/012913, 3 pages.

Office Action Dated Sep. 22, 2020 in Mexican Application No. MX/a/2019/007968, 3 pages.

Nissen, et al., "Characterization and antimicrobial activity of essential oils of industrial hemp varieties (*Cannabis sativa* L.)," Fitoterapia, vol. 81, No., 5, 2010, pp. 413-419.

Examination Report Dated Nov. 10, 2020 in New Zealand Application No. 747886, 5 pages.

Examination Report Dated Nov. 23, 2020 in New Zealand Application No. 754983, 5 pages.

Office Action Dated Oct. 29, 2020 for U.S. Appl. No. 16/805,356, 5 pages.

Office Action Dated Oct. 3, 2019 for U.S. Appl. No. 16/094,802, 5 pages.

Office Action Dated Mar. 26, 2021 in U.S. Appl. No. 16/465,984, 9 pages.

(56) References Cited

OTHER PUBLICATIONS

Oh, et al., "Effect of food on the pharmacokinetics of dronabinol oral solution versus dronabinol capsules in healthy volunteers," Clin. Pharmacol., vol. 9, 2017, pp. 9-17.
Paula-Freire, et al., "Ocimum gratissimum Essential Oil and Its Isolated Compounds (Eugenol and Myrcene) Reduce Neuropathic Pain in Mice," Planta Med., vol. 82, No. 3, 2016, pp. 211-216.
PCT Invitation to Pay Additional Fees Dated Mar. 6, 2018 in PCT Application No. PCT/US2018/012261, 2 pages.
PCT Invitation to Pay Additional Fees Dated Jun. 29, 2018 in PCT Application No. PCT/US2018/024188, 2 pages.
PCT International Preliminary Report on Patentability Dated Nov. 1, 2018 for PCT Application No. PCT/US2017/028953, 12 pages.
Search Report and Written Opinion Dated Nov. 29, 2018 for International Application No. PCT/US2018/054733, 21 pages.
Search Report and Written Opinion Dated Dec. 12, 2018 for International Application No. PCT/US2018/054728, 17 pages.
Search Report and Written Opinion Dated Dec. 28, 2017 for International Application No. PCT/US2017/055547, 11 pages.
Search Report and Written Opinion Dated Apr. 26, 2018 for International Application No. PCT/US2018/012261, 11 pages.
Seach Report and Written Opinion Dated Jul. 21, 2017 for International Application No. PCT/US17/28953, 13 pages.
Search Report and Written Opinion Dated Aug. 29, 2018 for International Application No. PCT/US2018/024188, 14 pages.
Search Report and Written Opinion Dated Feb. 3, 2020 for International Application No. PCT/US2019/062281, 8 pages.
Perry, et al., "In vitro inhibition of human erythrocyte acetylcholinesterase by Salvia lavandulaefolia essential oil and constituent terpenes," Journal of Pharmacy and Pharmacology, vol. 52, No. 7, 2010, pp. 895-902.
Petrzilka, et al., "Synthese und Chiralitat des (−)-Cannabidiols Vorlaufige Mitteilung," Helv. Chim. Acta, vol. 50, No. 2, 1967, pp. 719-723.
PubChem, "Salcaprozate Sodium," retrieved on Nov. 29, 2018 at <<https://pubchem.ncbi.nlm.nih.gov/compound/Salcaprozate sodium#/section=Information-Sources>>, Feb. 5, 2008, pp. 1-17.
Rao, et al., "Effect of myrcene on nociception in mice," J. Pharm. Pharmacol., vol. 42, No. 12, 1990, pp. 877-878.
Resstel, et al., "5-HT1A receptors are involved in the cannabidiol-induced attenuation of behavioural and cardiovascular responses to acute restraint stress in rats," Br. J. Pharmacol., vol. 156, No. 1, 2009, pp. 181-188.
Rice, et al., "Characterizing the Smell of Marijuana by Odor Impact of Volatile Compounds: An Application of Simultaneous Chemical and Sensory Analysis," PloS One, vol. 10, No. 12, 2015, pp. 1-17.
Robson, "Therapeutic aspects of cannabis and cannabinoids," Br. J. Psychiatry, vol. 178, No. 2, 2001, pp. 107-115.
Rothschild, et al., "Cannabis sativa: volatile compounds from pollen and entire male and female plants of two variants, Northern Lights and Hawaian Indica, " Botanical Journal of the Linnean Society, vol. 147, No. 4, 2005, pp. 387-397.
Salgueiro, et al., "Anxiolytic Natural and Synthetic Flavonoid Ligands of the Central Benzodiazepine Receptor Have No Effect on Memory Tasks in Rats," Pharmacol. Biochem. Behav., vol. 58, No. 4, 1997, pp. 887-891.
Schaeffer, "5 Supplements That Can Treat Migraines," retrieved at <<https://www.healthline.com/health/migraine/migraine-vitamins#1>>, Healthline, Mar. 24, 2016, 11 pages.
European Office Action mailed Oct. 20, 2022 for European Patent Application No. 21175803.2, a foreign counterpart to U.S. Pat. No. 10,588,974, 5 pages.
Extended European Search Report mailed Nov. 14, 2022, for European Patent Application No. 19886986.9, 8 pages.
Final Office Action Dated Jul. 19, 2022 in U.S. Appl. No. 16/753,721, 15 pages.
Office Action Dated Mar. 8, 2022 in Japanese Application No. 2019-536222, 4 pages.
Office Action Dated Mar. 9, 2022 in Chinese Application No. 201780075150.0, 9 pages.

"Cannabis (Marijuana) and Cannabinoids: What You Need to Know." National Center for Complementary and Integrative Health, U.S. Department of Health and Human Services, 2019, https://www.nccih.nih.gov/health/cannabis-marijuana-and-cannabinoids-what-you-need-to-know. Retrieved Nov. 29, 2021.
Office Action Dated Oct. 19, 2021 in Japanese Application No. 2019-536222, 4 pages.
Office Action Dated Oct. 20, 2021 for Mexican Application No. MX/a/2019/007968, 4 pages.
Office Action Dated Nov. 29, 2021 in U.S. Appl. No. 16/753,721, 10 pages.
Office Action Dated Dec. 7, 2021 in U.S. Appl. No. 16/474,480, 14 pages.
Search Report Dated Nov. 25, 2021 in European Application No. 21175803.2, 6 pages.
Baker and Pryce, "The therapeutic potential of cannabis in multiple sclerosis," Expert Opin. Investig. Drugs, vol. 12, No. 4, 2003, pp. 561-567.
Basavarajappa and Hungund, "Role of the endocannabinoid system in the development of tolerance to alcohol," Alcohol Alcohol., vol. 40, No. 1, 2005, pp. 15-24.
Burstein and Zurier "Cannabinoids, endocannabinoids, and related analogs in inflammation," AAPS J., vol. 11, No. 1, 2009, pp. 109-119.
Burstein, "Cannabidiol (CBD) and its analogs: a review of their effects on inflammation," Bioorg. Med. Chem., vol. 23, 2015, pp. 1377-1385.
Choudhary, et al., "Development and characterization of an atorvastatin solid dispersion formula using skimmed milk for improved oral bioavailability," Acta Pharmaceutica Sinica B, vol. 2, No. 4, 2012, pp. 421-428.
Office Action Dated Jun. 14, 2021 in European Application No. 17875117.2, 5 pages.
Extended European Search Report Dated Jul. 29, 2021 for European Application No. 18865203.6, 15 pages.
Gaffal, et al., "Anti-inflammatory activity of topical THC in DNFB-mediated mouse allergic contact dermatitis Independent of CB1 and CB2 receptors," Allergy, vol. 68, No. 8, 2013, pp. 994-1000.
Heckelman, et al, The Merck Index: an encyclopedia of chemicals, drugs, and biologicals, (No. 615.11 MER), p. 146.
Huestis, "Human Cannabinoid Pharmacokinetics," Chem. Biodivers., vol. 4, No. 8, 2007, pp. 1770-1804.
Office Action Dated Sep. 14, 2021 in Japanese Application No. 2019-529537, 7 pages.
Kim & Yoon, "Rapid screening for acidic non-steroidal anti-inflammatory drugs in urine by gas chromatography-mass spectrometry in the selected-ion monitoring mode," J. Chromatogr. B. Biomed Appl., vol. 682, No. 1, 1996, pp. 55-66.
Office Action Dated Sep. 30, 2021 in Korean Application No. 10-2018-7033084, 10 pages.
Maher, et al., "Intestinal permeation enhancers for oral peptide delivery," Adv. Drug Del. Rev., vol. 106, 2016, pp. 277-319.
O'Connell and Bov-Matar, "Long term marijuana users seeking medical cannabis in California (2001-2007): demographics, social characteristics, patterns of cannabis and other drug use of 4117 applicants," Harm Reduct. J., vol. 4, 2007, 7 pages.
Final Office Action Dated Jul. 27, 2021 in U.S. Appl. No. 16/474,480, 15 pages.
Ohlsson, et al. "Plasma delta-9 tetrahydrocannabinol concentrations and clinical effects after oral and intravenous administration and smoking," Clin. Pharmacol. Ther., vol. 28, No. 3, 1980, pp. 409-416.
Peana, et al., "Anti-inflammatory activity of linalool and linalyl acetate constituents of essential oils," Phytomedicine, vol. 9, 2002, pp. 721-726.
Peana, et al., "Linalool produces antinociception in two experimental models of pain," Euro. Jour. Pharm., vol. 460, No. 1, 2003, pp. 37-41.
Perez-Reyes, et al., "Pharmacology of orally administered delta-9-tetrahydrocannabinol," Clin Pharmacol Ther., vol. 14, No. 1, 1973, pp. 48-55.

(56) References Cited

OTHER PUBLICATIONS

Raman, et al., "Amyotrophic lateral sclerosis: delayed disease progression in mice by treatment with a cannabinoid," Amyotroph Lateral Scler. Other Motor Neuron Disord., vol. 5, No., 1, 2004, pp. 33-39.

Russo, "Taming THC: potential cannabis synergy and phytocannabinoid-terpenoid entourage effects," BJP, vol. 163, 2011, pp. 1344-1364.

Russo, et al., "A tale of two cannabinoids: the therapeutic rationale for combining tetrahydrocannabinol and cannabidiol," Med. Hypotheses, vol. 66, No. 2, 2006, pp. 234-246.

Shoba, et al. "Influence of piperine on the pharmacokinetics of curcumin in animals and human volunteers," Planta Med, vol. 64, No. 4, 1998, pp. 353-356.

Zanelati, et al., "Antidepressant-like effects of cannabidiol in mice: possible involvement of 5-HT1A receptors," Br. J. Pharmacol., vol. 159, No. 1, 2010, pp. 122-128.

Shohami, et al., "Endocannabinoids and traumatic brain injury," Br. J. Pharmacol., vol. 163, No. 7, 2011, pp. 1402-1410.

Sieradzan, et al., "Cannabinoids reduce levodopa-induced dyskinesia in Parkinson's disease: a pilot study," Neurology, vol. 57, No. 11, 2001, pp. 2108-2111.

Souto-Maior, et al., "Anxiolytic-like effects of inhaled linalool oxide in experimental mouse anxiety models," Pharmacol. Biochem. Behav., vol. 100, No. 2, 2011, pp. 259-263.

Syed, et al., "Delta-9-Tetrahydrocannabinol/Cannabidiol (Sativex) A Review of Its Use in Patients with Moderate to Severe Spasticity Due to Multiple Sclerosis," Drugs, vol. 74, No. 5, 2014, pp. 563-578.

Tarapore, et al., "The dietary terpene lupeol targets colorectal cancer cells with constitutively active Wnt/beta-catenin signaling," Molecular Nutrition and Food Research, vol. 57, No. 11, 2013, pp. 1950-1958.

Tashkin, et al., "Effects of smoked marijuana in experimentally induced asthma," Am. Rev. Respir. Dis., vol. 112, No. 3, 1975, pp. 377-386.

Victorio, et al., "Flavonoid extraction from Alpinia zerumbet (Pers.) Burttet Smith leaves using different techniques and solvents," Ecl. Quinn., vol. 34, No. 1, 2009, pp. 19-24.

Vuolo, et al., "Evaluation of Serum Cytokines Levels and the Role of Cannabidiol Treatment in Animal Model of Asthma," Mediators of Inflammation, vol. 2015, No. 538670, 5 pages.

Walsh, et al., "Acute administration of cannabidiol in vivo suppresses ischaemia-induced cardiac arrhythmias and reduces infarct size when given at reperfusion," Br. J. Pharmacol., vol. 160, No. 5, 2010, pp. 1234-1242.

Wheless, et al., "Pharmacokinetics and Tolerability of Multiple Doses of Pharmaceutical-Grade Synthetic Cannabidiol in Pediatric Patients With Treatment-Resistant Epilepsy," CNS Drugs, vol. 33, No. 6, 2019, pp. 593-604.

Yadav, et al., "Effect of Cyclodextrin Complexation of Curcumin on its Solubility and Antiangiogenic and Anti-inflammatory Activity in Rat Colitis Model," AAPS Pharm. Sci. Tech. vol. 10, No. 3, 2009, 11 pages.

Abramovici, "Information for Health Care Providers Cannabis and the Cannabinoids," Health Canada, 2013, 158 pages.

Aungst, et al., "Absorption Enhancers: Applications and Advances", The AAPS Journal, vol. 14, No. 1, 2012, 9 pages.

Bab, et al., "Cannabinoids and the skeleton: from marijuana to reversal of bone loss," Ann. Med., vol. 41, No. 8, 2009, pp. 560-567.

Babaee, et al., "Antioxidant capacity of calendula officinalis flowers extract and prevention of radiation induced propharyngeal mucositis in patients with head and neck cancers: a randomized controlled clinical study," Journal of Pharmaceutical Sciences, vol. 21, No. 18, 2013, pp. 1-7.

Bahi, et al., "Beta—Caryophyllene, a CB2 receptor agonist produces multiple behavioral changes relevant to anxiety and depression in mice," Physiol. Behav., vol. 135, 2014, pp. 119-124.

Barrett, et al., "Cannflavin A and B, prenylated flavones from Cannabis sativa L.," Experientia, vol. 42, No. 4, 1986, pp. 452-453.

Baughman, et al., "Oral delivery of anticoagulant doses of heparin. A randomized, double-blind, controlled study in humans," Circulation, vol. 98, No. 16, 1998, pp. 1610-1615.

Beal, et al., "Dronabinol as a treatment for anorexia associated with weight loss in patients with Aids," J. Pain. Symptom Manage., vol. 10, No. 2, 1995, pp. 89-97.

Binet, et al., "Pharmacodynamic properties (sedative action and spasmolytic action) of several aliphatic terpene alcohols," Ann. Pharm. Fr., vol. 30, No. 9, 1972, pp. 611-616.

Biro, et al., "The endocannabinoid system of the skin in health and disease: novel perspectives and therapeutic opportunities," Trends Pharmacol. Sci., vol. 30, No. 8, 2009, pp. 411-420.

Bittner, et al., "Phase I clinical study to select a novel oral formulation for ibandronate containing the excipient sodium N-[8-(2-hydroxybenzoyl) amino] caprylate (SNAC)", Pharmazie, vol. 67, 2012, pp. 233-241.

Brenneisen, "Chemistry and Analysis of Phytocannabinoids and Other Cannabis Constituents," Humana Press Inc., Totowa, New Jersey, 2007, pp. 17-49.

Calderon-Montano, et al., "A Review on the Dietary Flavonoid Kaempferol," Mini. Rev. Med. Chem., vol. 11, No. 4, 2011, pp. 298-344.

Campos, et al., "Cannabidiol, neuroprotection and neuropsychiatric disorders," Pharmacol. Res., vol. 112, 2016, pp. 119-127.

Cardi, et al., "Superiority of Laparoscopy Compared to Ultrasonography in Diagnosis of Widespread Liver Diseases," Dig. Dis. Sci., vol. 42, No. 3, 1997, pp. 546-547.

Castelli, et al., "Comparing the Efficacy and Tolerability of a New Daily Oral Vitamin B12 Formulation and Intermittent Intramuscular Vitamin B12 in Normalizing Low Cobalamin Levels: A Randomized, Open-Label, Parallel-Group Study," Clin. Ther., vol. 33, No. 3, 2011, pp. 358-371.

Castelli, et al., "Pharmacokinetics of Oral Cyanocobalamin Formulated with Sodium N-[8-(2-hydroxybenzoyl)amino] caprylate (SNAC): An Open-Label, Randomized, Single-DOSE, Parallel-Group Study in Healthy Male Subjects," Clinical Terapeutics, vol. 33, No. 7, 2011, pp. 934-945.

Office Action Dated Oct. 30, 2020 in Chilean Application No. 201901471, 15 pages.

Office Action Dated Jul. 31, 2020 in Chilean Application No. 201802997, 11 pages.

Office Action Dated Sep. 14, 2020 in Chilean Application No. 201901832, 12 pages.

Office Action Dated Apr. 20, 2021 in Chinese Application No. 201780024997.6, 6 pages.

Office Action Dated Sep. 2, 2020 in Chinese Application No. 201780024997.6, 9 pages.

Office Action Dated Dec. 9, 2020 in Colombian Application No. NC2018/0011299, 11 pages.

Office Action Dated Apr. 30, 2020 in Colombian Patent Application No. NC2018/0011299, 8 pages.

De Vries, et al., "Cannabinoid modulation of the reinforcing and motivational properties of heroin and heroin-associated cues in rats," Psychopharmacology [Berl], vol. 168, No. 1-2, 2003, pp. 164-169.

Ding, et al., "Oral Absorption Enhancement of Cromolyn Sodium Through Noncovalent Complexation," Pharmaceutical Research, vol. 21, No. 12, 2004, pp. 2196-2206.

Office Action Dated Nov. 12, 2019 in Eurasian Application No. 201892396, 6 pages.

Office Action Dated Sep. 15, 2020 in European Application No. 17786760.3, 4 pages.

Partial Search Report Dated Apr. 28, 2021 in European Application No. 18865203.6, 16 pages.

Extended European Search Report Dated Jun. 15, 2020 in European Patent Application No. 17875177.2, 7 pages.

Extended European Search Report Dated Oct. 17, 2019 for European Patent Application No. 17786760.3, 7 pages.

Extended European Search Report Dated Nov. 27, 2020 in European Application No. 18770819.3, 9 pages.

Extended European Search Report Dated Jul. 9, 2020 in European Application No. 18736204.1, 10 pages.

(56) References Cited

OTHER PUBLICATIONS

Epps, et al., "Synergistic Endo- and Exo-Interactions Between Blueberry Phenolic Compounds, Grape Variety Fractions, Chocolate Covered Strawberries, and Fruit Smoothies," J. of Food Res., vol. 2, No. 6, 2013, pp. 33-47.

Eubanks, et al., "A molecular link between the active component of marijuana and Alzheimer's disease pathology," Mol. Pharm., vol. 3, No. 6, 2006, pp. 773-777.

Falk, et al., "Uptake, distribution and elimination of alpha-pinene in man after exposure by inhalation," Scand. J. Work Environ. Health, vol. 16, No. 5, 1990, pp. 372-378.

Florence, "The Oral Absorption of Micro- and Nanoparticulates: Neither Exceptional Nor Unusual," Pharm. Res., vol. 14, No. 3, 1997, pp. 259-266.

Gertsch, et al., "Beta-caryophyllene is a dietary cannabinoid," PNAS, vol. 105, No. 26, 2008, pp. 9099-9104.

Gil, et al., "Comparative study of different essential oils of Bupleurum gibraltaricum Lamarck," Pharmazie, vol. 44, No. 4, 1989, pp. 284-287.

Grivennikov et al., "Immunity, Inflammation, and Cancer", Cell, vol. 140, No. 6, 2010, pp. 883-899.

Grotenhermen, et al., "The Therapeutic Potential of Cannabis and Cannabinoids," Dtsch Arztebl Int., vol. 109, No. 29-30, 2012, pp. 495-501.

Guimaraes-Santos, et al., "Copaiba Oil-Resin Treatment Is Neuroprotective and Reduces Neutrophil Recruitment and Microglia Activation after Motor Cortex Excitotoxic Injury," J. Evid. Based Complementary Altern. Med., vol. 2012, 2012, pp. 1-9.

Guindon and Hohmann, "The endocannabinoid system and cancer: therapeutic implication," Br. J. Pharmacol., vol. 163, No. 7, 2011, pp. 1447-1463.

Guzman, "Cannabinoids: Potential Anticancer Agents," Nat. Rev. Cancer, vol. 3, 2003, pp. 745-755.

Hess, et al., "Investigation of the Enhancing Mechanism of Sodium N-[8-(2-hydroxybenzoyl)amino]caprylate effect of the Intestinal Permeability of Polar Molecules Utilizing a Voltage Clamp Method", Departement of Pharmaceutics, European Journal of Pharmaceutical Science 25, 2005, pp. 307-312.

Holdcroft, et al., "Clinical Trial Experience with Cannabinoids," Pharm. Sci., vol. 3, 1997, pp. 546-550.

Office Action Dated Dec. 31, 2020 in Israel Application No. 262505, 4 pages.

* cited by examiner

| Name | Structure | Name | Structure |
|---|---|---|---|
| CBC | 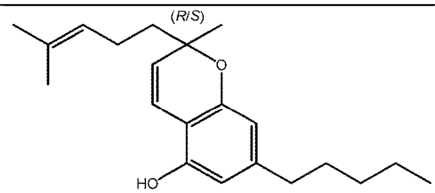 | CBN | 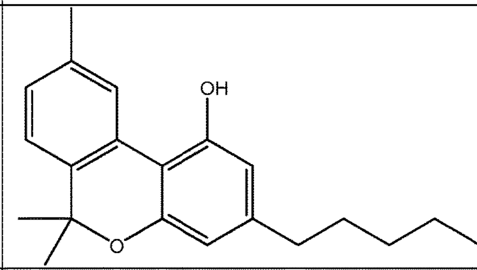 |
| CBCV | 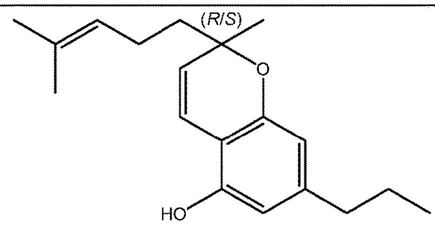 | CBNV | 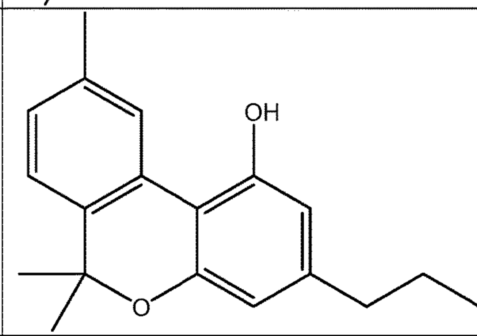 |
| CBD | 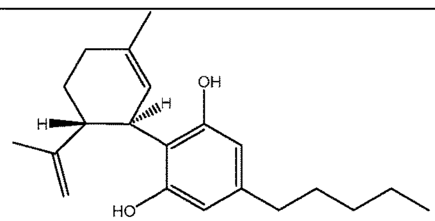 | CBO | 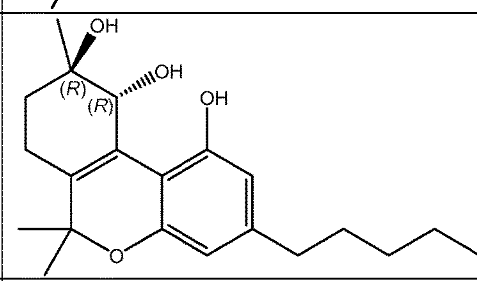 |
| CBDA | 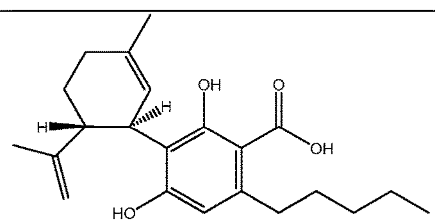 | THC | 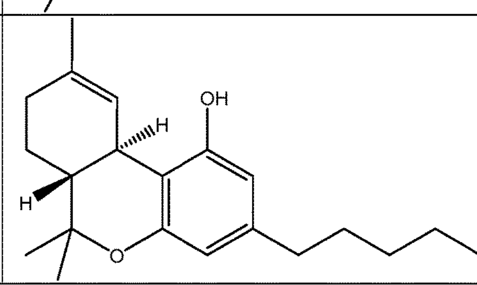 |

FIG. 1A (cont'd)

| Name | Structure | Name | Structure |
|---|---|---|---|
| CBDV | 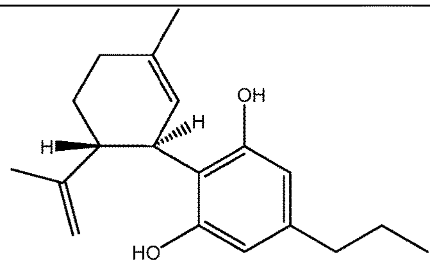 | THCA | 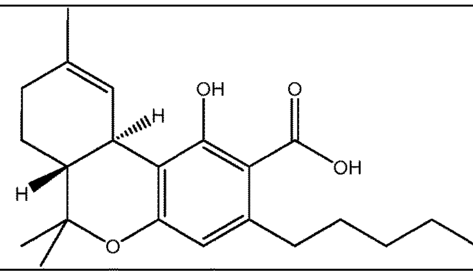 |
| CBG | 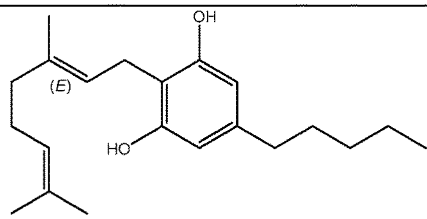 | THCV | 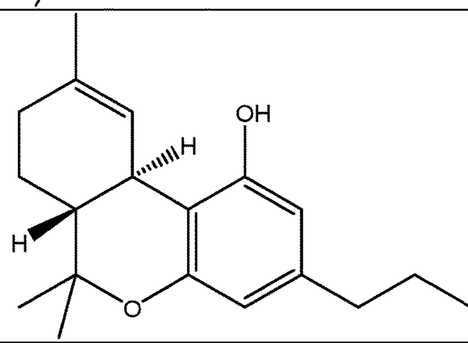 |
| CBGV | 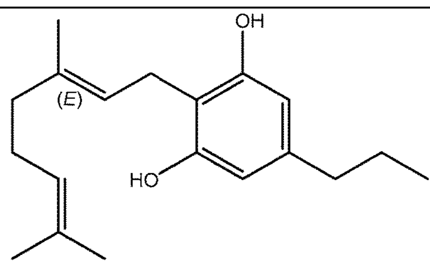 | THCVA | 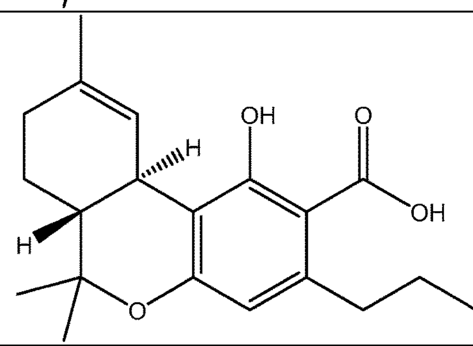 |
| CBL | 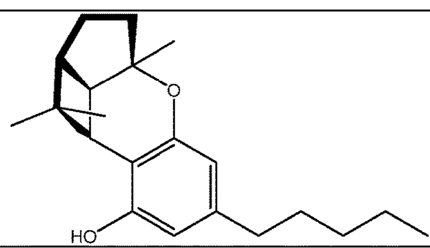 | | |

| # | Structure |
|---|---|
| THC | 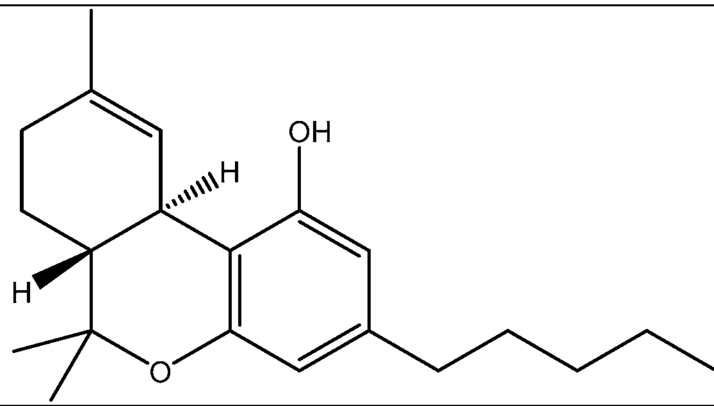 |
| CBD | 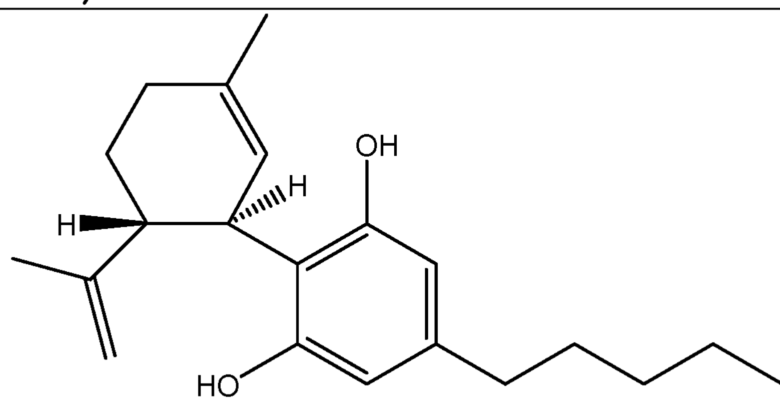 |
| CBDV | 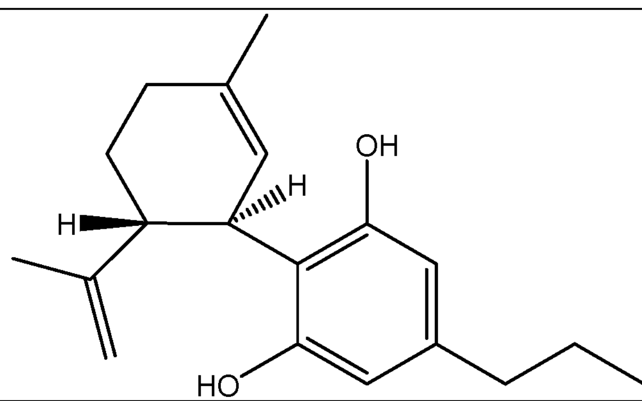 |

| # | Structure |
|---|---|
| Nabilone | 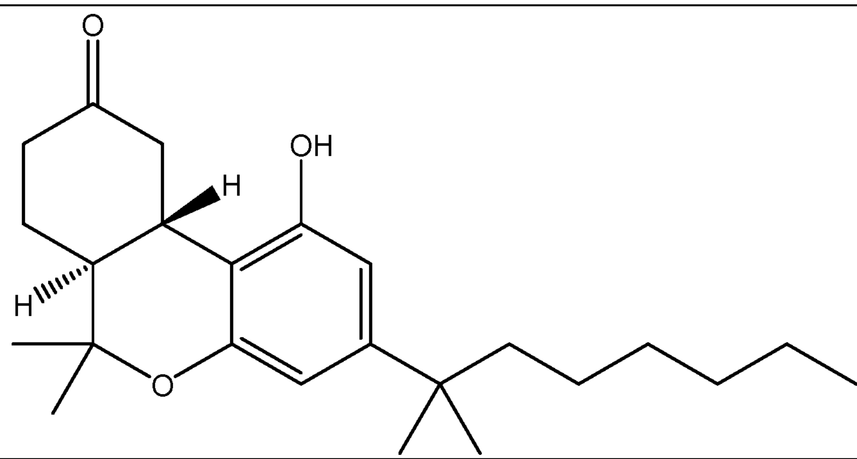 |
| 7-OH-CBD | 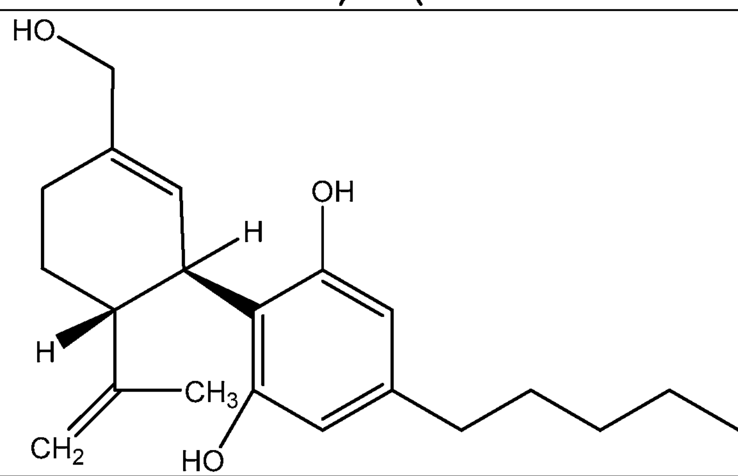 |

| # | Structure |
|---|---|
| 7-OH-CBDV | 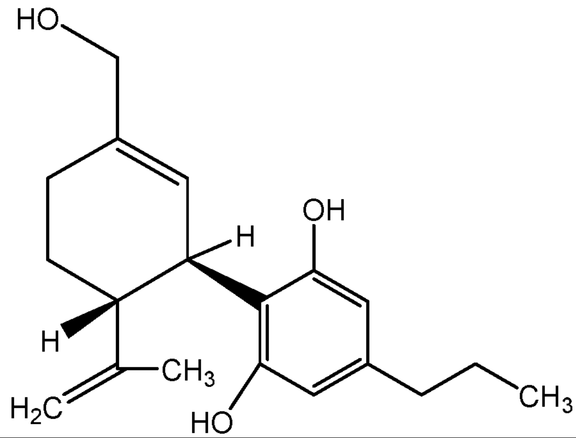 |
| (I) | 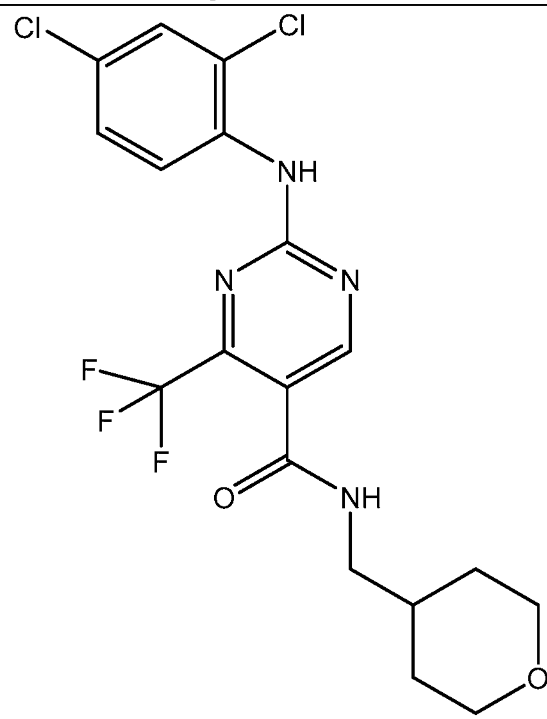 |
| (II) | 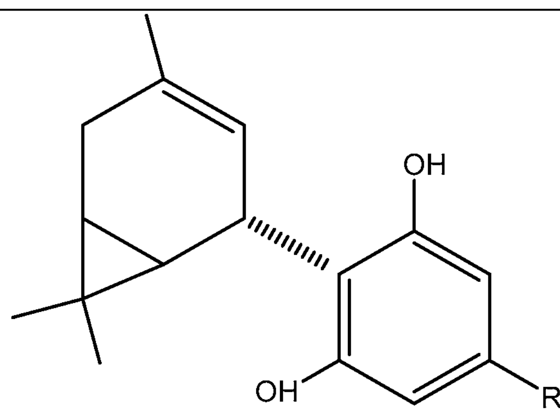 |

FIG. 1B (cont'd)

| # | Structure |
|---|---|
| (III) | 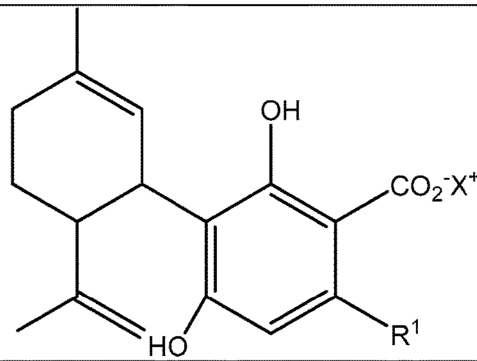 |
| (IV) | 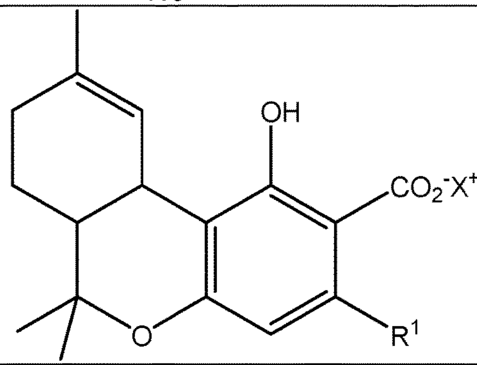 |
| (V) | 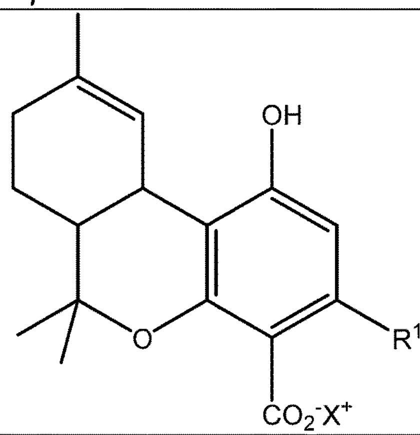 |
| (VI) | 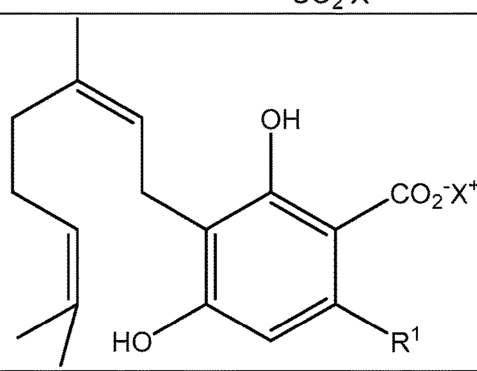 |

| # | Structure |
|---|---|
| (VII) | 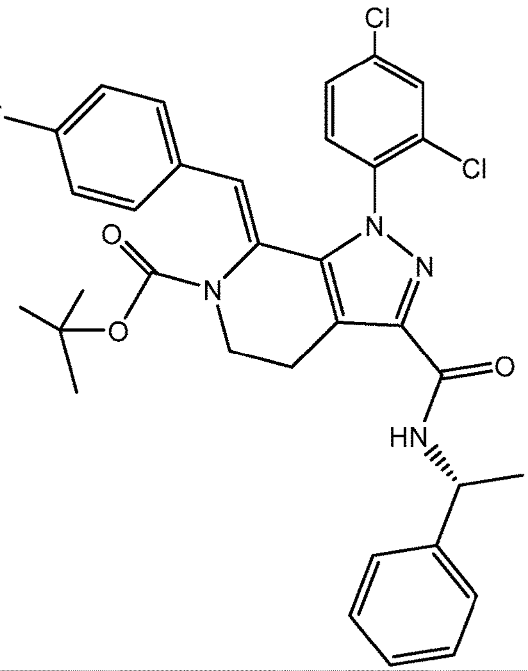 |
| (VIII) | 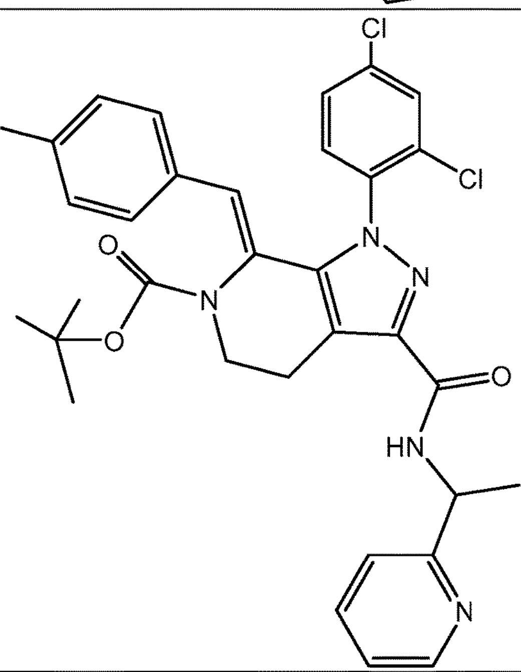 |

| # | Structure |
|---|---|
| (IX) | 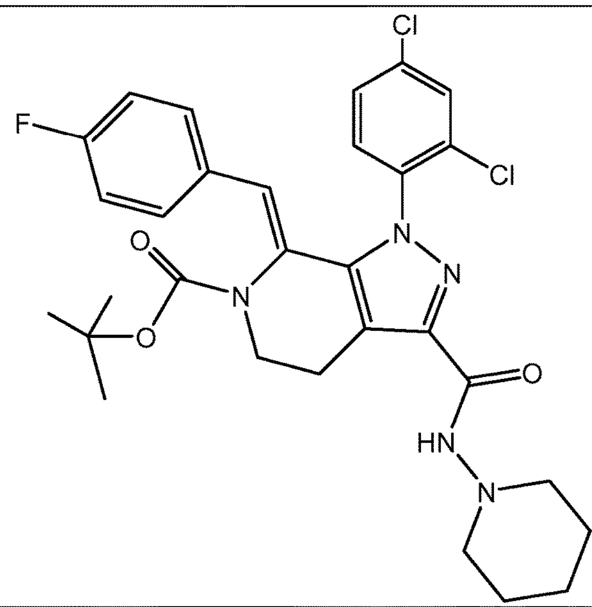 |

| # | Structure |
|---|---|
| (X) | 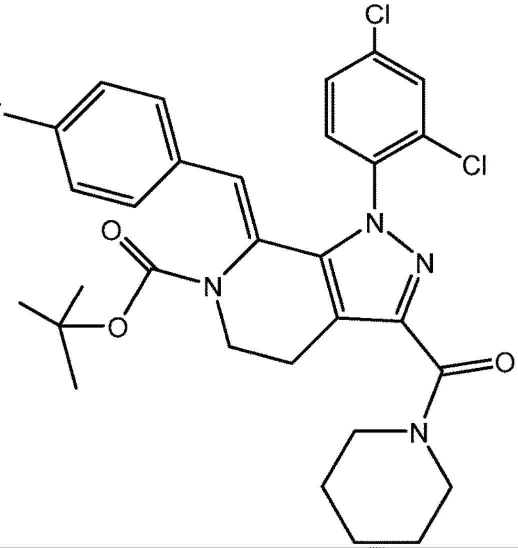 |
| (XI) | 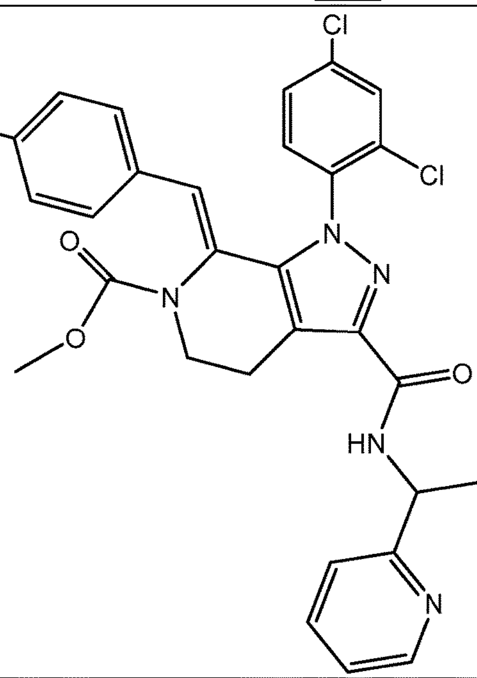 |

| # | Structure |
|---|---|
| (XII) | 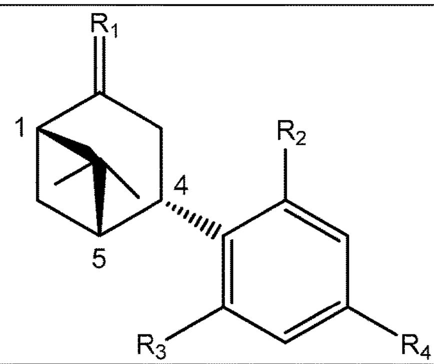 |

| # | Structure |
|---|---|
| (XIII) | 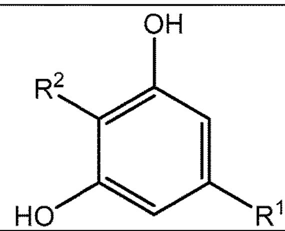 |
| (XIV) | 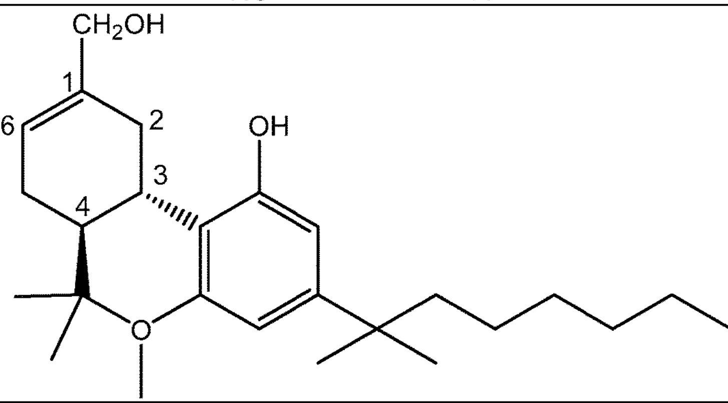 |
| (XV) | 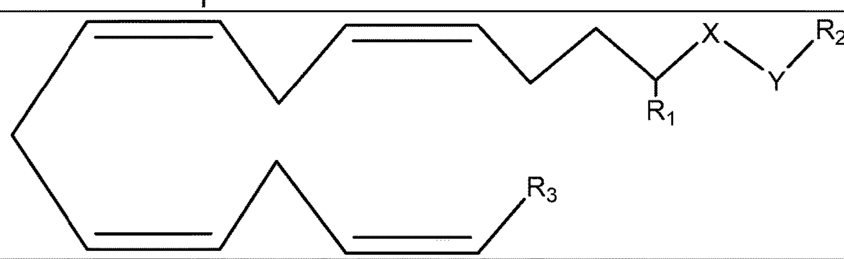 |
| (XVI) | 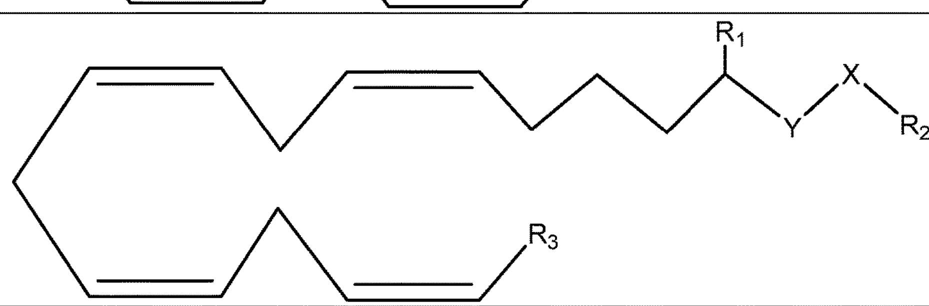 |

| # | Structure |
|---|---|
| I | 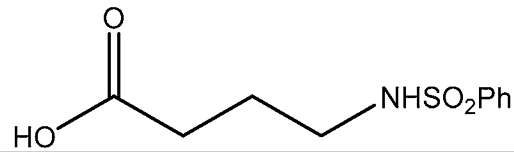 |
| II | 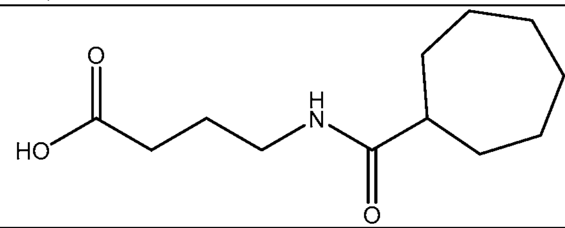 |
| III | 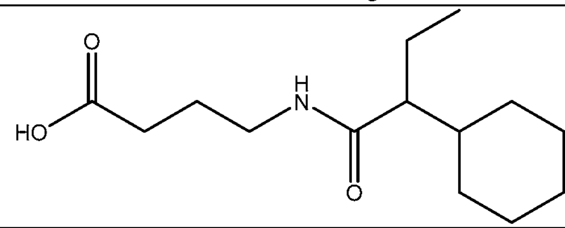 |
| IV | 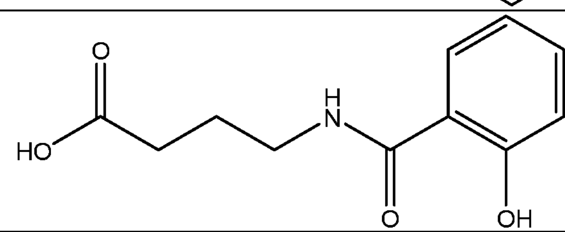 |
| V | 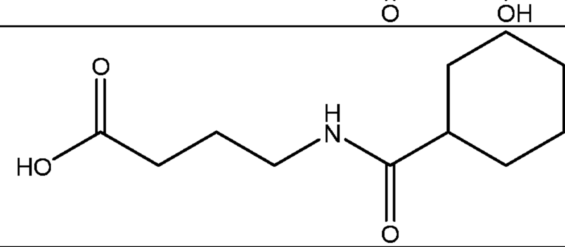 |
| VI | 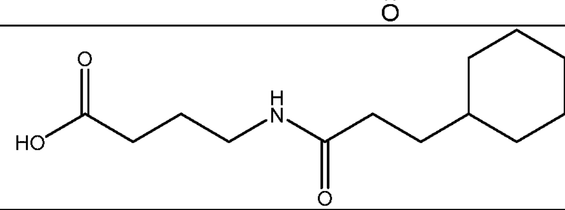 |
| VII | 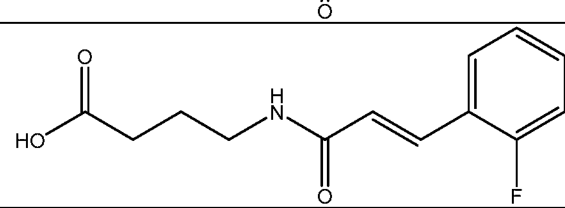 |
| VIII | 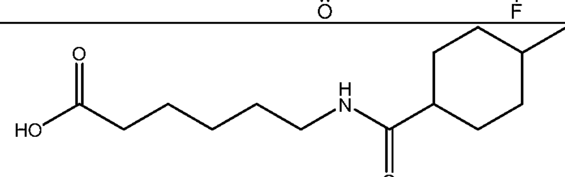 |

FIG. 2 (cont'd)

| # | Structure |
|---|---|
| IX | 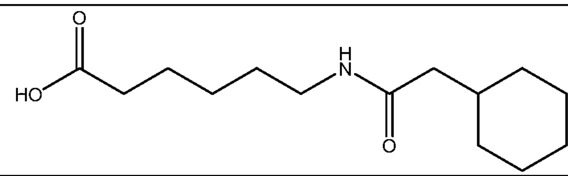 |
| X | 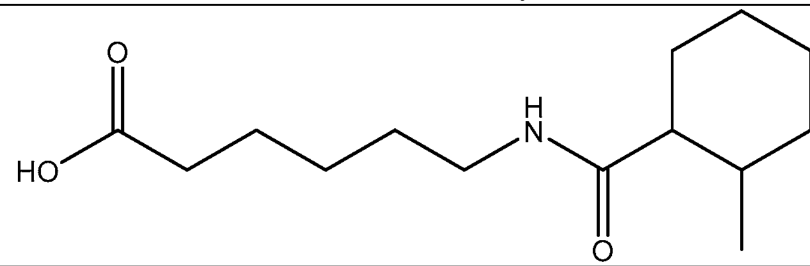 |
| XI | 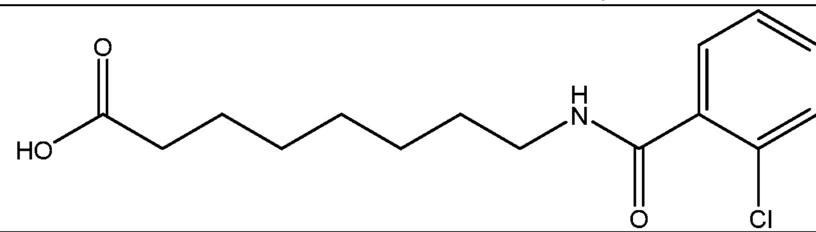 |
| XII | 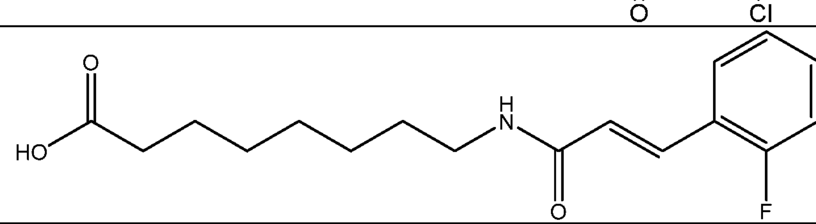 |
| XIII | 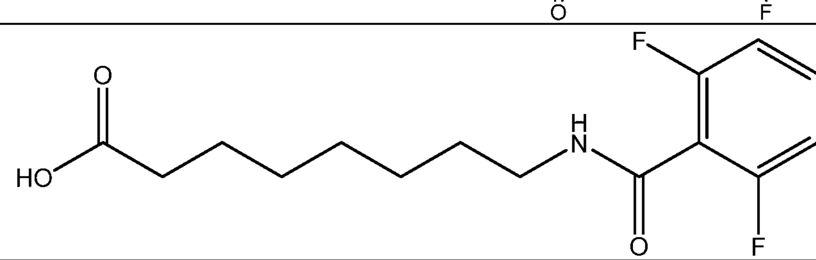 |
| XIV | 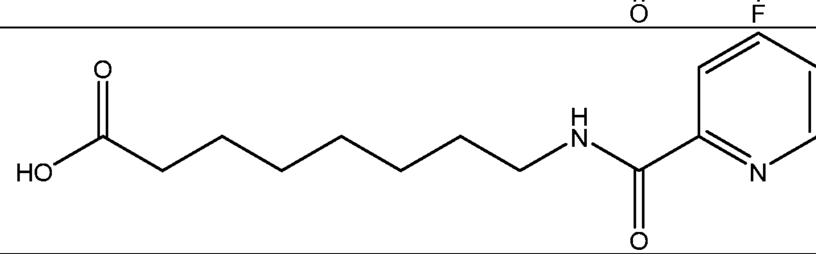 |
| XV | 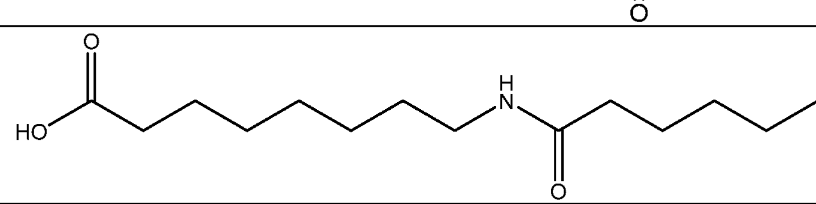 |

| # | Structure |
|---|---|
| XVI | 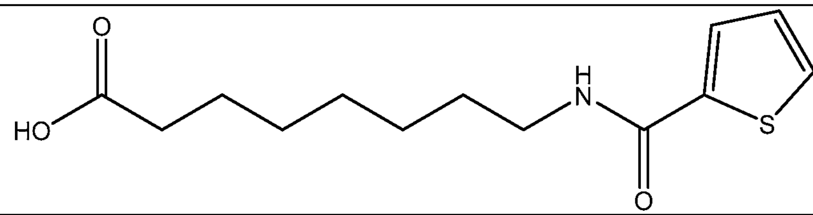 |
| XVII | 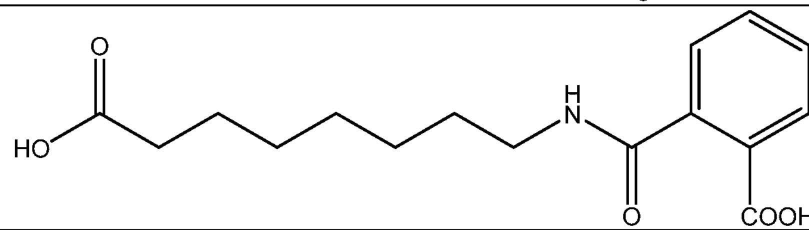 |
| XVIII | 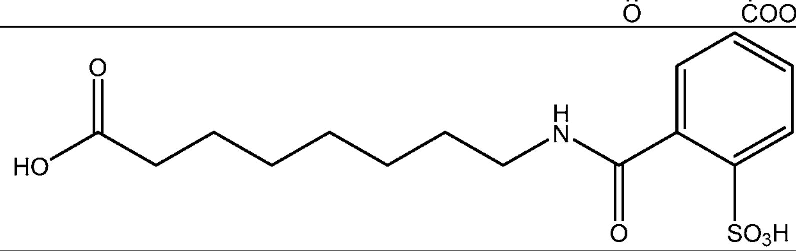 |
| XIX | 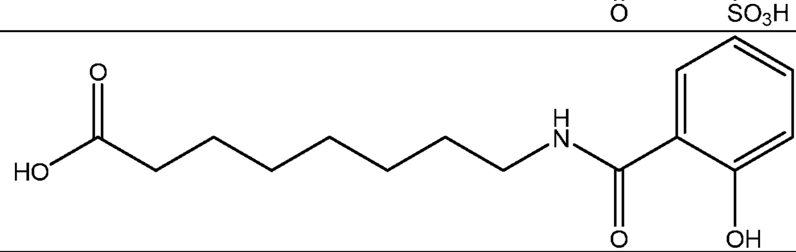 |
| XX | 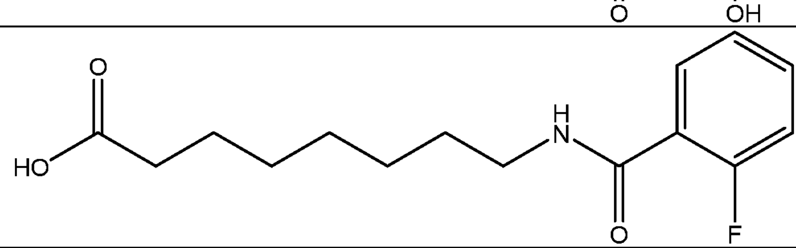 |
| XXI | 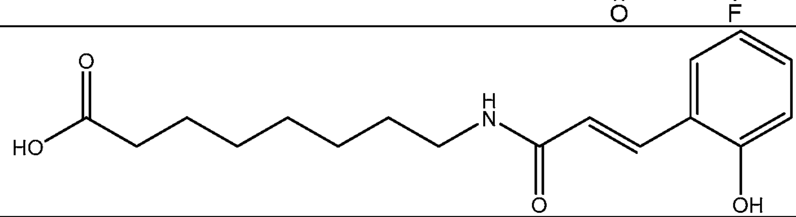 |
| XXII | 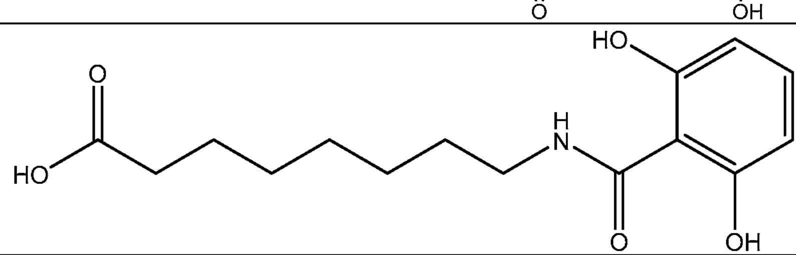 |

| # | Structure |
|---|---|
| XXIII | 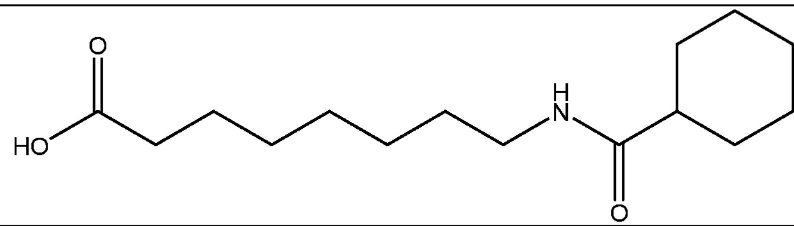 |
| XXIV | 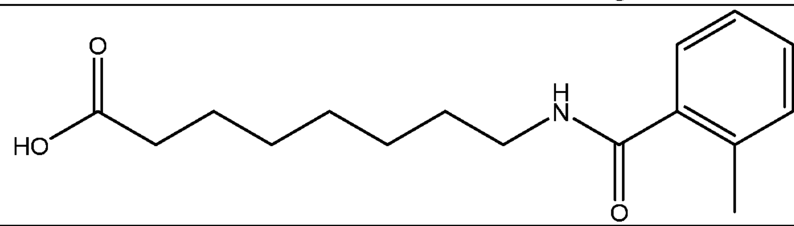 |
| XXV | 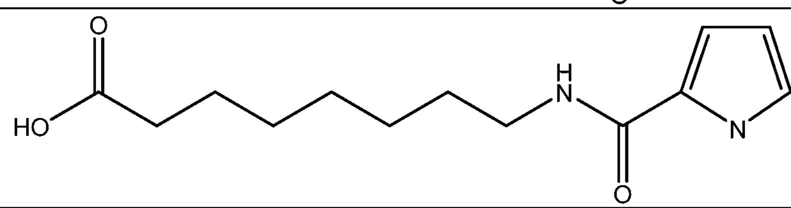 |
| XXVI | 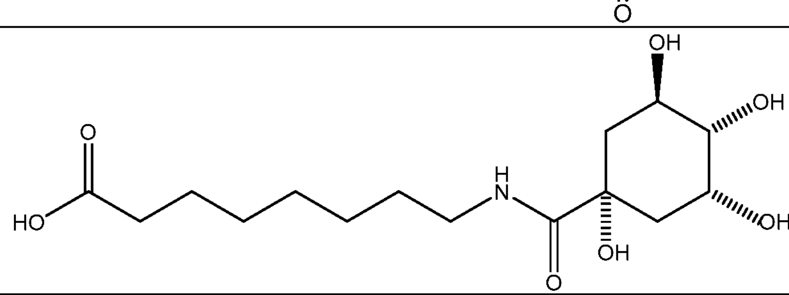 |
| XXVII | 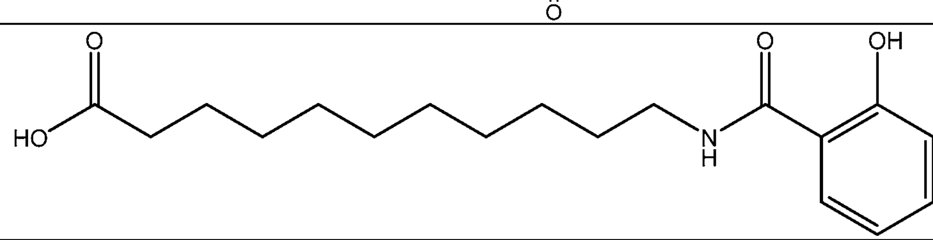 |
| XXVIII | 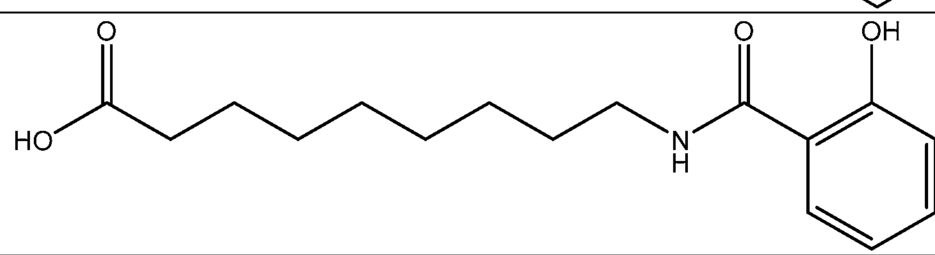 |

FIG. 2 (cont'd)

| # | Structure |
|---|---|
| XXIX | HOOC-(CH$_2$)$_5$-NH-C(=O)-C$_6$H$_4$-OH (6-[(2-hydroxybenzoyl)amino]hexanoic acid) |
| XXX | HOOC-(CH$_2$)$_{10}$-NH-C(=O)-C$_6$H$_4$-OH (11-[(2-hydroxybenzoyl)amino]undecanoic acid) |
| XXXI | HOOC-(CH$_2$)$_5$-NH-C(=O)-cyclohexyl |
| XXXII | HOOC-(CH$_2$)$_5$-NHSO$_2$Ph |
| XXXIII | HOOC-(CH$_2$)$_5$-NH-C(=O)-CH$_2$-Ph |
| XXXIV | HOOC-(CH$_2$)$_5$-NH-C(=O)-C$_6$H$_4$-OH |
| XXXV | HOOC-(CH$_2$)$_7$-NHSO$_2$Ph |

FIG. 3

| # | Structure | # | Structure |
|---|---|---|---|
| a | R₁–C(=O)–N(R₂)–CH(CH₃)–C(=O)–OR₃ (alanine ester) | j | R₁–C(=O)–N(R₂)–CH(CH₂CH₂SCH₃)–C(=O)–OR₃ (methionine ester) |
| b | R₁–C(=O)–N(R₂)–CH(CH₂C(=O)NH₂)–C(=O)–OR₃ (asparagine ester) | k | R₁–C(=O)–N(R₂)–CH(CH₂–C₆H₅)–C(=O)–OR₃ (phenylalanine ester) |
| c | R₁–C(=O)–N(R₂)–CH(CH₂COO⁻ Na⁺)–C(=O)–OR₃ (aspartate ester) | l | R₁–C(=O)–N(pyrrolidine)–C(=O)–OR₃ (proline ester) |
| d | R₁–C(=O)–N(R₂)–CH(CH₂SH)–C(=O)–OR₃ (cysteine ester) | m | R₁–C(=O)–N(R₂)–CH(CH₂–O–C(=O)–OR₃)–... (serine diester) |
| e | R₁–C(=O)–N(R₂)–CH(CH₂CH₂COO⁻ Na⁺)–C(=O)–OR₃ (glutamate ester) | n | R₁–C(=O)–N(R₂)–CH(CH(CH₃)–O–C(=O)–OR₃)–... (threonine diester) |

| # | Structure | # | Structure |
|---|---|---|---|
| f | 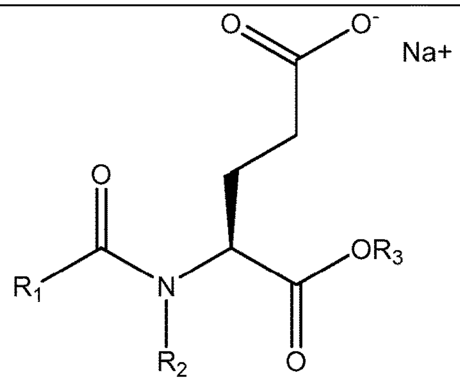 | o | 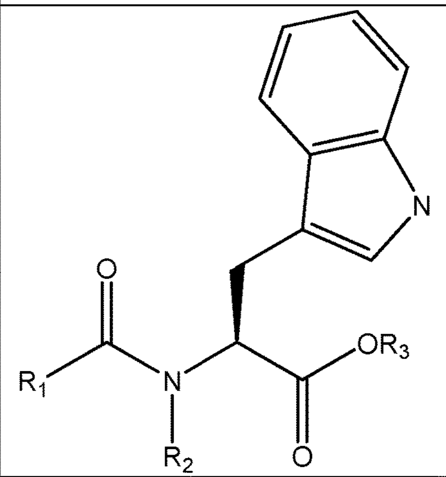 |
| g | 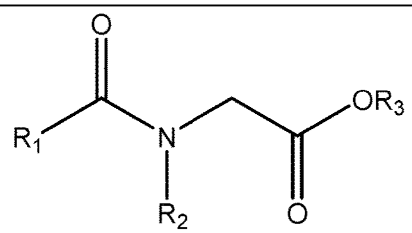 | p | 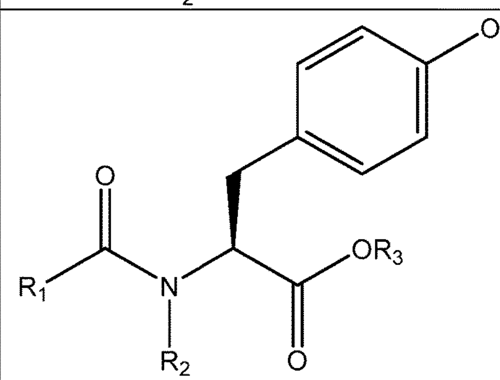 |
| h | 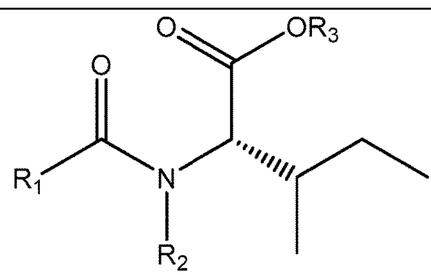 | q | 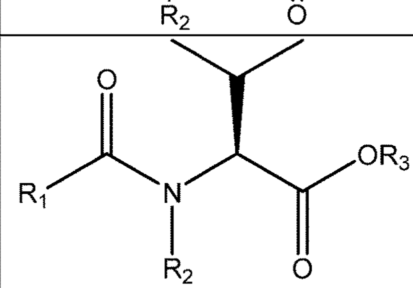 |
| i | 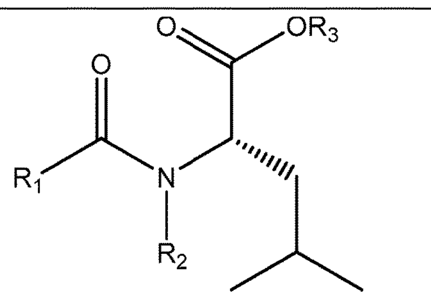 | r | 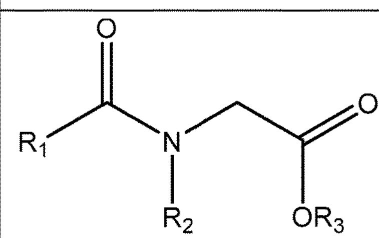 |

N-ACYLATED FATTY AMINO ACIDS TO REDUCE ABSORPTION VARIABILITY IN CANNABINOID BASED COMPOSITIONS

CROSS-REFERENCE TO RELATED APPLICATIONS

This application is a U.S. National Phase Application based on International Patent Application No. PCT/US2019/062281, filed on Nov. 19, 2019, which claims priority to U.S. Provisional Patent Application No. 62/769,395 filed Nov. 19, 2018, each of which is incorporated herein by reference in its entirety as if fully set forth herein.

FIELD OF THE DISCLOSURE

The current disclosure provides use of N-acylated fatty amino acids to reduce absorption variability in cannabinoid-based compositions.

BACKGROUND OF THE DISCLOSURE

Oral cannabinoid administration is generally characterized by wide variability in absorption within the same person from dose to dose (intrasubject variability). This variability is a long-standing issue, having been discussed in, for example, Wheless et al., CNS Drugs (2019) 33: 593-604; Oh et al., Clinical Pharmacology: Advances and Applications (2017) 9: 9-17; Huestis, Chem Biodivers. (2007) 4(8): 1770-1804; Kim & Yoon, J. Chromatogr., Sect. B. (1996) 682: 55; Ohlsson et al. Clin. Pharmacol. Ther. (1980) 28: 409; and Perez-Reyes et al., Clin. Pharmacol. Ther. (1973)14: 48. For example, Wheless et al. describes that in pediatric epilepsy patients the coefficient of variation (% CV) associated with absorption ranges from 103% CV-135% CV (see Table 3). Oh et al. describes that in healthy volunteers who have fasted before ingesting an oral cannabinoid formulation (as in the current disclosure) the coefficient of variation (% CV) associated with absorption was 58% CV-60% CV (see Table 1, last 2 columns). This variability is undesirable because it makes the prescription of specific doses difficult, and in some cases, impossible. The consequences of this dosing conundrum can be severe over- or under-dosing patients in the treatment of disease. While the variability in absorption associated with oral cannabinoid compositions is a negative feature of their use, it has been accepted to date because alternatives have been lacking.

SUMMARY OF THE DISCLOSURE

The current disclosure provides use of N-acylated fatty amino acids to reduce absorption variability in oral cannabinoid-based compositions. In particular embodiments, use of an N-acylated fatty amino acid brings absorption variability in cannabinoid-based compositions below a 45% coefficient of variation (% CV), below a 40% CV, or below a 30% CV. In particular embodiments, use of N-acylated fatty amino acids in an oral cannabinoid composition reduces the inter-subject variability by 2-fold in a direct comparison of an oral cannabinoid formulation containing the N-acylated fatty amino acid versus the same formulation without the N-acylated fatty amino acid. More particularly, in terms of bioavailability (amount of cannabinoid in the blood following administration) inter-subject variability without an N-acylated fatty amino acid in the composition was 84% as compared to 41% or 38% with an N-acylated fatty amino acid in the composition.

As disclosed herein, the ratio of cannabinoid to N-acylated fatty amino acid in the oral formulation is important to observe the described reduction in inter-subject absorption variability. A 1:2 ratio (weight/weight (w/w)) of cannabinoid to N-acylated fatty amino was not effective in bringing the % CV below 45%. However, a 1:20 ratio achieved 41% CV, a 1:10 ratio achieved a 26% CV-38% CV, and a ratio of 1:6 achieved a 39% CV. Thus, the current disclosure provides use of particular ratios of cannabinoid to N-acylated fatty amino to reduce inter-subject variability in cannabinoid update.

Particular embodiments include selecting an N-acylated fatty amino acid and cannabinoid in a 1:20, 1:10, or 1:6 ratio to create an oral formulation with reduced absorption variability when administered to subject.

DETAILED DESCRIPTION

Figure 1A:
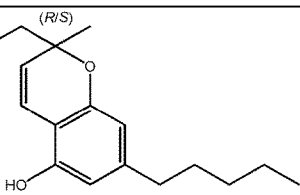
FIG. 1A provides exemplary cannabinoid structures.
Figure 1A:
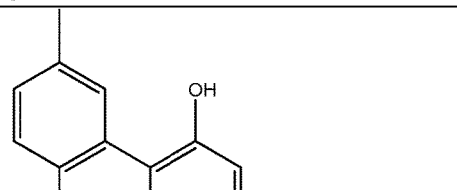
Figure 1A:
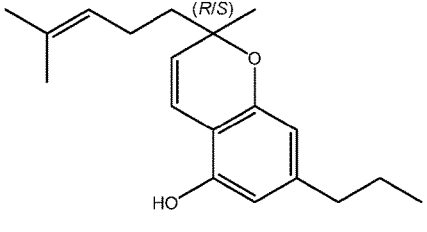
Figure 1A:
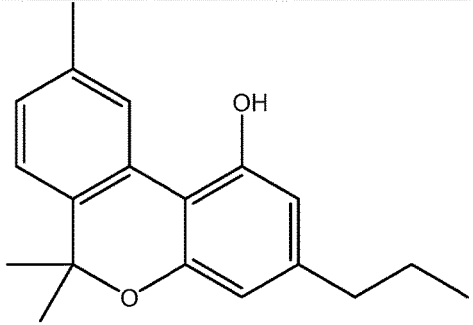
Figure 1A:
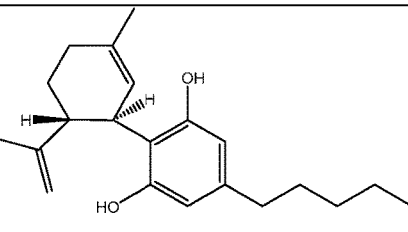
Figure 1A:
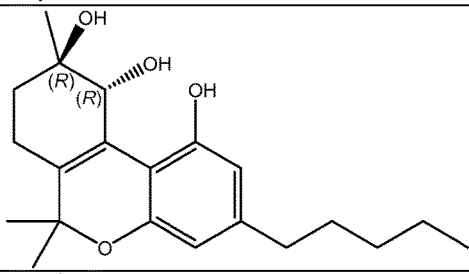
Figure 1A:
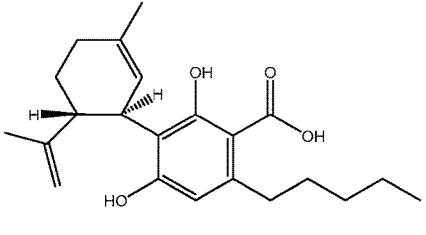
Figure 1A:
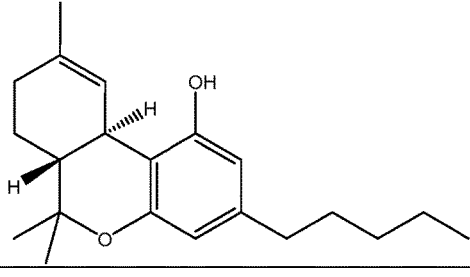

Oral cannabinoid administration is generally characterized by wide variability in absorption within the same person from dose to dose (intrasubject variability). This variability is a long-standing issue, having been discussed in, for example, Wheless et al., CNS Drugs (2019) 33: 593-604; Oh et al., Clinical Pharmacology: Advances and Applications (2017) 9: 9-17; Huestis, Chem Biodivers. (2007) 4(8): 1770-1804; Kim & Yoon, J. Chromatogr., Sect. B. (1996) 682: 55; Ohlsson et al. Clin. Pharmacol. Ther. (1980) 28: 409; and Perez-Reyes et al., Clin. Pharmacol. Ther. (1973)14: 48. For example, Wheless et al. describes that in pediatric epilepsy patients the coefficient of variation (% CV) associated with absorption ranges from 103% CV-135% CV (see Table 3). Oh et al. describes that in healthy volunteers who have fasted before ingesting an oral cannabinoid formulation (as in the current disclosure) the coefficient of variation (% CV) associated with absorption was 58% CV-60% CV (see Table 1, last 2 columns). This variability is undesirable because it makes the prescription of specific doses difficult, and in some cases, impossible. The consequences of this dosing conundrum can be severe over- or under-dosing patients in the treatment of disease. While the variability in absorption associated with oral cannabinoid compositions is a negative feature of their use, it has been accepted to date because alternatives have been lacking.

The current disclosure provides use of N-acylated fatty amino acids to reduce absorption variability in oral cannabinoid-based compositions. In particular embodiments, use of an N-acylated fatty amino acid brings absorption variability in cannabinoid-based compositions below a 45% coefficient of variation (% CV), below a 40% CV, or below a 30% CV. In particular embodiments, use of N-acylated fatty amino acids in an oral cannabinoid composition reduces the inter-subject variability by 2-fold in a direct comparison of an oral cannabinoid formulation containing the N-acylated fatty amino acid versus the same formulation without the N-acylated fatty amino acid. More particularly, in terms of bioavailability (amount of cannabinoid in the blood following administration) inter-subject variability without an N-acylated fatty amino acid in the composition was 84% as compared to 41% or 38% with an N-acylated fatty amino acid in the composition.

As disclosed herein, the ratio of cannabinoid to N-acylated fatty amino acid in the oral formulation is important to observe the described reduction in inter-subject absorption variability. A 1:2 ratio of cannabinoid to N-acylated fatty amino was not effective in bringing the % CV below 45%. However, a 1:20 ratio achieved 41% CV, a 1:10 ratio achieved a 26% CV-38% CV, and a ratio of 1:6 achieved a 39% CV. Thus, the current disclosure provides use of particular ratios of cannabinoid to N-acylated fatty amino to reduce inter-subject variability in cannabinoid update.

In particular embodiments, the cannabinoid: N-acylated fatty amino acid w/w ratio can be 1:4, 1:5, 1:6, 1:7, 1:8, 1:9, 1:10, 1:11, 1:12, 1:13, 1:14, 1:15, 1:16, 1:17, 1:18, 1:19, 1:20, 1:21, 1:22, 1:23, 1:24, 1:25. In particular embodiments, the N-acylated fatty amino acid/cannabinoid w/w ratio is 1:6, 1:10, or 1:20. In particular embodiments, the N-acylated fatty amino acid includes sodium N-[8-(2-hydroxybenzoyl) amino] caprylate (SNAC) and the cannabinoid includes Δ9-Tetrahydrocannabinol (THC), cannabidiol (CBD), or synthetic forms thereof.

Aspects of the current disclosure are now described with additional options and detail as follows: (i) Cannabinoids; (ii) N-Acylated Fatty Amino Acids; (iii) Oral Formulations; (iv) Methods of Use; (v) Exemplary Embodiments; (vi) Exemplary Experimental Procedures; (vii) Experimental Examples; and (viii) Closing Paragraphs.

(I) CANNABINOIDS

Figure 1B:
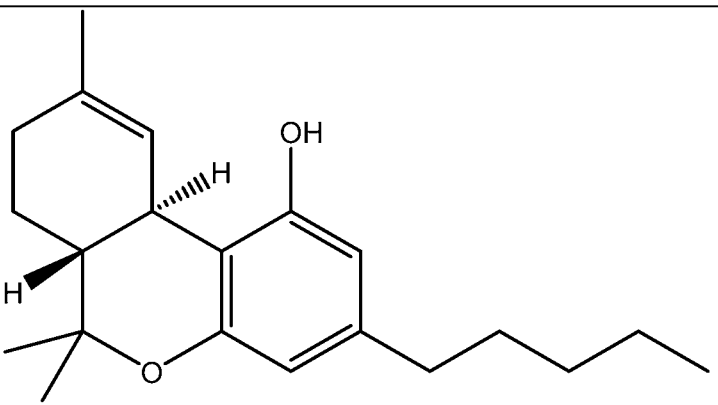
FIG. 1B provides additional exemplary structures of cannabinoids that can be synthetically derived (THC, nabilone, CBD, 7-OH-CBD, CBDV, 7-OHCBDV, and formulas I-XVI).
Figure 1B:
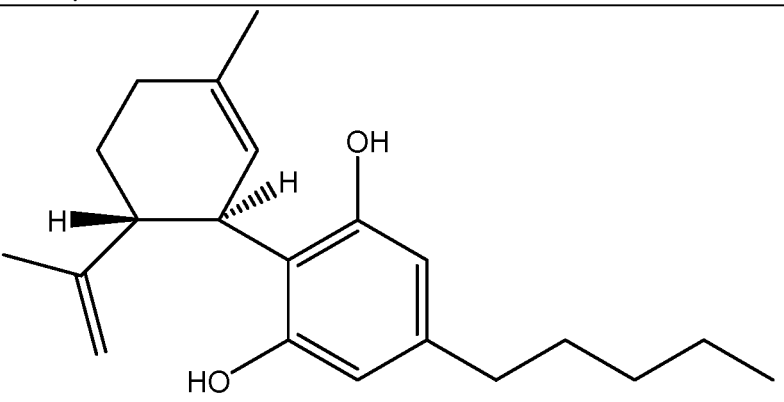
Figure 1B:
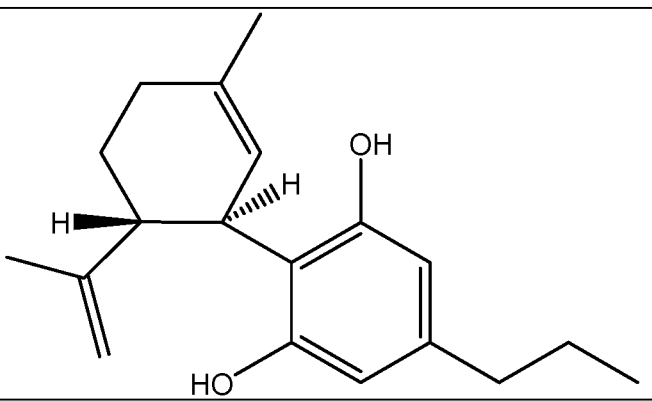
Figure 1B:
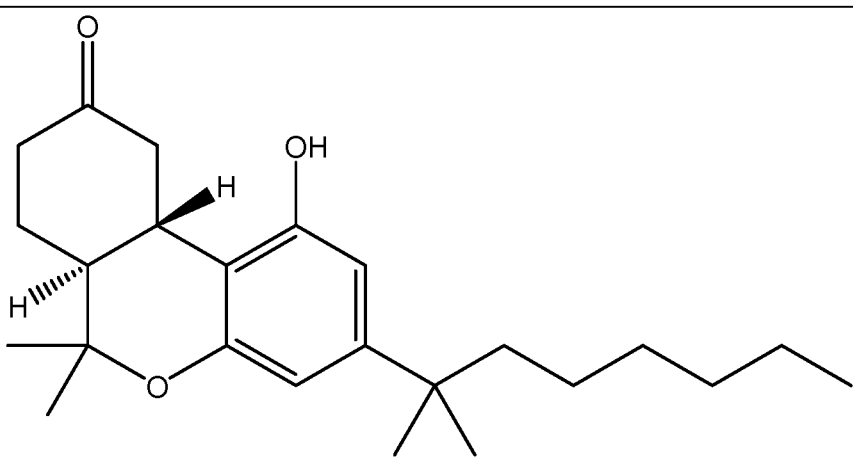
Figure 1B:
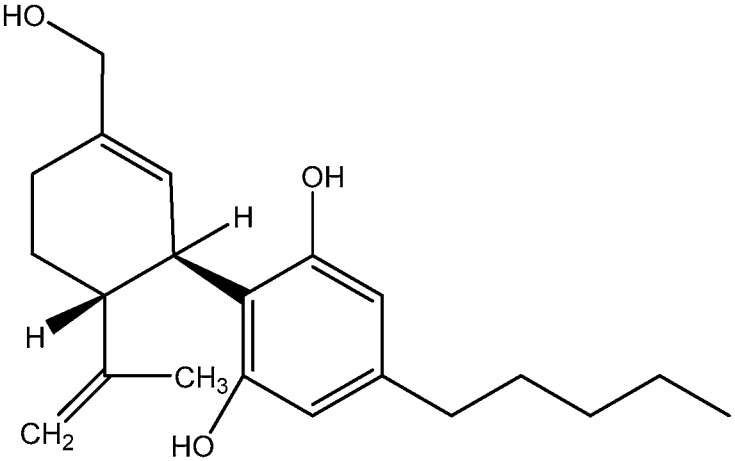
Figure 1B:
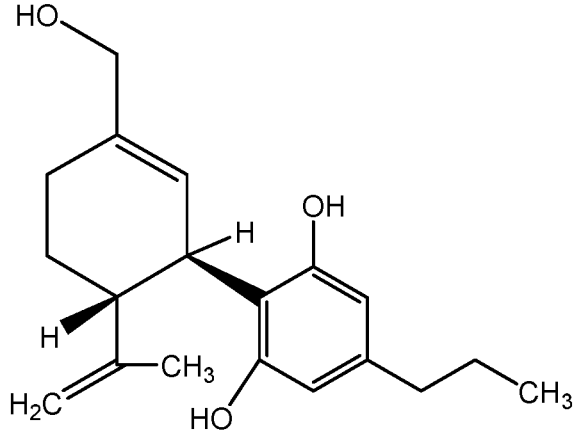
Figure 1B:
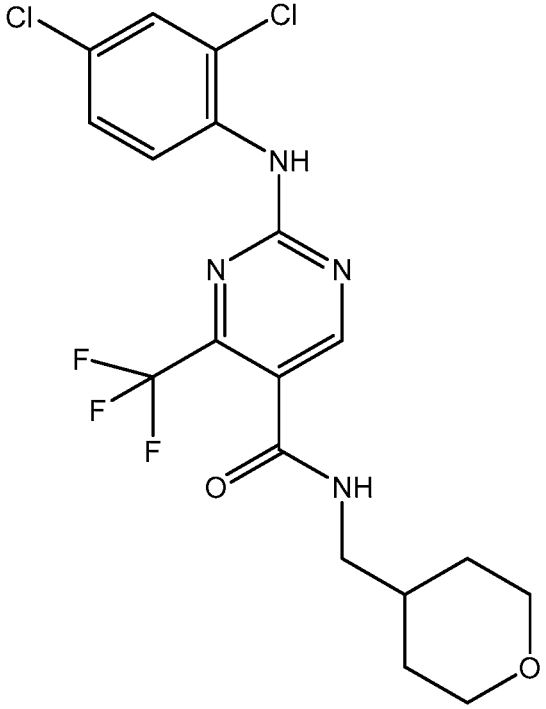
Figure 1B:
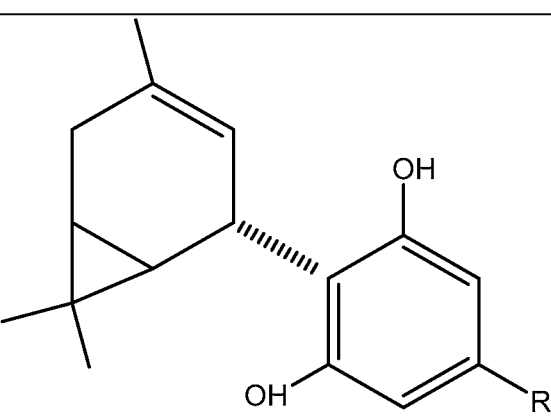
Figure 1B:
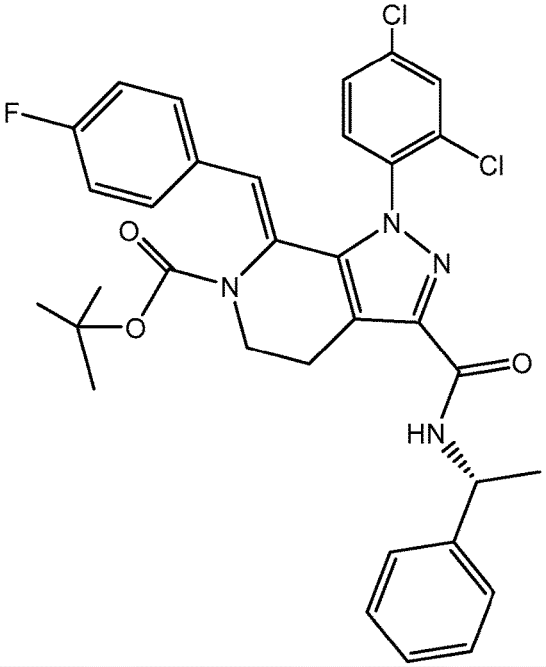
Figure 1B:
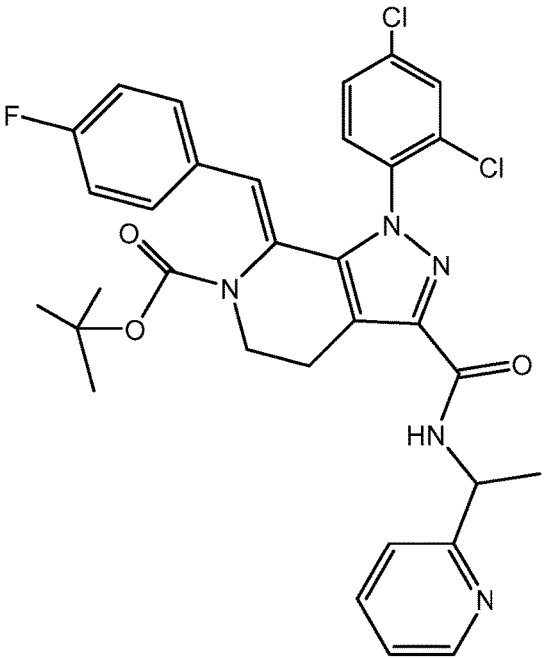
Figure 1B:
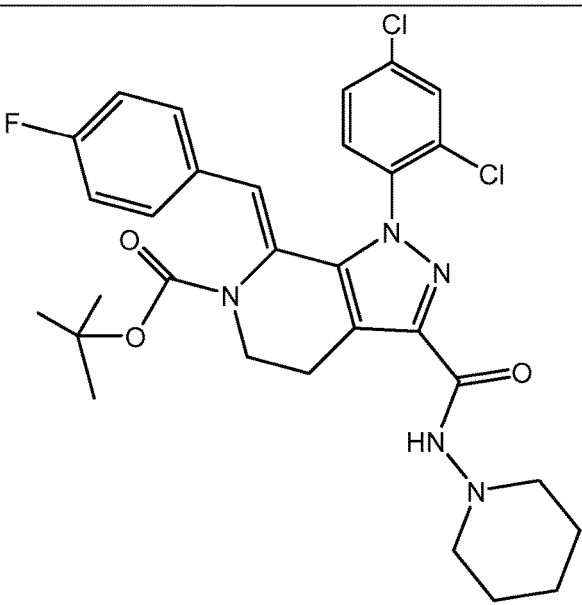
Figure 1B:
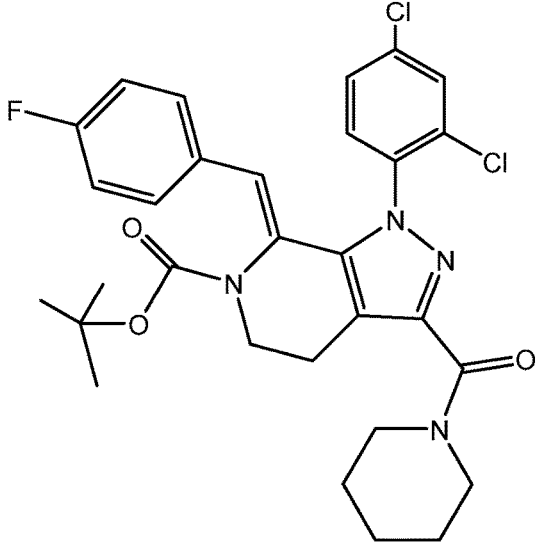
Figure 1B:
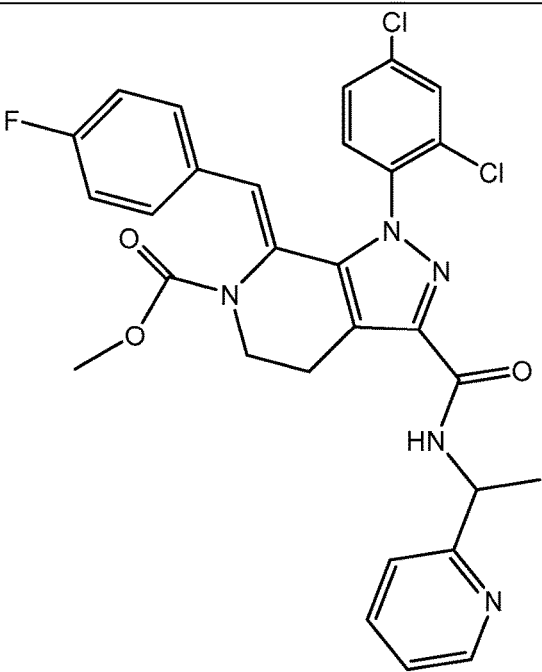
Figure 1B:
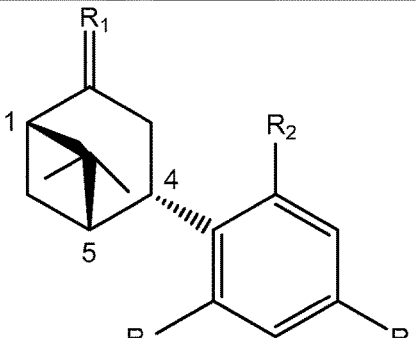
Figure 1B:
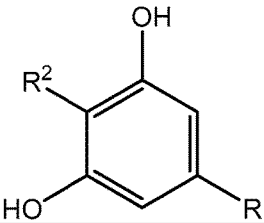
Figure 1B:
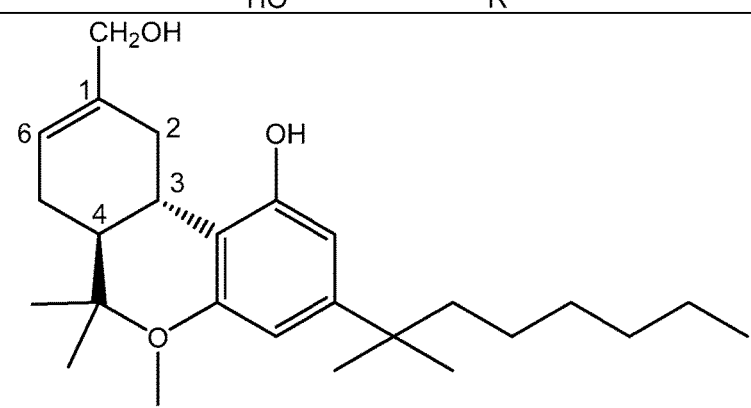
Figure 1B:
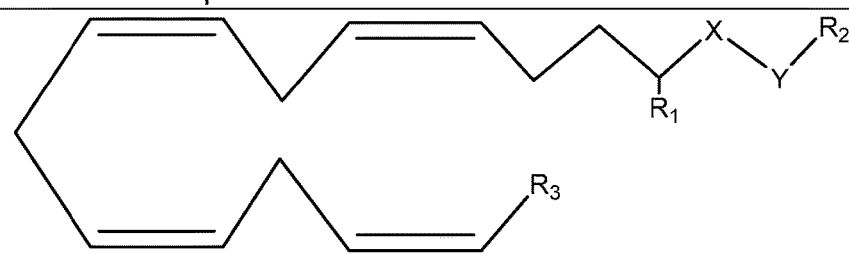
Figure 1B:
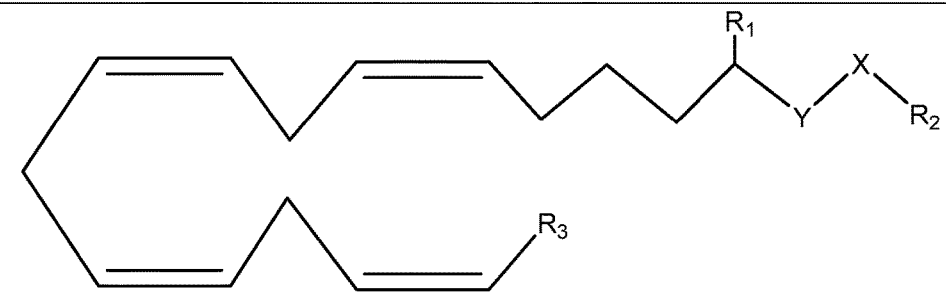

Cannabinoids are a group of cyclic molecules from cannabis plants that activate cannabinoid receptors (i.e., CB1 and CB2) in cells. There are at least 85 different cannabinoids that can be isolated from cannabis. Many cannabinoids produced by cannabis plants, such as Δ9-Tetrahydrocannabinol (THC) and cannabidiol (CBD), have very low or no solubility in water. The most notable cannabinoids are THC and CBD. Additional examples include cannabigerol (CBG), cannabichromene (CBC), cannabinol (CBN), cannabinodiol (CBDL), cannabicyclol (CBL), cannabivarin (CBV), tetrahydrocannabivarin (THCV), cannabidivarin (CBDV), cannabichromevarin (CBCV), cannabigerovarin (CBGV), cannabigerol monomethyl ether (CBGM), cannabinerolic acid, cannabidiolic acid (CBDA), Cannabinol propyl variant (CBNV), cannabitriol (CBO), tetrahydrocannabinolic acid (THCA), and tetrahydrocannabivarinic acid (THCVA). See, for example, FIGS. 1A, 1B. Extracts of the cannabis plant similarly include flavonoid compounds, terpenes, terpenoid, and synthetic, semisynthetic or highly purified versions of any such constituent.

In particular embodiments, synthetic cannabinoids include natural cannabinoids that are synthesized chemically and also their analogs and derivatives. Derivatives of natural cannabinoids can include metabolites of cannabinoids which are disclosed in WO2015/198078. For example, the metabolite of CBD includes 7-OH-CBD and the metabolite of CBDV includes 7-OH-CBDV.

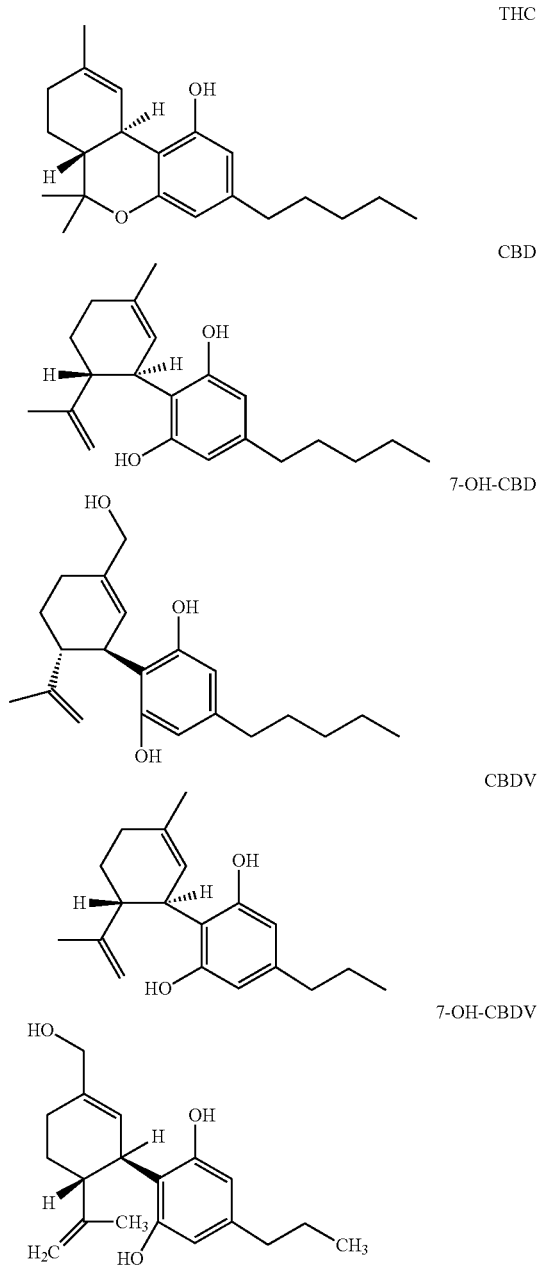

Other examples of synthetic cannabinoids include 3-carbamoyl-2-pyridone, and its derivatives and/or analogs disclosed in US2008/0103139; pyrimidine derivatives and/or analogs disclosed in US2006/0293354; carenadiol and its derivatives and/or analogs thereof disclosed in U.S. Pat. No. 4,758,597; cannabinoid carboxylic acids and their derivatives and/or analogs disclosed in WO2013/045115; pyrido [3,2-E][1,2,4]triazolo[4,3-C]pyrimidine and its derivatives and/or analogs disclosed in WO2008/118414; tetrahydropyrazolo[3,4-C] pyridine and its derivatives and/or analogs disclosed in WO2007/112399; bicyclo[3.1.1]heptan-2-one cannabinoid and its derivatives and/or analogs disclosed in WO2006/043260; resorcinol and its derivatives and/or analogs disclosed in WO2005/123051; dexanabinol compounds and their derivatives and/or analogs disclosed in WO2004/050011; cannabimimetic lipid amide compounds and their derivatives and/or analogs disclosed in WO2000/032200; nabilone and its derivatives and/or analogs disclosed in US2010/0168066; 2-oxoquinolone compounds and their derivatives and/or analogs disclosed in US2003/0191069; and 3,4-diaryl-4,5-dihydro-(h)-pyrazole-1-carboxamide and its derivatives and/or analogs disclosed in US2011/0137040.

In particular embodiments, 3-carbamoyl-2-pyridone and its derivatives and/or analogs include methyl 3-methyl-2-{[2-oxo-1-(2-oxo-ethyl)-1,2,5,6,7,8,9,10-octahydro-cycloocta[b]pyridine-3-carbonyl]-amino}-butyrate; dimethyl 2-[(1-cyclohexylmethyl-5,6-dimethyl-2-oxo-1,2-dihydro-pyridine-3-carbonyl)-amino]-succinate; and methyl 2-{[1-(3-methoxycarbonylamino-propyl)-2-oxo-1,2,5,6,7,8,9,10-octahydro-cycloocta[b]pyridine-3-carbonyl]-amino}-2-methyl-propionate.

In particular embodiments, pyrimidine derivatives and/or analogs include a compound having Formula (I) (2-((2,4-dichlorophenyl)amino)-N-((tetrahydro-2H-pyran-4-yl)methyl)-4-(trifluoromethyl)pyrimidine-5-carboxamide), Formula (I)

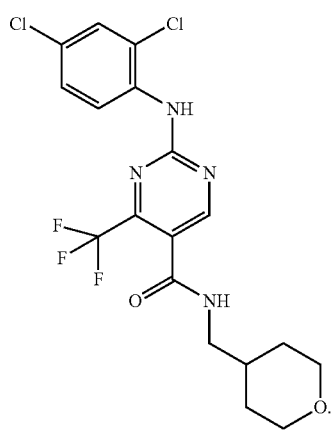

Other pyrimidine derivatives and/or analogs include 2-(3-Chlorophenylamino)-4-trifluoromethylpyrimidine-5-carboxylic acid cyclohexylmethyl-amide; 2-Phenylamino-4-trifluoromethylpyrimidine-5-carboxylic acid cyclohexylmethyl-amide; 1-[2-(2,3-Dichlorophenylamino)-4-trifluoromethylpyrimidin-5-yl]-1-morphol-in-4-yl-methanone; 1-[2-(2,4-Dichlorophenylamino)-4-trifluoromethylpyrimidin-5-yl]-1-morphol-in-4-yl-methanone; and 2-(3-Chlorophenylamino)-4-trifluoromethylpyrimidin-5-carboxylic acid cyclopentylamide.

In particular embodiments, carenadiol and its derivatives and/or analogs include compounds having Formula (II), Formula (II)

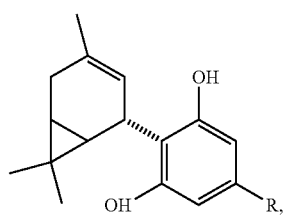

wherein R is a lower alkyl having 1 to 9 carbon atoms including isomeric forms such as i-butyl, n-butyl, and t-butyl. In particular embodiments, R is $C_5H_{11}$ or 1,1-dimethylheptyl.

In particular embodiments, cannabinoid carboxylic acids and their derivatives and/or analogs include compounds having Formula (III), (IV), (V), or (VI), Formula (III)

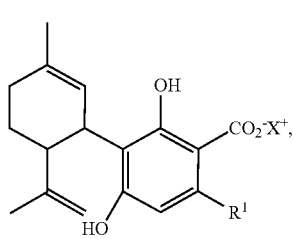

Formula (IV)

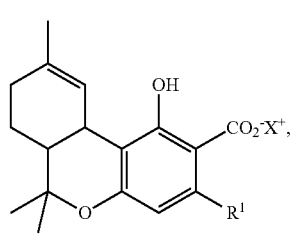

Formula (V)

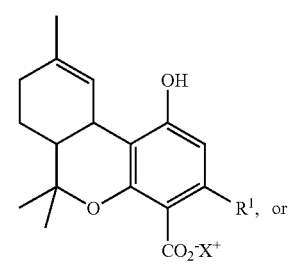

Formula (VI)

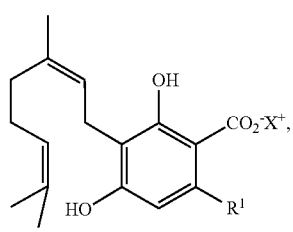

wherein:
 $R^1$ is a straight-chain, branched or cyclic hydrocarbon residue with one C atom to 12 C atoms; and
 $X^+$ is $NH_4^+$, mono-, di- or trivalent metal ions; or primary, secondary, tertiary or quaternary organic ammonium ions with up to 48 C atoms, which may bear still further functional groups.

Examples of multivalent ammonium ions include N,N-dicyclo-hexylamine-$H^+$ and N,N-dicyclohexyl-N-ethylamine-$H^+$. $X^+$ can also be the hydrogen cation of a pharmaceutical active substance with at least one basic nitrogen atom, such as for example morphine, methadone (or an enantiomer thereof) or hydromorphone.

In particular embodiments, pyrido[3,2-E][1,2,4]triazolo[4,3-C]pyrimidine and its derivatives and/or analogs include 5-tert-butyl-8-(2-chlorophenyl)-9-(4-chlorophenyl)pyrido[3,2-e][1,2,4]triazolo[4,3-c]pyrimidin-3(2H)-one; 8-(4-bromo-2-chlorophenyl)-5-tert-butyl-9-(4-chlorophenyl)pyrido[3,2-e][1,2,4]triazolo[4,3-c]pyrimidin-3(2H)-one;

5-fert-butyl-9-(4-chlorophenyl)-8-(2-methylphenyl)pyrido[3,2-e][1,2,4]triazolo[4,3-c]pyrimidin-3(2H)-one; 9-(4-bromophenyl)-5-tert-butyl-8-(2-chlorophenyl)pyrido[3,2-e][1,2,4]triazolo[4,3-c]pyrimidin-3(2H)-one; and 5-tert-butyl-8-(2-chlorophenyl)-9-(4-chlorophenyl)pyrido[3,2-e][1,2,4]triazolo[4,3-c]pyrimidine.

In particular embodiments, tetrahydro-pyrazolo[3,4-C]pyridine and its analogs and/or derivatives include compounds having Formula (VII), (VIII), (IX), (X), or (XI), Formula (VII)

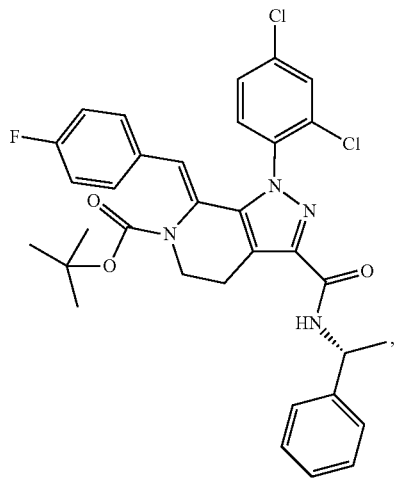

Formula (VIII)

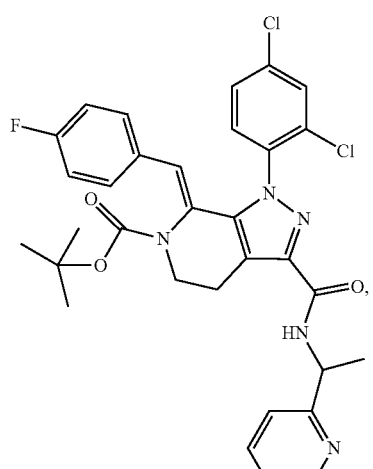

Formula (IX)

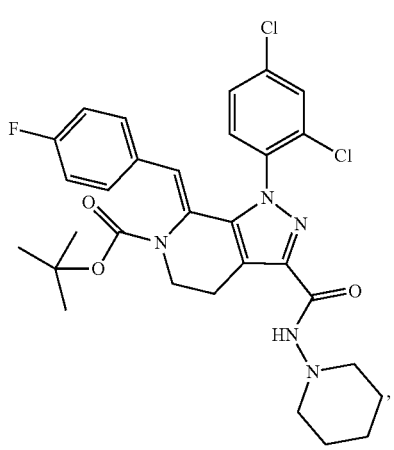

Formula (X)

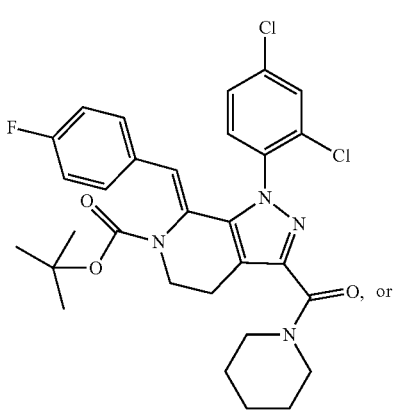

Formula (XI)

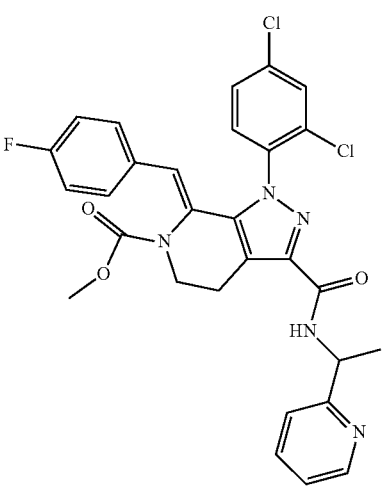

In particular embodiments, bicyclo[3.1.1]heptan-2-one cannabinoids and their derivatives and/or analogs include compounds having Formula (XII), Formula (XII)

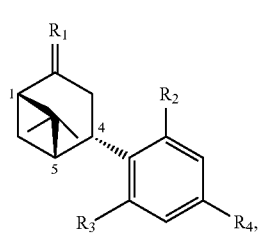

having a specific stereochemistry wherein C-4 is S, the protons at C-1 and C-5 are cis in relation to one another and the protons at C-4 and C-5 are trans; and wherein:

$R_1$ is (a) O or S; (b) $C(R')_2$ wherein R' at each occurrence is independently selected from the group consisting of hydrogen, cyano, —OR", —N(R")$_2$, a saturated or unsaturated, linear or branched $C_1$-$C_6$ alkyl, $C_1$-$C_6$ alkyl-OR" or $C_1$-$C_6$alkyl-N(R")$_2$ wherein at each occurrence R" is independently selected from the group consisting of hydrogen, C(O)R'", C(O)N(R'")$_2$, C(S)R'", saturated or unsaturated, linear or branched $C_1$-$C_6$ alkyl, $C_1$-$C_6$ alkyl-OR'", and $C_1$-$C_6$ alkyl-N(R'")$_2$, wherein at each occurrence R'" is independently selected from the group consisting of hydrogen or saturated or unsaturated, linear, branched or cyclic $C_1$-$C_{12}$alkyl; or (c) NR" or N—OR" wherein R" is as previously defined;

$R_2$ and $R_3$ are each independently (a) —R", —OR", —N(R")$_2$, —SR", —S(O)(O)NR", wherein at each occurrence R" is as previously defined; (b) —S(O)R$^b$, —S(O)(O)R$^b$ wherein R$^b$ is selected from the group consisting of hydrogen, saturated or unsaturated, linear or branched $C_1$-$C_6$alkyl, $C_1$-$C_6$alkyl-OR", and $C_1$-$C_6$alkyl-N(R")$_2$, wherein R" is as previously defined; or (c) —OC(O)OH, —OS(O)(O)OR$^e$, —OP(O)(OR$^e$)$_2$, —OR$^d$ or —OC(O)—R$^d$ chain terminated by —C(O)OH, —S(O)(O)OR$^e$, or —P(O)(OR$^e$)$_2$, wherein R$^d$ is a saturated or unsaturated, linear or branched $C_1$-$C_6$ alkyl and R$^e$ is at each occurrence selected from the group consisting of hydrogen and R$^d$ as previously defined; and $R_4$ is (a) R wherein R is selected from the group consisting of hydrogen, halogen, OR''', OC(O)R''', C(O)OR''', C(O)R''', OC(O)OR''', CN, N(R''')$_2$, NC(O)R''', NC(O)OR''', C(O)N(R''')$_2$, NC(O)N(R''')$_2$, and SR''', wherein at each occurrence R''' is as previously defined; (b) a saturated or unsaturated, linear, branched or cyclic $C_1$-$C_{12}$ alkyl-R wherein R is as previously defined; (c) an aromatic ring which can be further substituted at any position by R wherein R is as previously defined; or (d) a saturated or unsaturated, linear, branched or cyclic $C_1$-$C_{12}$ alkyl optionally terminated by an aromatic ring which can be further substituted as defined in (c).

In particular embodiments, resorcinol and its derivatives and/or analogs include compounds having Formula (XIII),

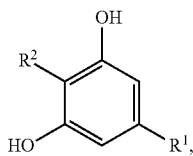

Formula (XIII)

wherein:
$R^1$ is (a) straight or branched alkyl chain of 7 to 12 carbon atoms; (b) —O—R$^3$, where R$^3$ is a straight or branched alkyl chain of 5 to 9 carbon atoms, optionally substituted by one phenyl group; or (c) —(CH$_2$)$_n$—O—R$^4$, where n is an integer from 1 to 7, and R$^4$ is a straight alkyl chain of 1 to 5 carbon atoms; and
$R^2$ is a non-cyclic terpenoid including from 10 to 30 carbon atoms.

In particular embodiments, resorcinol and its derivatives and/or analogs include compounds having Formula (XIII), wherein $R^1$ and $R^2$ are as follows:
$R^1$ is a straight alkyl chain of 5 to 8 carbon atoms, optionally substituted with one methyl group; and
$R^2$ is selected from geranyl optionally substituted with one —OH, and farnesyl optionally substituted with one —OH.

In particular embodiments, resorcinol and its derivatives and/or analogs include compounds having Formula (XIII), wherein:
R1 is (a) straight or branched alkyl chain of 7 to 12 carbon atoms; (b) —O—R3, where R3 is a straight or branched alkyl chain of 5 to 9 carbon atoms, optionally substituted by one phenyl group; or (c) —(CH2)$_n$—O—R4, where n is an integer from 1 to 7, and R4 is a straight alkyl chain of 1 to 5 carbon atoms; and R2 is a non-cyclic terpenoid including from 10 to 30 carbon atoms; with the proviso that when R1 is isononyl, R2 is not geranyl.

In particular embodiments, resorcinol and its derivatives and/or analogs include compounds having Formula (XIII), wherein $R^1$ is (a) a straight or branched alkyl of 7 to 12 carbon atoms; (b) a group —O—R$^3$, where R$^3$ is a straight or branched alkyl of 5 to 9 carbon atoms, or a straight or branched alkyl substituted at the terminal carbon atom by a phenyl group; or (c) a group —(CH$_2$)$_n$—O-alkyl, where n is an integer from 1 to 7 and the alkyl group contains 1 to 5 carbon atoms.

In particular embodiments, resorcinol and its derivatives and/or analogs include compounds of Formula (XIII), wherein $R^2$ is a non-cyclic terpenoid carbon chain such as geranyl, farnesyl, and related non-cyclic terpenes and their isomers as well as other non-cyclic paraffinic or olefinic carbon chains.

In particular embodiments, resorcinol and its derivatives and/or analogs include compounds of Formula (XIII), wherein $R^1$ is dimethylheptyl and $R^2$ is geranyl.

In particular embodiments, dexanabinol compounds and their derivatives and/or analogs include high enantiomeric purity compounds having Formula (XIV),

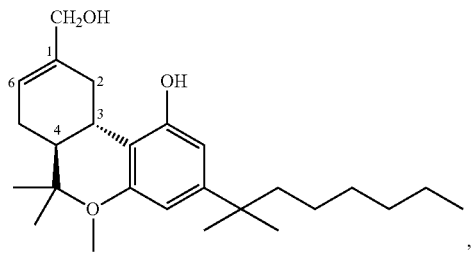

Formula (XIV)

and having the (3S, 4S) configuration and being in enantiomeric excess of at least 99.90% over the (3R,4R) enantiomer.

In particular embodiments, cannabimimetic lipid amide compounds and their derivatives and/or analogs include compounds having Formula (XV),

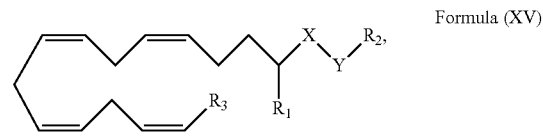

Formula (XV)

wherein:
X is one of the group consisting of C=O and NH, and Y is the other of that group. Expressed another way, X may be C=O and Y may be NH, or Y may be C=O and X may be NH, but both X and Y may not be the same group.
R$_1$ is H or an alkyl group. In particular embodiments, R$_1$ is H, CH$_3$, or (CH$_3$)$_2$;
R$_2$ is an alkyl, a substituted alkyl, an alkenyl or an alkynyl group. In particular embodiments, R$_2$ is CH(R) CH$_2$Z, CH$_2$CH(R)Z, or CH(R)(CH$_2$)nCH$_2$Z; R being H, CH, CH$_3$, CHCH, CH$_2$CF$_3$, or (CH$_3$)2; Z being H, halogen, N$_3$, NCS, or OH; and n being selected from the group consisting of 0, 1 and 2.

$R_3$ is an alkyl, a substituted alkyl, an aryl, an alkylaryl, an O-alkyl, an O-alkylaryl, a cyclic and a heterocyclic group. O-alkyl and O-alkylaryl refer to groups in which an oxygen atom is interposed between carbon atoms on the anandamide portion and substituent group. Examples of such $R_3$ groups include cyclohexyl, cyclopentyl, alkylcyclohexyl, alkylcyclopentyl, piperidinyl, morpholinyi and pyridinyl. In particular embodiments, $R_3$ is n-$C_5H_{10}Z'$, n-$C_6H_{12}Z'$, n-$C_7H_{14}Z'$, or 1', 1'-C$(CH_3)_2(CH_2)_5$ $CH_2Z'$; $Z'$ being H, halogens, CN, $N_3$, NCS, or OH.

In particular embodiments, cannabimimetic lipid amide compounds and their derivatives and/or analogs include compounds having Formula (XVI),

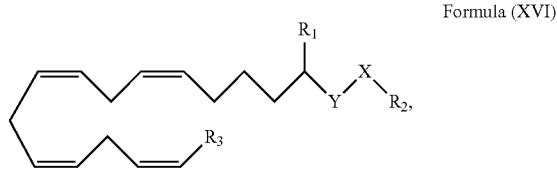

Formula (XVI)

wherein:

Y is one of the group consisting of C=O and NH and X is the other of that group.

$R_1$ is H or an alkyl group. In particular embodiments, $R_1$ is H, $CH_3$, or $(CH_3)_2$.

$R_2$ is an alkyl, a substituted alkyl, an alkenyl, an alkynyl, an O-alkyl, a cyclic, a polycyclic, or a heterocyclic group. In particular embodiments, $R_2$ is

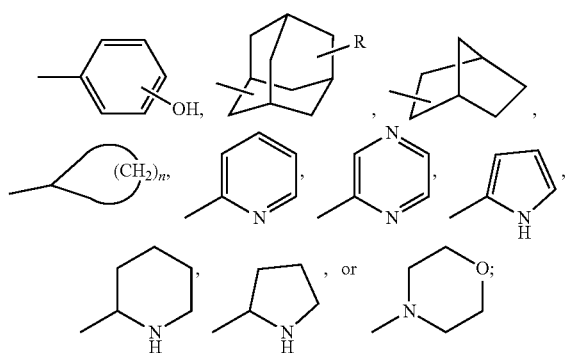

$CH=CH_2$, $CH=C(CH_3)_2$, $C\equiv CH$, $CH_2OCH_3$, $CH(R)(CH_2)nCH_2Z$, or $CH_2CH(R)(CH_2)nZ$; R being H, $CH_3$ or $(CH_3)_2$; Z being H, halogens, $N_3$, NCS, OH, or OAc; and n 0, 1, or 2; and $R_3$ is an alkyl, a substituted alkyl, an aryl, an alkylaryl, an O-alkyl, an O-alkylaryl, a cyclic, or a heterocyclic group. In particular embodiments $R_3$ includes cyclohexyl, cyclopentyl, alkylcyclohexyl, alkylcyclopentyl, piperidinyl, morpholinyi and pyridinyl. In particular embodiments, $R_3$ is n-$C_5H_{10}Z'$, n-$C_6H_{12}Z'$, n-$C_7H_{14}Z'$, or 1',1'-C$(CH_3)_2(CH_2)_5$ $CH_2Z'$; $Z'$ being H, halogen, CN, $N_3$, NCS, or OH.

In particular embodiments, nabilone and its derivatives and/or analogs include compounds having Formula (XVII):

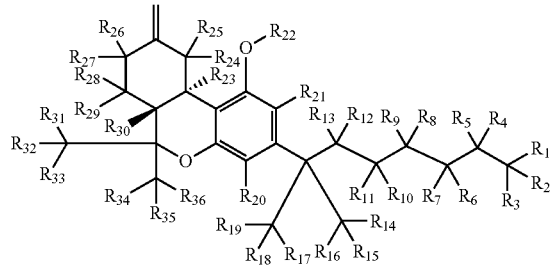

Formula (XVII)

wherein:

$R^1$-$R^{36}$ are independently selected from the group consisting of hydrogen and deuterium. Nabilone derivatives and/or analogs can refer to compounds wherein at least one of $R^1$-$R^{36}$ includes deuterium. For the chemical structure of nabilone, see FIG. 1B.

Cannabinoids can be medicinal compounds and/or can be provided in combination with nutritional supplements.

(II) N-ACYLATED FATTY AMINO ACIDS

In particular embodiments, the N-acylated fatty amino acid is sodium N-[8-(2-hydroxybenzoyl) amino] caprylate (SNAC). Other names for SNAC include Sodium-N-salicyloyl-8-aminocaprylate, Monosodium 8-(N-salicyloylamino) octanoate, N-(salicyloyl)-8-aminooctanoic acid monosodium salt, monosodium N-{8-(2-hydroxybenzoyl) amino}octanoate, or sodium 8-[(2-hydroxybenzoyl)amino] octanoate. SNAC has the structure:

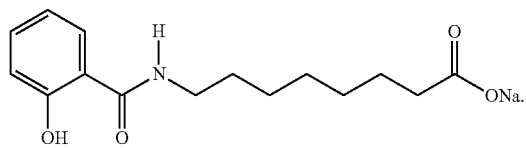

Salts of SNAC may also be used as a carrier.
Other forms of SNAC include:

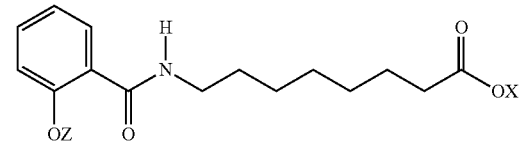

wherein X and Z are independently H, a monovalent cation, a divalent metal cation, or an organic cation. Examples of monovalent cations include sodium and potassium. Examples of divalent cations include calcium and magnesium. Examples of organic cations include ammonium and tetramethylammonium.

Figure 2:
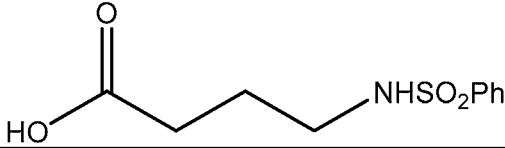
FIG. 2 provides modified amino acids of compounds I-XXXV.
Figure 2:
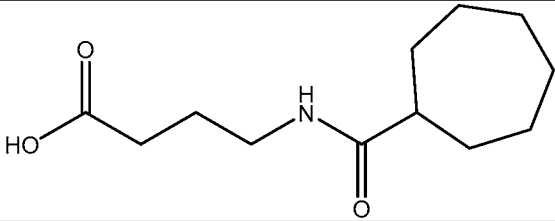
Figure 2:
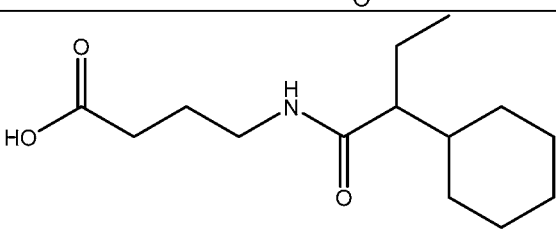
Figure 2:
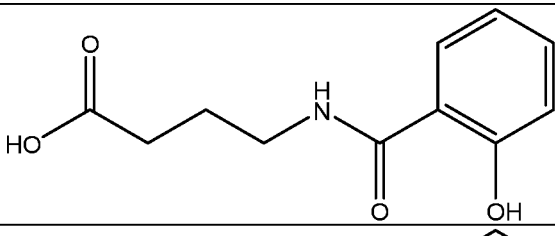
Figure 2:
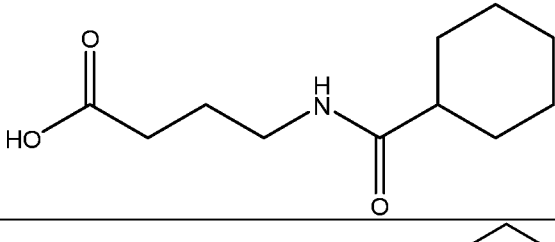
Figure 2:
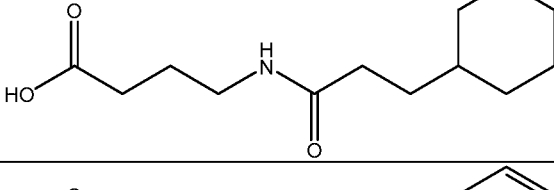
Figure 2:
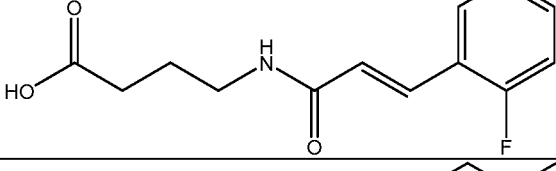
Figure 2:
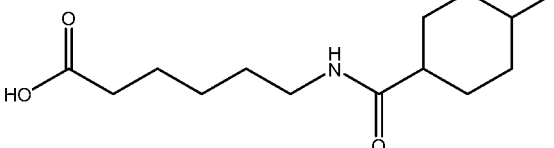
Figure 2:
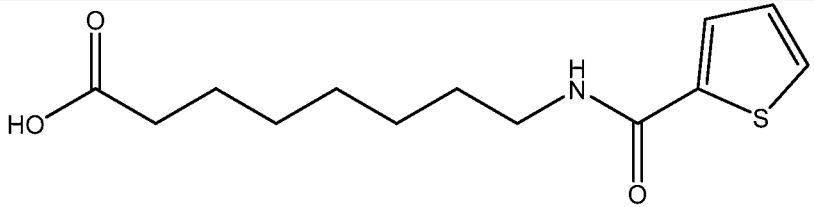
Figure 2:
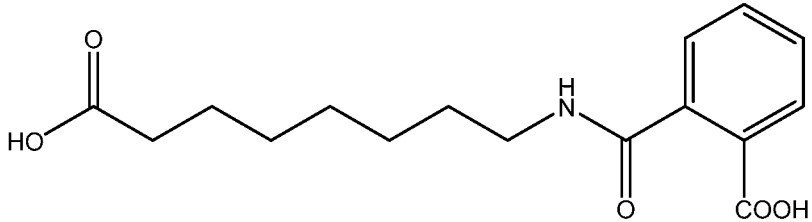
Figure 2:
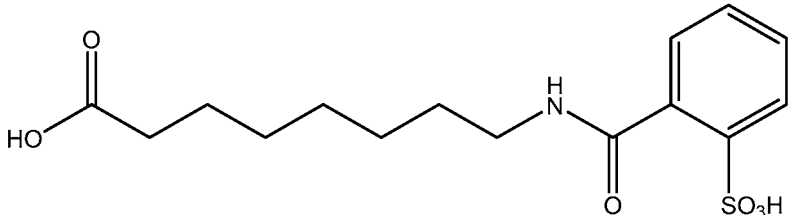
Figure 2:
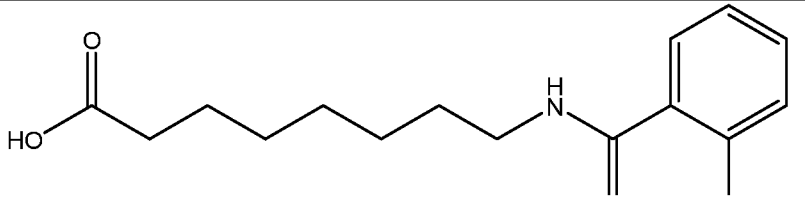
Figure 2:
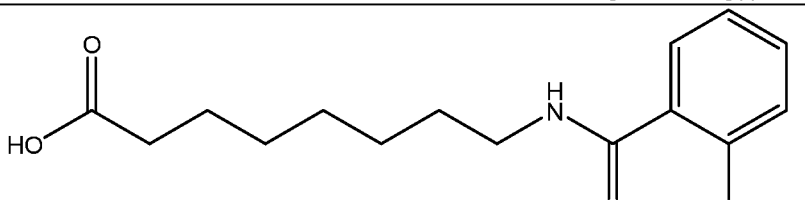
Figure 2:
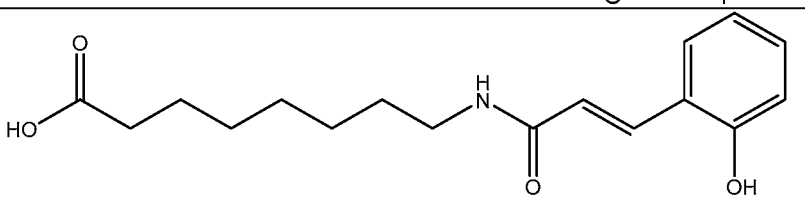
Figure 2:
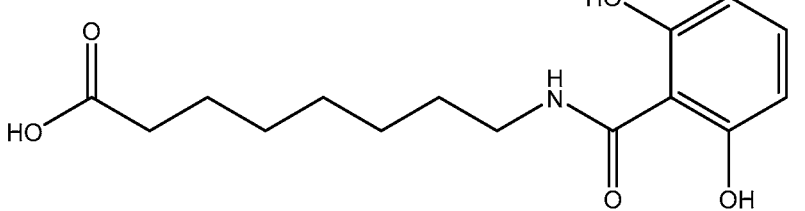
Figure 2:
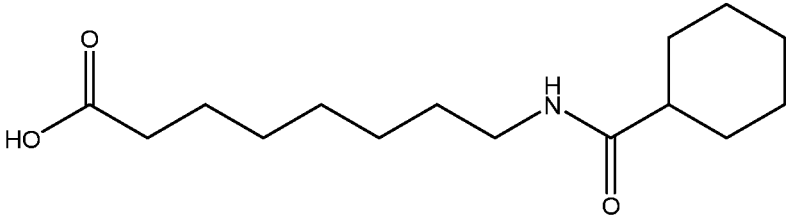
Figure 2:
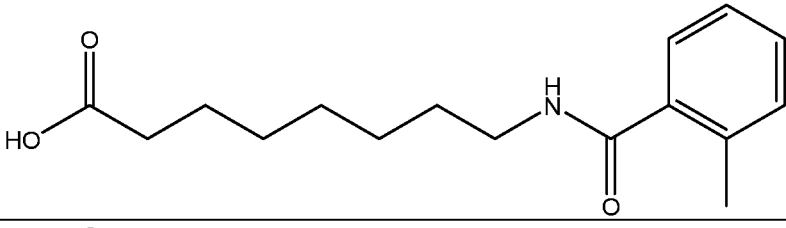
Figure 2:
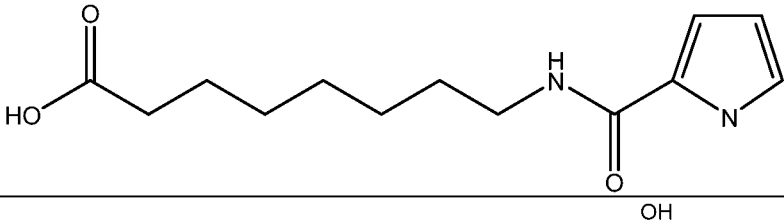
Figure 2:
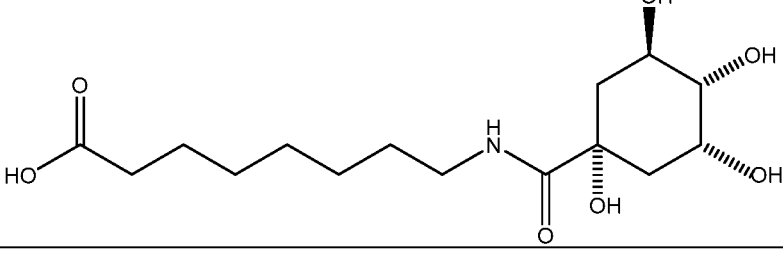
Figure 2:
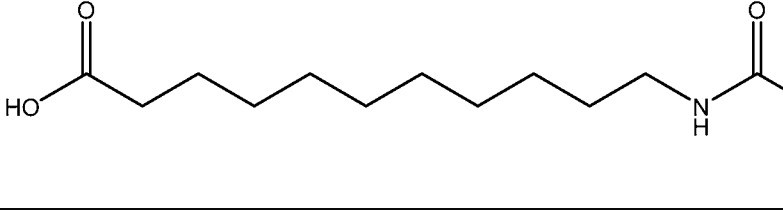
Figure 2:
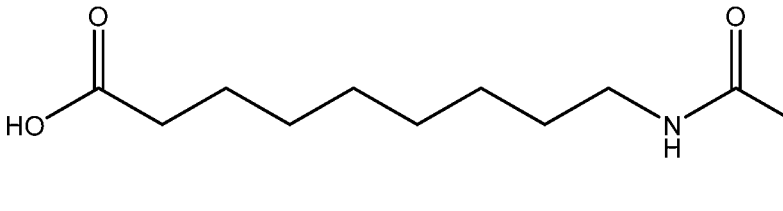

Exemplary modified amino acids, such as N-acylated FA-aas, are provided as compounds I-XXXV (see FIG. 2). Salts of these compounds and other N-acylated FA-aa can also be used as carriers.

Many of the compounds can be readily prepared from amino acids by methods within the skill of those in the art based upon the present disclosure. For example, compounds I-VII are derived from aminobutyric acid. Compounds VIII-X and XXXI-XXIIV are derived from aminocaproic acid. Compounds XI-XXVI and XXXV are derived from aminocaprylic acid. For example, the modified amino acid compounds above may be prepared by reacting the single amino acid with the appropriate modifying agent which reacts with free amino moiety present in the amino acids to form amides. Protecting groups may be used to avoid unwanted side reactions as would be known to those skilled in the art.

The amino acid can be dissolved in aqueous alkaline solution of a metal hydroxide, e.g., sodium or potassium hydroxide, and heated at a te ranging between 5° C. and 70° C., preferably between 10° C. and 40° C., for a period ranging between 1 hour and 4 hours, preferably 2.5 hours. The amount of alkali employed per equivalent of $NH_2$ groups in the amino acid generally ranges between 1.25 and 3 mmole, preferably between 1.5 and 2.25 mmole per equivalent of $NH_2$. The pH of the solution generally ranges between 8 and 13, preferably ranging between 10 and 12.

Thereafter, the appropriate amino acid modifying agent is added to the amino acid solution while stirring. The temperature of the mixture is maintained at a temperature generally ranging between 5° C. and 70° C., preferably between 10° C. and 40° C., for a period ranging between 1 and 4 hours. The amount of amino acid modifying agent employed in relation to the quantity of amino acid is based on the moles of total free $NH_2$ in the amino acid. In general, the amino acid modifying agent is employed in an amount ranging between 0.5 and 2.5 mole equivalents, preferably between 0.75 and 1.25 equivalents, per molar equivalent of total $NH_2$ group in the amino acid.

The reaction is quenched by adjusting the pH of the mixture with a suitable acid, e.g., concentrated hydrochloric acid, until the pH reaches between 2 and 3. The mixture separates on standing at room temperature to form a transparent upper layer and a white or off-white precipitate. The upper layer is discarded, and the modified amino acid is collected from the lower layer by filtration or decantation. The crude modified amino acid is then dissolved in water at a pH ranging between 9 and 13, preferably between 11 and 13. Insoluble materials are removed by filtration and the filtrate is dried in vacuo. The yield of modified amino acid generally ranges between 30 and 60%, and usually 45%.

If desired, amino acid esters, such as, for example benzyl, methyl, or ethyl esters of amino acid compounds, may be used to prepare the modified amino acids. The amino acid ester, dissolved in a suitable organic solvent such as dimethylformamide, pyridine, or tetrahydrofuran can be reacted with the appropriate amino acid modifying agent at a temperature ranging between 5° C. and 70° C., preferably 25° C., for a period ranging between 7 and 24 hours. The amount of amino acid modifying agent used relative to the amino acid ester is the same as described above for amino acids. This reaction may be carried out with or without a base such as, for example, triethylamine or diisopropylethylamine.

Thereafter, the reaction solvent is removed under negative pressure and the ester functionality is removed by hydrolyzing the modified amino acid ester with a suitable alkaline solution, e.g. IN sodium hydroxide, at a temperature ranging between 50° C. and 30° C., preferably 70° C., for a period of time sufficient to hydrolyze off the ester group and form the modified amino acid having a free carboxyl group. The hydrolysis mixture is then cooled to room temperature and acidified, e.g. aqueous 25% hydrochloric acid solution, to a pH ranging between 2 and 2.5. The modified amino acid precipitates out of solution and is recovered by conventional means such as filtration or decantation. Benzyl esters may be removed by hydrogenation in an organic solvent using a transition metal catalyst.

The modified amino acid may be purified by recrystallization or by fractionation on solid column supports. Suitable recrystallization solvent systems include acetonitrile, methanol and tetrahydrofuran. Fractionation may be performed on a suitable solid column supports such as alumina, using methanol/n-propanol mixtures as the mobile phase; reverse phase column supports using trifluoroacetic acid/acetonitrile mixtures as the mobile phase; and ion exchange chromatography using water as the mobile phase. When anion exchange chromatography is performed, preferably a subsequent 0-500 mM sodium chloride gradient is employed.

In particular embodiments, modified amino acids having the formula

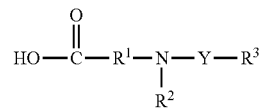

wherein Y is

or $SO_2$;
$R^1$ is $C_3$-$C_{24}$ alkylene, $C_2$-$C_{20}$ alkenylene, $C_2$-$C_{20}$ alkynylene, cycloalkylene, or an aromatic, such as arylene;
$R^2$ is hydrogen, $C_1$-$C_4$ alkyl, or $C_2$-$C_4$ alkenyl; and
$R^3$ is $C_1$—C alkyl, $C_3$-$C_{10}$ cycloalkyl, aryl, thienyl, pyrrolo, or pyridyl, and
$R^3$ is optionally substituted by one or more $C_1$-$C_5$ alkyl group, $C_2$-$C_4$ alkenyl group, F, Cl, OH, $OR^1$, $SO_2$, COOH, $COOR^1$ or, $SO_3H$;
may be prepared by

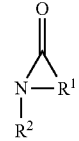

reacting in water and the presence of a base a lactam having the formula with a compound having the formula $R^3$—Y—X, wherein Y, $R^1$, $R^2$, and $R^3$ are as above and X is a leaving group. A lactam as shown in the above formula can be prepared, for example by the method described in Olah et al., Synthesis, 537-538 (1979).

In particular embodiments, modified amino acids also include an amino acid acylated at its alpha amino group with a fatty acid, which can be represented by the general formula A-X, wherein A is the alpha-amino acid residue and X is a fatty acid attached by acylation to A's alpha-amino group. The amino acids include cationic and non-cationic amino acids. In particular embodiments the term "non-cationic amino acid" refers to an amino acid selected from the group consisting of non-polar hydrophobic amino acids, polar non-charged amino acids, and polar acidic amino acids. In particular embodiments the term "non-cationic amino acid" as used herein refers to amino acids selected from the group consisting of Alanine (Ala), Valine (Val), Leucine (Leu), Isoleucine (Ile), Phenylalanine (Phe), Tryptophane (Trp), Methionine (Met), Proline (Pro), Sarcosine, Glycine (Gly), Serine (Ser), Threonine (Thr), Cysteine (Cys), Tyrosine (Tyr), Asparagine (Asn), and Glutamine (Gln), Aspartic acid (Asp), and Glutamic acid In particular embodiments, the acylated FA-aa includes an alpha amino acid residue of a non-polar hydrophobic amino acid. In particular embodiments, the acylated FA-aa may be represented by the general formula A-X, wherein A is the amino acid residue of a non-polar hydrophobic amino acid and X is a fatty acid attached by acylation to A's alpha-amino group. In particular embodiments the term "non-polar hydrophobic amino acid" as used herein refers to categorisation of amino acids used by the person skilled in the art. In particular embodiments the term "non-polar hydrophobic amino acid" refers to an amino acid selected from the group consisting of Alanine (Ala), Valine (Val), Leucine (Leu), Isoleucine (Ile), Phenylalanine (Phe), Tryptophane (Trp), Methionine (Met), Proline (Pro) and Sarcosine.

In particular embodiments, the acylated FA-aa includes the amino acid residue of a polar non-charged amino acid. In particular embodiments the acylated FA-aa may be represented by the general formula A-X, wherein A is the amino acid residue of a polar non-charged amino acid and X is a fatty acid attached by acylation to A's alpha-amino group. In particular embodiments the term "polar non-charged amino acid" as used herein refers to categorisation of amino acids used by the person skilled in the art. In particular embodiments the term "polar non-charged amino acid" refers to an amino acid selected from the group consisting of Glycine (Gly), Serine (Ser), Threonine (Thr), Cysteine (Cys), Tyrosine (Tyr), Asparagine (Asn), and Glutamine (Gln).

In particular embodiments, the acylated FA-aa includes the amino acid residue of a polar acidic amino acid. In particular embodiments, the acylated FA-aa may be represented by the general formula A-X, wherein A is the amino acid residue of a polar acidic amino acid and X is a fatty acid attached by acylation to A's alpha-amino group. In particular embodiments, the term "polar acidic amino acid" as used herein refers to categorisation of amino acids used by the person skilled in the art. In particular embodiments, the term "polar acidic amino acid" refers to an amino acid selected from the group consisting of Aspartic acid (Asp) and Glutamic acid (Glu).

In particular embodiments, the amino acid residue of the acylated FA-aa includes the amino acid residue of an amino acid that is not encoded by the genetic code. Modifications of amino acids by acylation may be readily performed using acylation agents known in the art that react with the free alpha-amino group of the amino acid.

In particular embodiments, the alpha-amino acids or the alpha-amino acid residues herein are in the L-form unless otherwise stated.

In particular embodiments, the amino acid residue is in the free acid form and/or a salt thereof, such as a sodium (Na+) salt thereof.

Exemplary embodiments of acylated FA-aas may be represented by the general Fa-aa formula I:

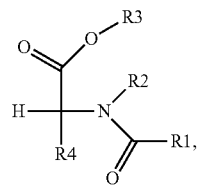

wherein R1 is an alkyl or aryl group including 5 to 19 carbon atoms; R2 is H (i.e. hydrogen), $CH_3$ (i.e. methyl group), or covalently attached to R4 via a $(CH_2)_3$ group; R3 is H or absent; and R4 is an amino acid side chain or covalently attached to R2 via a $(CH_2)_3$ group; or a salt thereof.

The FA-aa can be acylated with a fatty acid including a substituted or unsubstituted alkyl group consisting of 5 to 19 carbon atoms. In particular embodiments, the alkyl group consists of 5 to 17 carbon atoms. In particular embodiments, the alkyl group consists of 5-15 carbon atoms. In particular embodiments the alkyl group consists of 5-13 carbon atoms. In particular embodiments the alkyl group consists of 6 carbon atoms.

In particular embodiments, the acylated FA-aa is soluble at intestinal pH values, particularly in the range pH 5.5 to 8.0, such as in the range pH 6.5 to 7.0. In particular embodiments, the acylated FA-aa is soluble below pH 9.0.

In particular embodiments, the acylated FA-aa has a solubility of at least 5 mg/mL. In particular embodiments, the acylated FA-aa has a solubility of at least 10 mg/mL. In particular embodiments, the acylated FA-aa has a solubility of at least 20 mg/mL. In particular embodiments, the acylated FA-aa has a solubility of at least 30 mg/mL. In particular embodiments, the acylated FA-aa has a solubility of at least 40 mg/mL. In particular embodiments, the acylated FA-aa has a solubility of at least 50 mg/mL. In particular embodiments, the acylated FA-aa has a solubility of at least 60 mg/mL. In particular embodiments, the acylated FA-aa has a solubility of at least 70 mg/mL. In particular embodiments, the acylated FA-aa has a solubility of at least 80 mg/mL. In particular embodiments, the acylated FA-aa has a solubility of at least 90 mg/mL. In particular embodiments, the acylated FA-aa has a solubility of at least 100 mg/mL. In particular embodiments, solubility of the acylated FA-aa is determined in an aqueous solution at a pH value 1 unit above or below pKa of the FA-aa at 37° C. In particular embodiments, solubility of the acylated FA-aa is determined in an aqueous solution at pH 8 at 37° C. In particular embodiments, solubility of the acylated FA-aa is determined in an aqueous solution at a pH value 1 unit above or below pI of the FA-aa at 37° C. In particular embodiments, solubility of the acylated FA-aa is determined in an aqueous solution at a pH value 1 units above or below pI of the FA-aa at 37° C., wherein said FA-aa two or more ionisable groups with opposite charges. In particular embodiments, solubility of the FA-aa is determined in an aqueous 50 mM sodium phosphate buffer, pH 8.0 at 37° C.

Figure 3:
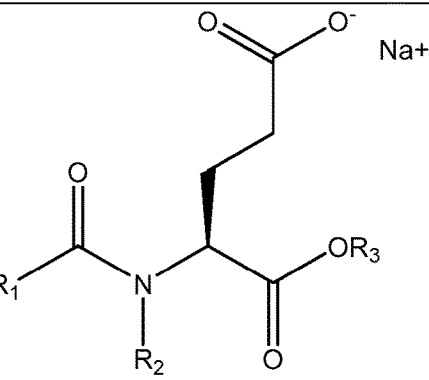
FIG. 3 provides fatty acid amino acids of formula (a), (b), (c), (d), (e), (f), (g), (h), (i), (j), (k), (l), (m), (n), (o), (p), (q), and (r), wherein R1 is an alkyl group including 5 to 19 carbon atoms, R2 is H (i.e. hydrogen) or CH3 (i.e. methyl group), and R3 is H; or a salt or the free acid form thereof.
Figure 3:
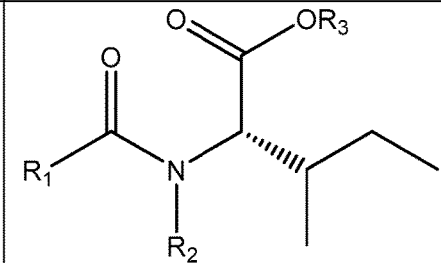
Figure 3:
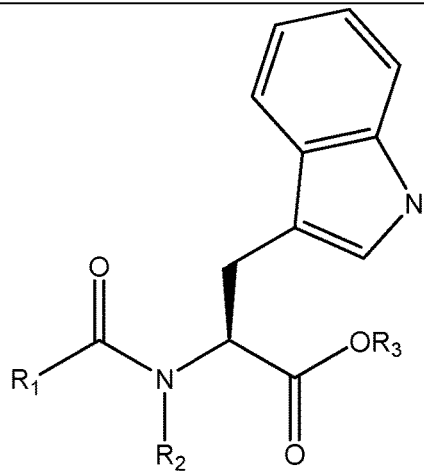
Figure 3:
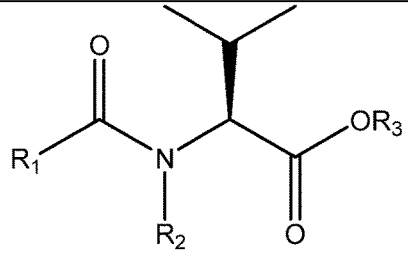
Figure 3:
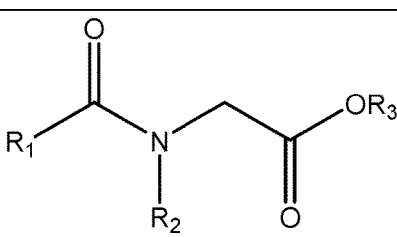
Figure 3:
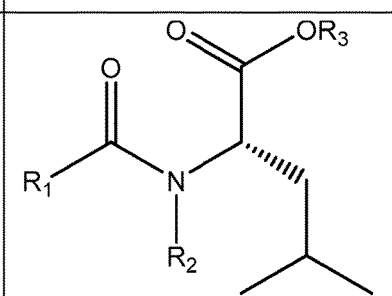
Figure 3:
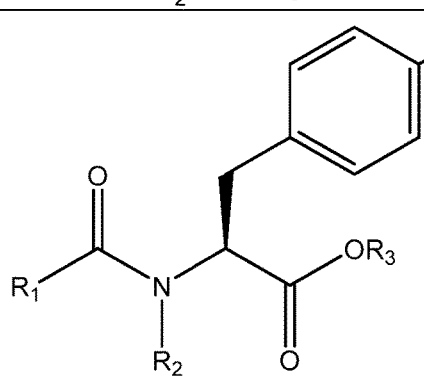
Figure 3:
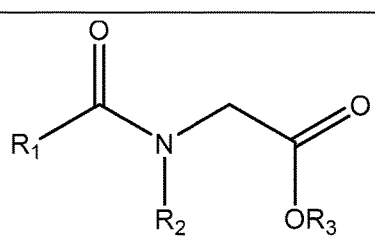

In particular embodiments the acylated FA-aa is selected from the group consisting of formula (a), (b), (c), (d), (e), (f), (g), (h), (i), (j), (k), (l), (m), (n), (o), (p), (q), and (r), wherein R1 is an alkyl group including 5 to 19 carbon atoms, R2 is H (i.e. hydrogen) or $CH_3$ (i.e. methyl group), and R3 is H; or a salt or the free acid form thereof. Formulas (a), (b), (c), (d), (e), (f), (g), (h), (i), (j), (k), (l), (m), (n), (o), (p), (q), and (r) are provided in FIG. 3.

In particular embodiments, the acylated FA-aa can be selected from one or more of sodium N-dodecanoyl alaninate, N-dodecanoyl-L-alanine, sodium N-dodecanoyl isoleucinate, N-dodecanoyl-L-isoleucine, sodium N-dodecanoyl leucinate, N-dodecanoyl-L-leucine, sodium N-dodecanoyl methioninate, N-dodecanoyl-L-methionine, sodium N-dodecanoyl phenylalaninate, N-dodecanoyl-L-phenylalanine, sodium N-dodecanoyl prolinate, N-dodecanoyl-L-proline, sodium N-dodecanoyl tryptophanate, N-dodecanoyl-L-tryptophane, sodium N-dodecanoyl valinate, N-dodecanoyl-L-valine, sodium N-dodecanoyl sarcosinate, N-dodecanoyl-L-sarcosine, sodium N-oleoyl sarcosinate, sodium N-decyl leucine, sodium N-decanoyl alaninate, N-decanoyl-L-alanine, sodium N-decanoyl leucinate, N-decanoyl-L-leucine, sodium N-decanoyl phenylalaninate, N-decanoyl-L-phenylalanine, sodium N-decanoyl valinate, N-decanoyl-L-valine, sodium N-decanoyl isoleucinate, N-decanoyl-L-isoleucine, sodium N-decanoyl methioninate, N-decanoyl-L-methionine, sodium N-decanoyl prolinate, N-decanoyl-L-proline, sodium N-decanoyl threoninate, N-decanoyl-L-threonine, sodium N-decanoyl tryptophanate, N-decanoyl-L-tryptophane, sodium N-decanoyl sarcosinate, N-decanoyl-L-Sarcosine, N-dodecanoyl asparaginate, N-dodecanoyl-L-asparagine, sodium N-dodecanoyl aspartic acid, N-dodecanoyl-L-aspartic acid, sodium N-dodecanoyl cysteinate, N-dodecanoyl-L-cysteine, sodium N-dodecanoyl glutaminate, N-dodecanoyl-L-glutamine, sodium N-dodecanoyl glycinate, N-dodecanoyl-L-glycine, sodium N-dodecanoyl serinate, N-dodecanoyl-L-serine, sodium N-dodecanoyl threoninate, N-dodecanoyl-L-threonine, sodium N-dodecanoyl tyrosinate, N-dodecanoyl-L-tyrosine, sodium N-decanoyl asparaginate, N-decanoyl-L-asparagine, sodium N-decanoyl aspartic acid, N-decanoyl-L-aspartic acid, sodium N-decanoyl cysteinate, N-decanoyl-L-cysteine, sodium N-decanoyl glutaminate, N-decanoyl-L-glutamine, sodium N-decanoyl glycinate, N-decanoyl-L-glycine, sodium N-decanoyl serinate, N-decanoyl-L-serine, sodium N-decanoyl tyrosinate, N-decanoyl-L-tyrosine, sodium N-dodecanoyl asparaginate, sodium N-dodecanoyl glutamic acid, N-dodecanoyl-L-glutamic acid, sodium N-decanoyl glutamic acid, N-decanoyl-L-glutamic acid, Amisoft HS-11 P (sodium Stearoyl Glutamate, Amisoft MS-11 (sodium Myristoyl Glutamate), Amisoft LS-11 (sodium Dodecanoyl Glutamate), Amisoft CS-11 (sodium Cocoyl Glutamate), sodium N-cocoyl glutamate, Amisoft HS-11 P, Amisoft HS-11 P (sodium N-stearoyl glutamate), (sodium N-myristoyl glutamate)), (sodium N-dodecanoyl glutamate), and Amisoft HS-11 P.

The following acylated FA-aas are commercially available:

TABLE 1

Commercially Available Acylated FA-aas.

| Brand Name | Chemical Name | Provider (per 14 APR. 2011) |
|---|---|---|
| Hamposyl L-95 | sodium N-dodecanoyl sarcosinate | Chattem Chemicals |
| Hamposyl O | sodium N-oleoyl sarcosinate | Chattem Chemicals |
| Hamposyl C | sodium N-cocoyl sarcosinate | Chattem Chemicals |
| Hamposyl L-30 | sodium N-dodecanoyl sarcosinate | Chattem Chemicals |
| Amisoft HS-11 P | sodium N-stearoyl glutamate | Ajinomoto |
| Amisoft LS-11 | sodium N-dodecanoyl glutamate | Ajinomoto |
| Amisoft CS-11 | sodium N-cocoyl glutamate | Ajinomoto |
| Amisoft MS-11 | sodium N-myristoyl glutamate | Ajinomoto |
| Amilite GCS-11 | sodium N-cocoyl glycinate | Ajinomoto |

In particular embodiments the terms "fatty acid N-acylated amino acid", "fatty acid acylated amino acid", or "acylated amino acid" are used interchangeably herein and refer to an amino acid that is acylated with a fatty acid at its alpha-amino group.

(III) ORAL FORMULATIONS

Exemplary oral formulations include capsules, coated tablets, edibles, elixirs, emulsions, gels, gelcaps, granules, gums, juices, liquids, oils, pastes, pellets, pills, powders, rapidly-dissolving tablets, sachets, semi-solids, sprays, solutions, suspensions, syrups, tablets, etc.

Exemplary excipient classes include binders, buffers, chelators, coating agents, colorants, complexation agents, diluents (i.e., fillers), disintegrants, emulsifiers, flavoring agents, glidants, lubricants, preservatives, releasing agents, surfactants, stabilizing agents, solubilizing agents, sweeteners, thickening agents, wetting agents, and vehicles.

Binders are substances used to cause adhesion of powder particles in granulations. Exemplary binders include acacia, compressible sugar, gelatin, sucrose and its derivatives, maltodextrin, cellulosic polymers, such as ethylcellulose, hydroxypropylcellulose, hydroxypropylmethyl cellulose, carboxymethylcellulose sodium and methylcellulose, acrylic polymers, such as insoluble acrylate ammoniomethacrylate copolymer, polyacrylate or polymethacrylic copolymer, povidones, copovidones, polyvinylalcohols, alginic acid, sodium alginate, starch, pregelatinized starch, guar gum, and polyethylene glycol.

Colorants may be included in the oral formulations to impart color to the formulation. Exemplary colorants include grape skin extract, beet red powder, beta carotene, annato, carmine, turmeric, and paprika. Additional colorants include FD&C Red No. 3, FD&C Red No. 20, FD&C Yellow No. 6, FD&C Blue No. 2, D&C Green No. 5, FD&C Orange No. 5, D&C Red No. 8, caramel, and ferric oxide.

Diluents can enhance the granulation of oral formulations. Exemplary diluents include microcrystalline cellulose, sucrose, dicalcium phosphate, starches, lactose and polyols of less than 13 carbon atoms, such as mannitol, xylitol, sorbitol, maltitol and pharmaceutically acceptable amino acids, such as glycin.

Disintegrants also may be included in the oral formulations in order to facilitate dissolution. Disentegrants, including permeabilising and wicking agents, are capable of drawing water or saliva up into the oral formulations which promotes dissolution from the inside as well as the outside of the oral formulations. Such disintegrants, permeabilising and/or wicking agents that may be used include starches, such as corn starch, potato starch, pre-gelatinized and modified starches thereof, cellulosic agents, such as Ac-di-sol, montmorrilonite clays, cross-linked PVP, sweeteners, bentonite, microcrystalline cellulose, croscarmellose sodium, alginates, sodium starch glycolate, gums, such as agar, guar, locust bean, karaya, pectin, Arabic, xanthan and tragacanth, silica with a high affinity for aqueous solvents, such as colloidal silica, precipitated silica, maltodextrins, beta-cyclodextrins, polymers, such as carbopol, and cellulosic agents, such as hydroxymethylcellulose, hydroxypropylcellulose and hydroxyopropylmethylcellulose. Dissolution of the oral formulations may be facilitated by including relatively small particles sizes of the ingredients used.

Exemplary dispersing or suspending agents include acacia, alginate, dextran, fragacanth, gelatin, hydrogenated edible fats, methylcellulose, polyvinylpyrrolidone, sodium carboxymethyl cellulose, sorbitol syrup, and synthetic natural gums.

Exemplary emulsifiers include acacia and lecithin.

Flavorants are natural or artificial compounds used to impart a pleasant flavor and often odor to oral formulations. Exemplary flavorants include, natural and synthetic flavor oils, flavoring aromatics, extracts from plants, leaves, flowers, and fruits and combinations thereof. Such flavorants include anise oil, cinnamon oil, vanilla, vanillin, cocoa, chocolate, natural chocolate flavor, menthol, grape, peppermint oil, oil of wintergreen, clove oil, bay oil, anise oil, *eucalyptus*, thyme oil, cedar leave oil, oil of nutmeg, oil of sage, oil of bitter almonds, *cassia* oil; citrus oils, such as lemon, orange, lime and grapefruit oils; and fruit essences, including apple, pear, peach, berry, wildberry, date, blueberry, kiwi, strawberry, raspberry, cherry, plum, pineapple, and apricot. In particular embodiments, flavorants that may be used include natural berry extracts and natural mixed berry flavor, as well as citric and malic acid.

Glidants improve the flow of powder blends during manufacturing and minimize oral formulation weight variation. Exemplary glidants include silicon dioxide, colloidal or fumed silica, magnesium stearate, calcium stearate, stearic acid, cornstarch, and talc.

Lubricants are substances used in oral formulations that reduce friction during composition compression. Exemplary lubricants include stearic acid, calcium stearate, magnesium stearate, zinc stearate, talc, mineral and vegetable oils, benzoic acid, poly(ethylene glycol), glyceryl behenate, stearyl fumarate, and sodium lauryl sulfate.

Exemplary preservatives include methyl p-hydroxybenzoates, propyl p-hydroxybenzoates, and sorbic acid.

Exemplary sweeteners include aspartame, dextrose, fructose, high fructose corn syrup, maltodextrin, monoammonium glycyrrhizinate, neohesperidin dihydrochalcone, potassium acesulfame, saccharin sodium, stevia, sucralose, and sucrose.

Particular embodiments include swallowable compositions. Swallowable compositions are those that do not readily dissolve when placed in the mouth and may be swallowed whole without chewing or discomfort. U.S. Pat. Nos. 5,215,754 and 4,374,082 describe methods for preparing swallowable compositions. In particular embodiments, swallowable compositions may have a shape containing no sharp edges and a smooth, uniform and substantially bubble free outer coating.

To prepare swallowable compositions, each of the ingredients may be combined in intimate admixture with a suitable carrier according to conventional compounding techniques. In particular embodiments of the swallowable compositions, the surface of the compositions may be coated with a polymeric film. Such a film coating has several beneficial effects. First, it reduces the adhesion of the compositions to the inner surface of the mouth, thereby increasing the subject's ability to swallow the compositions. Second, the film may aid in masking the unpleasant taste of certain ingredients. Third, the film coating may protect the compositions from atmospheric degradation. Polymeric films that may be used in preparing the swallowable compositions include vinyl polymers such as polyvinylpyrrolidone, polyvinyl alcohol and acetate, cellulosics such as methyl and ethyl cellulose, hydroxyethyl cellulose and hydroxylpropyl methylcellulose, acrylates and methacrylates, copolymers such as the vinyl-maleic acid and styrene-maleic acid types, and natural gums and resins such as zein, gelatin, shellac and acacia.

In particular embodiments, the oral formulations may include chewable compositions.

Chewable compositions are those that have a palatable taste and mouthfeel, are relatively soft and quickly break into smaller pieces and begin to dissolve after chewing such that they are swallowed substantially as a solution.

U.S. Pat. No. 6,495,177 describes methods to prepare chewable compositions with improved mouthfeel. U.S. Pat. No. 5,965,162, describes kits and methods for preparing comestible units which disintegrate quickly in the mouth, especially when chewed.

In order to create chewable compositions, certain ingredients should be included to achieve the attributes just described. For example, chewable compositions should include ingredients that create pleasant flavor and mouthfeel and promote relative softness and dissolvability in the mouth. The following discussion describes ingredients that may help to achieve these characteristics.

Sugars such as white sugar, corn syrup, sorbitol (solution), maltitol (syrup), oligosaccharide, isomaltooligosaccharide, sucrose, fructose, lactose, glucose, lycasin, xylitol, lactitol, erythritol, mannitol, isomaltose, dextrose, polydextrose, dextrin, compressible cellulose, compressible honey, compressible molasses and mixtures thereof may be added to improve mouthfeel and palatability. Fondant or gums such as gelatin, agar, arabic gum, guar gum, and carrageenan may be added to improve the chewiness of the compositions. Fatty materials that may be used include vegetable oils (including palm oil, palm hydrogenated oil, corn germ hydrogenated oil, castor hydrogenated oil, cotton-seed oil, olive oil, peanut oil, palm olein oil, and palm stearin oil), animal oils (including refined oil and refined lard whose melting point ranges from 30° to 42° C.), Cacao fat, margarine, butter, and shortening.

Alkyl polysiloxanes (commercially available polymers sold in a variety of molecular weight ranges and with a variety of different substitution patterns) also may be used to enhance the texture, the mouthfeel, or both of chewable compositions. By "enhance the texture" it is meant that the alkyl polysiloxane improves one or more of the stiffness, the brittleness, and the chewiness of the chewable composition, relative to the same preparation lacking the alkyl polysiloxane. By "enhance the mouthfeel" it is meant that the alkyl polysiloxane reduces the gritty texture of the chewable composition once it has liquefied in the mouth, relative to the same preparation lacking the alkyl polysiloxane.

Alkyl polysiloxanes generally include a silicon and oxygen-containing polymeric backbone with one or more alkyl groups pending from the silicon atoms of the back bone. Depending upon their grade, they can further include silica gel. Alkyl polysiloxanes are generally viscous oils. Exemplary alkyl polysiloxanes that can be used in swallowable, chewable or dissolvable compositions include monoalkyl or dialkyl polysiloxanes, wherein the alkyl group is independently selected at each occurrence from a $C_1$-$C_6$-alkyl group optionally substituted with a phenyl group. A specific alkyl polysiloxane that may be used is dimethyl polysiloxane (generally referred to as simethicone). More specifically, a granular simethicone preparation designated simethicone GS may be used. Simethicone GS is a preparation which contains 30% simethicone USP. Simethicone USP contains not less than 90.5% by weight $(CH_3)_3$—$Si\{OSi(CH_3)_2\}CH_3$ in admixture with 4.0% to 7.0% by weight $SiO_2$.

To prevent the stickiness that can appear in some chewable compositions and to facilitate conversion of the active ingredients to emulsion or suspension upon taking, the compositions may further include emulsifiers such as glycerin fatty acid ester, sorbitan monostearate, sucrose fatty acid ester, lecithin and mixtures thereof. In particular embodiments, one or more of such emulsifiers may be present in an amount of 0.01% to 5.0%, by weight of the administered formulations. If the level of emulsifier is lower or higher, in particular embodiments, an emulsification cannot be realized, or wax value will rise.

Liquid preparations for oral administration may take the form of, for example, solutions, syrups or suspensions, or they may be presented as a dry product for reconstitution with water or other suitable vehicles before use.

In addition to those described above, any appropriate fillers and excipients may be utilized in preparing the swallowable, chewable and/or dissolvable compositions or any other oral formulation described herein so long as they are consistent with the described objectives.

Oral formulations also include edibles. Edibles refer to any product that can be consumed as a food or a drink. In some cases, edibles are made by infusion of plant extracts or synthetic cannabinoids into a foodstuff. Examples of edible foods appropriate for use include candy, a candy bar, bread, a brownie, cake, cheese, chocolate, cocoa, a cookie, gummy candy, a lollipop, a mint, a pastry, peanut butter, popcorn, a protein bar, rice cakes, yogurt, etc. While technically not edible, gums can also be used. Examples of edible drinks include beer, juice, flavored milk, flavored water, liquor, milk, punch, a shake, soda, tea, and water. In particular embodiments, edibles are made by combining a plant extract or synthetic cannabinoids with ingredients used to make an edible. Examples include butters and oils. Exemplary oils include coconut oil, grape seed oil, olive oil, palm oil, papaya seed oil, peanut oil, sesame oil, sprouted wheat oil, wheat germ oil, or any combination thereof.

Oral formulations can be individually wrapped or packaged as multiple units in one or more packages, cans, vials, blister packs, or bottles of any size. Doses are sized to provide therapeutically effective amounts.

In particular embodiments, the oral formulations include vegetable matter (e.g., plant parts or extracts) or synthetic cannabinoids of at least 0.1% w/v or w/w of the oral formulation; at least 1% w/v or w/w of oral formulation; at least 10% w/v or w/w of oral formulation; at least 20% w/v or w/w of oral formulation; at least 30% w/v or w/w of oral formulation; at least 40% w/v or w/w of oral formulation; at least 50% w/v or w/w of oral formulation; at least 60% w/v or w/w of oral formulation; at least 70% w/v or w/w of oral formulation; at least 80% w/v or w/w of oral formulation; at least 90% w/v or w/w of oral formulation; at least 95% w/v or w/w of oral formulation; or at least 99% w/v or w/w of oral formulation.

In particular embodiments, the oral formulations include carrier of at least 0.1% w/v or w/w of the oral formulation; at least 1% w/v or w/w of oral formulation; at least 10% w/v or w/w of oral formulation; at least 20% w/v or w/w of oral formulation; at least 30% w/v or w/w of oral formulation; at least 40% w/v or w/w of oral formulation; at least 50% w/v or w/w of oral formulation; at least 60% w/v or w/w of oral formulation; at least 70% w/v or w/w of oral formulation; at least 80% w/v or w/w of oral formulation; at least 90% w/v or w/w of oral formulation; at least 95% w/v or w/w of oral formulation; or at least 99% w/v or w/w of oral formulation.

In particular embodiments, the oral formulations include excipient of at least 0.1% w/v or w/w of the oral formulation; at least 1% w/v or w/w of oral formulation; at least 10% w/v or w/w of oral formulation; at least 20% w/v or w/w of oral formulation; at least 30% w/v or w/w of oral formulation; at least 40% w/v or w/w of oral formulation; at least 50% w/v or w/w of oral formulation; at least 60% w/v or w/w of oral formulation; at least 70% w/v or w/w of oral formulation; at least 80% w/v or w/w of oral formulation; at least 90% w/v or w/w of oral formulation; at least 95% w/v or w/w of oral formulation; or at least 99% w/v or w/w of oral formulation.

In particular embodiments, 10 g of dried plant extract may be used in 150 ml of water. This may give an effective concentration of between 1 and 99% (w/w) plant extract, between 2 and 80% (w/w) plant extract, and between 5 and 50% (w/w) plant extract.

Excipients are commercially available from companies such as Aldrich Chemical Co., FMC Corp, Bayer, BASF, Alexi Fres, Witco, Mallinckrodt, Rhodia, ISP, and others.

As indicated previously, oral formulations described herein include a cannabinoid to N-acylated fatty amino acid w/w ratio of 1:4, 1:5, 1:6, 1:7, 1:8, 1:9, 1:10, 1:11, 1:12, 1:13, 1:14, 1:15, 1:16, 1:17, 1:18, 1:19, 1:20, 1:21, 1:22, 1:23, 1:24, 1:25.

Exemplary Formulations. Solution formulation. One or more cannabinoids and one or more N-acylated fatty amino acids are combined in an aqueous/organic solvent mixture at a 1:6, 1:10, or 1:20 w/w ratio. The resulting blend is stirred vigorously. One or more surfactants can be added to prepare the final formulation.

Suspension formulation (Oral Solution). One or more cannabinoids and one or more N-acylated fatty amino acids are combined in water, an aqueous/organic solvent mixture or an organic solvent mixture at a 1:6, 1:10, or 1:20 w/w ratio. The resulting blend can be stirred to effect suspension.

Solution formulation. One or more cannabinoids and one or more absorption enhancing agents are combined in an aqueous/organic solvent mixture at a 1:6, 1:10, or 1:20 w/w ratio. The resulting blend is stirred vigorously. One or more surfactants can be added to prepare the final formulation.

Suspension formulation (Oral Solution). One or more cannabinoids and one or more absorption enhancing agents are combined in water, an aqueous/organic solvent mixture or an organic solvent mixture at a 1:6, 1:10, or 1:20 w/w ratio. The resulting blend can be stirred to effect suspension.

Gelcap composition. A suspension formulation or solution formulation can be filled into a gelcap to contain up to 1 g of cannabinoid. The gelcap can be treated with an enteric coat or used without a coating.

Capsules (e.g., gelatin-based or vegetarian). Powders comprising one or more cannabinoids and one or more N-acylated fatty amino acids can be prepared using wet granulation techniques. The resulting dried powders can contain cannabinoid and an N-acylated fatty amino acid at a 1:6, 1:10, or 1:20 (w:w), ratio. The powders can be filled into commercially-available capsules.

Tablet/capsule composition. The solution formulation and the suspension formulation can be dried by evaporation, lyophilization, or spray drying. The resultant dry product can be combined with tableting excipients and compressed into tablets or caplets to contain up to 1 g of cannabis. Alternatively, the dry product can be filled into capsules.

Additional information can be found in WADE & WALLER, HANDBOOK OF PHARMACEUTICAL EXCIPIENTS (2nd ed. 1994) and Remington's Pharmaceutical Sciences, 18th Ed. Mack Printing Company, 1990. Moreover, formulations can be prepared to meet sterility, pyrogenicity, general safety, and purity standards as required by U.S. FDA and/or other relevant foreign regulatory agencies.

(IV) METHODS OF USE

Oral compositions disclosed herein can be used to treat subjects (humans, veterinary animals (dogs, cats, reptiles, birds, etc.), livestock (horses, cattle, goats, pigs, chickens, etc.), and research animals (monkeys, rats, mice, fish, etc.)). Treating subjects includes providing therapeutically effective amounts. Therapeutically effective amounts include those that provide effective amounts, prophylactic treatments, and/or therapeutic treatments.

An "effective amount" is the amount of a composition necessary to result in a desired physiological change in a subject. Effective amounts are often administered for research purposes. Representative effective amounts disclosed herein can reduce pain perception in an animal model (neuropathic pain, acute pain, visceral pain), stimulate appetite in an animal model, reduce seizures (e.g., epileptic seizures) in an animal model, reverse bone loss in an animal model, relieve migraine (vasoconstrict cranial blood vessels) in an animal model, treat addiction in an animal model, reduce anxiety in an animal model, and/or reduce symptoms of asthma in an animal model.

A "prophylactic treatment" includes a treatment administered to a subject who does not display signs or symptoms of a disease or nutritional deficiency or displays only early signs or symptoms of a disease or nutritional deficiency, such that treatment is administered for the purpose of diminishing, preventing, or decreasing the risk of developing the disease or nutritional deficiency further. Thus, a prophylactic treatment functions as a preventative treatment against the development of diseases or nutritional deficiencies.

As one example of a prophylactic treatment, an oral formulation disclosed herein can be administered to a subject who is at risk of developing a migraine headache. An effective prophylactic treatment of a migraine headache occurs when the number of migraines per month experienced by a subject is reduced by at least 10% or in particular embodiments, by 25%.

As another example of a prophylactic treatment, an oral formulation disclosed herein can be administered to a subject who is at risk of having an epileptic seizure. An effective prophylactic treatment of epileptic seizures occurs when the number of seizures per month is reduced by at least 10% or in particular embodiments, by 25%.

As another example of a prophylactic treatment, an oral formulation disclosed herein can be administered to a subject who is at risk of suffering from neuropathic pain. An effective prophylactic treatment of neuropathic pain occurs when the occurrence of the neuropathic pain is reduced by at least 10%, or in particular embodiments, by 25% as measured by a standard subjective or objective pain assessment.

As another example of a prophylactic treatment, an oral formulation disclosed herein can be administered to a subject who is at risk of developing breakthrough pain. An effective prophylactic treatment of breakthrough pain occurs when the occurrence of breakthrough pain is reduced by 10%, and in particular embodiments, by 25% by a standard subjective or objective pain assessment.

As another example of a prophylactic treatment, an oral formulation disclosed herein can be administered to a subject who is at risk of developing chemotherapy induced nausea and vomiting (CINV). An effective prophylactic treatment of CINV occurs when CINV is reduced by 10%, and in particular embodiments, by 25% measured by a standard subjective or objective CINV assessment.

As an example of a prophylactic treatment of a nutritional deficiency, an oral formulation disclosed herein can be administered to a subject who is at risk of developing rickets from insufficient vitamin C, anemia from insufficient dietary iron, and/or bone loss from insufficient calcium. An effective prophylactic treatment of these conditions occurs when the conditions are avoided or delayed due to nutritional supplementation with an oral formulation disclosed herein.

A "therapeutic treatment" includes a treatment administered to a subject who has a disease or nutritional deficiency and is administered to the subject for the purpose of curing or reducing the severity of the disease or nutritional deficiency.

As one example of a therapeutic treatment, an oral formulation disclosed herein can be administered to a subject who has a migraine headache. An effective therapeutic treatment of the migraine headache occurs when the severity of the headache is reduced or relieved completely and/or the headache resolves more quickly measured by a standard subjective or objective headache assessment.

Another example of a therapeutic treatment includes administration of an oral formulation disclosed herein to a subject experiencing CINV. A therapeutic treatment of CINV occurs when the vomiting is reduced or ceases (or ceases more quickly) and the nausea is relieved measured by a standard subjective or objective CINV assessment.

Another example of a therapeutic treatment includes administration of an oral formulation disclosed to a subject who has osteoporosis. An effective therapeutic treatment of osteoporosis occurs when bone density has increased by 10% and in particular embodiments, by 25%.

Another example of a therapeutic treatment includes administration of an oral formulation disclosed herein to a subject who has anxiety. An effective therapeutic treatment of anxiety occurs when the severity of the anxiety is reduced or relieved completely and/or more quickly measured by a standard subjective or objective anxiety assessment.

Another example of a therapeutic treatment includes administration of an oral formulation disclosed herein to a subject who has multiple sclerosis. An effective therapeutic treatment of multiple sclerosis occurs when the score in a standard walk test improves by 10% and in particular embodiments, by 25%.

As one example of a therapeutic treatment of a nutritional deficiency, an oral formulation disclosed herein can be administered to a subject who has rickets from insufficient vitamin C, anemia from insufficient dietary iron, and/or bone loss from insufficient calcium. An effective therapeutic treatment of these conditions occurs when the conditions are reduced or resolved due to nutritional supplementation with an oral formulation disclosed herein.

Therapeutic treatments can be distinguished from effective amounts based on the presence or absence of a research component to the administration. As will be understood by one of ordinary skill in the art, however, in human clinical trials effective amounts, prophylactic treatments and therapeutic treatments can overlap.

For administration, therapeutically effective amounts (also referred to herein as doses) can be initially estimated based on results from in vitro assays and/or animal model studies. Such information can be used to more accurately determine useful doses in subjects of interest.

The actual dose amount administered to a particular subject can be determined by the subject, a physician, veterinarian, or researcher taking into account parameters such as physical, physiological and psychological factors including target, body weight, condition, previous or concurrent therapeutic interventions, and/or idiopathy of the subject.

Useful doses can range from 0.1 to 5 µg/kg or from 0.5 to 1 µg/kg. In other non-limiting examples, a dose can include 1 µg/kg, 5 µg/kg, 10 µg/kg, 15 µg/kg, 20 µg/kg, 25 µg/kg, 30 µg/kg, 35 µg/kg, 40 µg/kg, 45 µg/kg, 50 µg/kg, 55 µg/kg, 60 µg/kg, 65 µg/kg, 70 µg/kg, 75 µg/kg, 80 µg/kg, 85 µg/kg, 90 µg/kg, 95 µg/kg, 100 µg/kg, 150 µg/kg, 200 µg/kg, 250 µg/kg, 350 µg/kg, 400 µg/kg, 450 µg/kg, 500 µg/kg, 550 µg/kg, 600 µg/kg, 650 µg/kg, 700 µg/kg, 750 µg/kg, 800 µg/kg, 850 µg/kg, 900 µg/kg, 950 µg/kg, 1000 µg/kg, 0.1 to 5 mg/kg or from 0.5 to 1 mg/kg. In other non-limiting examples, a dose can include 1 mg/kg, 5 mg/kg, 10 mg/kg, 15 mg/kg, 20 mg/kg, 25 mg/kg, 30 mg/kg, 35 mg/kg, 40 mg/kg, 45 mg/kg, 50 mg/kg, 55 mg/kg, 60 mg/kg, 65 mg/kg, 70 mg/kg, 75 mg/kg, 80 mg/kg, 85 mg/kg, 90 mg/kg, 95 mg/kg, 100 mg/kg, 150 mg/kg, 200 mg/kg, 250 mg/kg, 350 mg/kg, 400 mg/kg, 450 mg/kg, 500 mg/kg, 550 mg/kg, 600 mg/kg, 650 mg/kg, 700 mg/kg, 750 mg/kg, 800 mg/kg, 850 mg/kg, 900 mg/kg, 950 mg/kg, 1000 mg/kg or more.

With the methods and oral formulations disclosed herein, variability in absorption that would otherwise be observed is reduced, for example, to below 50% CV, below 40%, or below 30%.

Therapeutically effective amounts can be achieved by administering single or multiple doses during the course of a treatment regimen (e.g., hourly, every 2 hours, every 3 hours, every 4 hours, every 6 hours, every 9 hours, every 12 hours, every 18 hours, daily, every other day, every 3 days, every 4 days, every 5 days, every 6 days, weekly, every 2 weeks, every 3 weeks, or monthly).

One or more active agent(s) can be administered simultaneously or within a selected time window, such as within 10 minutes, 1 hour, 3 hour, 10 hour, 15 hour, 24 hour, or 48 hour time windows or when the complementary active agent(s) is within a clinically-relevant therapeutic window.

(V) EXEMPLARY EMBODIMENTS

1. A method of preparing an oral cannabinoid formulation with reduced cannabinoid blood absorption variability in a subject including adding a cannabinoid and an effective amount of an N-acylated fatty amino acid or a salt thereof to an oral formulation.
2. The method of embodiment 1, wherein the effective amount of the N-acylated fatty amino acid or a salt thereof results in a cannabinoid/N-acylated fatty amino acid or a salt thereof weight/weight (w/w) ratio of 1:4-1:25 within the oral formulation.
3. The method of embodiment 1, wherein the effective amount of the N-acylated fatty amino acid or a salt thereof results in a cannabinoid/N-acylated fatty amino acid or a salt thereof weight/weight (w/w) ratio of 1:6, 1:10, or 1:20 within the oral formulation.
4. The method of any of embodiments 1-3, wherein the oral formulation includes 50 mg cannabinoid and 300 mg N-acylated fatty amino acid or a salt thereof; 10 mg cannabinoid and 100 mg N-acylated fatty amino acid or a salt thereof; 10 mg cannabinoid and 200 mg N-acylated fatty amino acid or a salt thereof; 50 mg cannabinoid and 500 mg N-acylated fatty amino acid or a salt thereof; or 30 mg cannabinoid and 300 mg N-acylated fatty amino acid or a salt thereof.
5. The method of any of embodiments 1-4, wherein the oral formulation includes 50 mg cannabidiol (CBD) and 300 mg N-acylated fatty amino acid or a salt thereof; 10 mg Δ9-Tetrahydrocannabinol (THC) and 100 mg N-acylated fatty amino acid or a salt thereof; 10 mg THC and 200 mg N-acylated fatty amino acid or a salt thereof; 50 mg CBD and 500 mg N-acylated fatty amino acid or a salt thereof; or 30 mg CBD and 300 mg N-acylated fatty amino acid or a salt thereof.
6. The method of any of embodiments 1-4, wherein the oral formulation includes 50 mg cannabinoid and 300 mg sodium N-[8-(2-hydroxybenzoyl) amino] caprylate (SNAC); 10 mg cannabinoid and 100 mg SNAC; 10 mg cannabinoid and 200 mg SNAC; 50 mg cannabinoid and 500 mg SNAC; or 30 mg cannabinoid and 300 mg SNAC.
7. The method of any of embodiments 1-4, wherein the oral formulation includes 50 mg CBD and 300 mg SNAC; 10 mg THC and 100 mg SNAC; 10 mg THC and 200 mg SNAC; 50 mg CBD and 500 mg SNAC; or 30 mg CBD and 300 mg SNAC.
8. The method of any of embodiments 1-7, wherein the oral formulation includes a powder.
9. The method of embodiment 8, wherein the powder is formed by wet granulation.
10. The method of any of embodiments 1-9, wherein the oral formulation includes a gelatin capsule.
11. The method of any of embodiments 1-10, wherein the oral formulation includes a powder formed by wet granulation and wherein the powder is within a gelatin capsule.
12. The method of any of embodiments 1-7, wherein the oral formulation includes an oral solution.
13. The method of any of embodiments 1-12, wherein the reduced cannabinoid blood absorption variability results in a coefficient of variation (% CV) of <50%, less than 40%, or less than 30%.
14. The method of any of embodiments 1-13, wherein the absorption includes gastrointestinal absorption into the blood.
15. The method of any of embodiments 1-4, 6, or 8-14, wherein the cannabinoid is derived from *Calophyllum brasiliense, Calophyllum caledonicurn, Calophyllum inophyllum, Calophyllum soulattri, Uncaria tomentosa, Thymus vulgaris, Matricaria recutita, Salix alba, Calendula officinalis, Usnea barbata, Ligusticum porterii-osha, Gaultheria procumbens, Camellia sinensis, Vaccinium myrtillus, Melissa officinalis, Allium sativum, Camellia sinensis, Krameria triandra, Punica granatum, Viburnum plicatum, Nicotiana tabacum, Duboisia hopwoodii, Asciepias syriaca, Curcuma Ionga, Cannabis sativa, Cannabis indica, Cannabis ruderalis* and/or *Acer* spp, or an extract thereof.
16. The method of any of embodiments 1-4, 6, or 8-14, wherein the cannabinoid is derived from *Cannabis sativa, Cannabis ruderalis*, or *Cannabis indica*.
17. The method of any of embodiments 1-4, 6, or 8-16, wherein the cannabinoid includes Δ9-Tetrahydrocannabinol (THC) and cannabidiol (CBD), cannabigerol (CBG), cannabichromene (CBC), cannabinol (CBN), cannabinodiol (CBDL), cannabicyclol (CBL), cannabivarin (CBV), tetrahydrocannabivarin (THCV), cannabidivarin (CBDV), cannabichromevarin (CBCV), cannabigerovarin (CBGV), cannabigerol monomethyl ether (CBGM), cannabinerolic acid, cannabidiolic acid (CBDA), Cannabinol propyl variant (CBNV), cannabitriol (CBO), tetrahydrocannabinolic acid (THCA), tetrahydrocannabivarinic acid (THCVA) and/or mixtures thereof.
18. The method of any of embodiments 1-17, wherein the cannabinoid includes a plant-based cannabinoid or a synthetic cannabinoid.
19. The method of any of embodiments 1-18, wherein the oral formulation includes flavonoid compounds, terpenes, or terpenoids.
20. The method of any of embodiments 1-5 or 8-19, wherein the N-acylated fatty amino acid includes one or more of Compounds I-XXXV (FIG. 2), or Compounds a-r (FIG. 3).
21. The method of any of embodiments 1-5 or 8-19, wherein the wherein the N-acylated fatty amino acid includes monosodium-N-salicyloyl-8-aminocaprylate, disodium-N-salicyloyl-8-aminocaprylate, or N-(salicyloyl)-8-aminocaprylic acid.
22. The method of any of embodiments 1-5 or 8-19, wherein the wherein the N-acylated fatty amino acid or a salt thereof includes

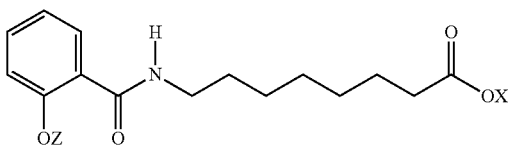

wherein X and Z are independently H, a monovalent cation, a divalent metal cation, or an organic cation.

23. The method of embodiment 22, wherein the wherein the monovalent cation is sodium or potassium.

24. The method of embodiment 22 or 23, wherein the metal cation is calcium or magnesium.

25. The method of any of embodiments 22-24, wherein the organic cation is ammonium or tetramethylammonium.

26. The method of any of embodiments 22-25, wherein X is H.

27. The method of any of embodiments 22-25, wherein X is a monovalent cation including sodium or potassium.

28. The method of any of embodiments 22-25, wherein X is a divalent metal cation including calcium or magnesium.

29. The method of any of embodiments 22-25, wherein X is an organic cation including ammonium or tetramethylammonium.

30. The method of any of embodiments 22-29, wherein Z is H.

31. The method of any of embodiments 22-29, wherein Z is a monovalent cation including sodium or potassium.

32. The method of any of embodiments 22-29, wherein Z is a divalent cation including calcium or magnesium.

33. The method of any of embodiments 22-25, wherein X is H and Z is H.

34. The method of any of embodiments 22-25, wherein X is H and Z is sodium.

35. The method of any of embodiments 22-25, wherein X is sodium and Z is sodium.

36. The method of any of embodiments 1-35, wherein the oral formulation is a medicinal composition.

37. The method any of embodiments 1-35, wherein the oral formulation is a nutritional supplement.

38. The method of any of embodiments 1-36, wherein the oral formulation is utilized to treat a symptom of acquired hypothyroidism, acute gastritis, addiction, ADHD, agoraphobia, AIDS, AIDS-related anorexia, alcoholism, Alzheimer's disease, amyotrophic lateral sclerosis (ALS), ankyloses, anxiety, arthritis, Asperger's syndrome, asthma, atherosclerosis, autism, auto-immune diseases, bacterial infections, bipolar disorder, bone loss, blood disorders, brain injury/stroke, cachexia, cancer, carpal tunnel syndrome, cerebral palsy, cervical disk disease, cervicobrachial syndrome, chronic fatigue syndrome, chronic pain, cluster headache, conjunctivitis, Crohn's disease, cystic fibrosis, depression, dermatitis, diabetes, dystonia, eating disorders, eczema, epilepsy, fever, fibromyalgia, flu, fungal infection, gastrointestinal disorders, glaucoma, glioma, Grave's disease, heart disease hepatitis, herpes, Huntington's disease, hypertension, impotence, incontinence, infant mortality, inflammation, inflammatory bowel disease (IBD), insomnia, liver fibrosis, mad cow disease, menopause, metabolic disorders, migraine headaches, motion sickness, MRSA, multiple sclerosis (MS), muscular dystrophy, mucosal lesions, nail patella syndrome, nausea and vomiting associated with cancer chemotherapy, neuroinflammation, nicotine addiction, obesity, obsessive compulsive disorder (OCD), pain, pancreatitis, panic disorder, Parkinson's disease, periodontal disease, peripheral neuropathy, phantom limb pain, poison ivy allergy, premenstrual syndrome (PMS), proximal myotonic myopathy, post-traumatic stress disorder (PTSD), psoriasis, Raynaud's disease, restless leg syndrome, schizophrenia, scleroderma, septic shock, shingles herpes zoster), sickle cell disease, seizures, sleep apnea, sleep disorders, spinal injuries, stress, stuttering, temporomandibular joint disorder (TMJ), tension headaches, tinnitus, Tourette's syndrome, traumatic memories, wasting syndrome, and withdrawal.

39. Use of an N-acylated fatty amino acid disclosed herein to reduce inter-subject variability in uptake of a cannabinoid following ingestion of an oral formulation including the cannabinoid.

40. An oral formulation formed according to the methods of any of embodiments 1-38.

(VI) EXEMPLARY EXPERIMENTAL PROCEDURES

Participants can be administered a commercially available cannabis extract within an ethanol solution. The concentrate can contain 8 mg THC per dose. This dose can be selected because it contains a high percentage of THC, which provides a noticeable effect on user-reported "euphoria". Aqueous ethanol can be used as solvent because it effectively dissolves cannabis extract, as well as SNAC.

In experimental procedures, each participant can mix the cannabis concentrate with 15 ml (one tablespoon) of aqueous ethanol, and immediately swallow the mixture. This treatment can constitute a control treatment. For a test treatment, each participant can mix the cannabis concentrate with a pre-mixed solution of aqueous ethanol and 200 mg SNAC, and immediately swallow the dissolved mixture.

Blood samples can be drawn from the participants at time points after administration, and the amount of cannabis in the blood samples can be measure.

(VII) EXPERIMENTAL EXAMPLES

Example 1

Participant selection: Healthy men and women between 21 and 55 years of age, inclusive, with a body mass index (BMI) between 18 and 30.0 kg/m$^2$, inclusive, and a body weight of not less than 50 kg were eligible to participate. Female participants were not pregnant or breast feeding. Participants were permitted to have used cannabis in the past but were not currently using it more than 3 times per week and not within 6 days of dosing, as confirmed by a CBD blood screen.

Formulations: Three powders including CBD and SNAC were prepared using wet granulation techniques. The resulting dried powders contained CBD and SNAC at 1:2, 1:6 and 1:10 (w:w), respectively, ratios. The powders were filled into gelatin capsules prior to dosing.

Methods: Participants were randomized to a treatment group and received the treatments below. All participants were slated to receive all treatments with a minimum 1-week washout period between treatments. The treatments included 50 mg CBD/100 mg SNAC (1:2 ratio); 50 mg CBD/300 mg SNAC (1:6 ratio); 50 mg CBD/500 mg SNAC (1:10 ratio); 30 mg CBD/300 mg SNAC (1:10 ratio); and 150 mg CBD/300 mg SNAC (1:2 ratio).

Participants fasted at least 10 hours before study treatment administration. Water was allowed until 1 hour before dosing and then ad libitum beginning 2 hours after dosing. Food was allowed 4 hours after dosing. Treatments were administered with 2 oz of water. Blood samples were drawn pre-dose and at 5, 10, 15, 30, 45, 60, 90, 120, 240, 480, and 720 minutes after dosing.

Blood samples were analyzed for concentrations of CBD and its major metabolite, 7-COOH CBD by a commercial laboratory using a validated liquid chromatography-mass spectrometry (LC-MS) method.

Results: AUC0-last, or the area under the plasma concentration-time curve from time zero to the last measurable time point, was calculated for each of the treatments administered (Table 2). Treatments that used 1:6 and 1:10 (w:w) ratios of CBD:SNAC demonstrated reduced variability, expressed as coefficient of variation (% CV), compared to treatments using 1:2 CBD:SNAC.

TABLE 2

AUC and % CV of various CBD treatments after administration to fasted healthy normal volunteers.

| Treatment | CBD AUC (h * pg/mL) | |
|---|---|---|
| | Average | % CV |
| 1:2 ratio (50 mg/100 mg) | 2976 | 63 |
| 1:2 ratio (150 mg/300 mg) | 6723 | 56 |
| 1:6 ratio (50 mg/300 mg) | 14865 | 39 |
| 1:10 ratio (30 mg/300 mg) | 4368 | 26 |
| 1:10 ratio (50 mg/500 mg) | 11022 | 33 |

Example 2

Participant selection: Healthy men and women between 21 and 55 years of age, inclusive, with a body mass index (BMI) between 18 and 30.0 kg/m², inclusive, and a body weight of not less than 50 kg were eligible to participate. Female participants were not pregnant or breast feeding. Participants were permitted to have used cannabis in the past but were not currently using it more than 3 times per week and not within 6 days of dosing, as confirmed by a THC urine screen.

Methods: Participants were randomized to a treatment group and received the treatments below. All participants were slated to receive all treatments with a minimum 1-week washout period between treatments. The treatments included: oral solution containing 10 mg THC (no SNAC); oral solution containing 10 mg THC and 100 mg SNAC; and oral solution containing 10 mg THC and 200 mg SNAC.

Participants fasted at least 10 hours before study treatment administration. Water was allowed until 1 hour before dosing and then ad libitum beginning 2 hours after dosing. Food was allowed 4 hours after dosing. Blood samples were drawn pre-dose and at 5, 10, 15, 30, 45, 60, 90, 120, 240, 480, and 720 minutes after dosing. Blood samples were analyzed for concentrations of THC and its major metabolite, 11-OH THC by a commercial laboratory using a validated liquid chromatography-mass spectrometry (LC-MS) method.

Results: AUC0-last, or the area under the plasma concentration-time curve from time zero to the last measurable time point, was calculated for each of the treatments administered (Table 3). Treatments that used 1:10 and 1:20 (w:w) ratios of THC:SNAC demonstrated reduced variability, expressed as coefficient of variation (% CV), compared to the control treatment without SNAC.

TABLE 3

AUC and % CV of various THC treatments after administration to fasted healthy normal volunteers.

| Treatment | THC AUC (h * pg/mL) | |
|---|---|---|
| | Average | % CV |
| 10 mg THC (no SNAC) | 8259.2 | 84.2 |
| 10 mg THC/100 mg SNAC | 11485.3 | 38.2 |
| 10 mg THC/200 mg SNAC | 18982.3 | 40.5 |

The results of Example 1 and Example 2 demonstrate that oral formulations of cannabinoids and N-acylated fatty amino acids reduce the inter-subject variability in AUC when the cannabinoid: N-acylated fatty amino acid ratio ranges from 1:6 to 1:20. The reduced variability results in a % CV of less than 50%, less than 40%, or less than 30% and can provide a 2-fold reduction in variability.

(VII) CLOSING PARAGRAPHS

As will be understood by one of ordinary skill in the art, each embodiment disclosed herein can comprise, consist essentially of or consist of its particular stated element, step, ingredient or component. Thus, the terms "include" or "including" should be interpreted to recite: "comprise, consist of, or consist essentially of." The transition term "comprise" or "comprises" means includes, but is not limited to, and allows for the inclusion of unspecified elements, steps, ingredients, or components, even in major amounts. The transitional phrase "consisting of" excludes any element, step, ingredient or component not specified. The transition phrase "consisting essentially of" limits the scope of the embodiment to the specified elements, steps, ingredients or components and to those that do not materially affect the embodiment. A material effect would cause a statistically significant increase in absorption variability and/or a % CV value above 50%.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. When further clarity is required, the term "about" has the meaning reasonably ascribed to it by a person skilled in the art when used in conjunction with a stated numerical value or range, i.e. denoting somewhat more or somewhat less than the stated value or range, to within a range of ±20% of the stated value; ±19% of the stated value; ±18% of the stated value; ±17% of the stated value; ±16% of the stated value; ±15% of the stated value; ±14% of the stated value; ±13% of the stated value; ±12% of the stated value; ±11% of the stated value; ±10% of the stated value; ±9% of the stated value; ±8% of the stated value; ±7% of the stated value; ±6% of the stated value; ±5% of the stated value; ±4% of the stated value; ±3% of the stated value; ±2% of the stated value; or ±1% of the stated value.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein.

Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents, printed publications, journal articles and other written text throughout this specification (referenced materials herein).

Each of the referenced materials are individually incorporated herein by reference in their entirety for their referenced teaching.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

The particulars shown herein are by way of example and for purposes of illustrative discussion of the preferred embodiments of the present invention only and are presented in the cause of providing what is believed to be the most useful and readily understood description of the principles and conceptual aspects of various embodiments of the invention. In this regard, no attempt is made to show structural details of the invention in more detail than is necessary for the fundamental understanding of the invention, the description taken with the drawings and/or examples making apparent to those skilled in the art how the several forms of the invention may be embodied in practice.

Definitions and explanations used in the present disclosure are meant and intended to be controlling in any future construction unless clearly and unambiguously modified in the following examples or when application of the meaning renders any construction meaningless or essentially meaningless. In cases where the construction of the term would render it meaningless or essentially meaningless, the definition should be taken from Webster's Dictionary, 3rd Edition or a dictionary known to those of ordinary skill in the art, such as the Oxford Dictionary of Biochemistry and Molecular Biology (Ed. Anthony Smith, Oxford University Press, Oxford, 2004).

What is claimed is:

1. A method of reducing cannabinoid blood absorption inter-subject variability, the method comprising:
    administering to a plurality of subjects an oral formulation comprising a cannabinoid with an aqueous solubility of less than 0.1 mg/ml selected from:
    Δ9-Tetrahydrocannabinol (THC), cannabidiol (CBD), cannabigerol (CBG), cannabichromene (CBC), cannabinol (CBN), cannabinodiol (CBDL), cannabicyclol (CBL), cannabivarin (CBV), tetrahydrocannabivarin (THCV), cannabidivarin (CBDV), cannabichromevarin (CBCV), cannabigerovarin (CBGV), cannabigerol monomethyl ether (CBGM), cannabinol propyl variant (CBNV), cannabitriol (CBO), and/or mixtures thereof;
    and an N-acylated fatty amino acid or salt thereof having a formula:

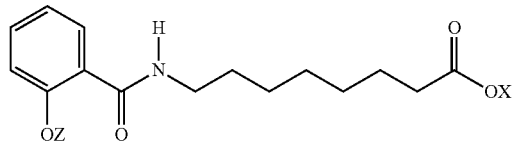

wherein X is sodium or potassium, and Z is hydrogen,
    wherein the weight/weight (w/w) ratio of cannabinoid/N-acylated fatty amino acid or salt thereof within the oral formulation is 1:6 or 1:10;
    thereby reducing the cannabinoid blood absorption inter-subject variability,
    wherein the reduced cannabinoid blood absorption inter-subject variability is evidenced by a coefficient of variation (% CV) of area under a plasma concentration-time curve that is less than 50%.

2. The method of claim 1, wherein the oral formulation comprising the cannabinoid and the N-acylated fatty amino acid or salt thereof comprises a powder or an oral solution.

3. The method of claim 1, wherein the oral formulation comprises
- 50 mg cannabidiol (CBD) and 300 mg N-acylated fatty amino acid or salt thereof;
- 10 mg Δ9-Tetrahydrocannabinol (THC) and 100 mg N-acylated fatty amino acid or salt thereof;
- 50 mg CBD and 500 mg N-acylated fatty amino acid or salt thereof; or
- 30 mg CBD and 300 mg N-acylated fatty amino acid or salt thereof.

4. The method of claim 1, wherein the cannabinoid comprises cannabidiol (CBD).

5. The method of claim 1, the N-acylated fatty amino acid or salt thereof comprises sodium N-[8-(2-hydroxybenzoyl) amino] caprylate (SNAC).

6. The method of claim 1, wherein the oral formulation comprises a gelatin capsule.

7. The method of claim 1, wherein the oral formulation further comprises flavonoid compounds, terpenes, or terpenoids.

8. The method of claim 2, wherein the powder is formed by wet granulation.

* * * * *